United States Patent
Sidhu et al.

(10) Patent No.: US 10,562,945 B2
(45) Date of Patent: Feb. 18, 2020

(54) SPECIFIC ACTIVE SITE INHIBITORS OF ENZYMES OR SUBSTRATE BINDING PARTNERS AND METHODS OF PRODUCING SAME

(71) Applicant: THE GOVERNING COUNCIL OF THE UNIVERSITY OF TORONTO, Toronto (CA)

(72) Inventors: Sachdev Sidhu, Toronto (CA); Linda Beatty, Toronto (CA); Andreas Ernst, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 16/239,784

(22) Filed: Jan. 4, 2019

(65) Prior Publication Data
US 2019/0194270 A1 Jun. 27, 2019

Related U.S. Application Data

(62) Division of application No. 13/814,146, filed as application No. PCT/IB2011/001663 on Jun. 8, 2011, now Pat. No. 10,214,570.

(60) Provisional application No. 61/372,133, filed on Aug. 10, 2010, provisional application No. 61/372,133, filed on Aug. 10, 2010.

(51) Int. Cl.
| A61K 38/17 | (2006.01) |
| C07K 14/435 | (2006.01) |
| C07K 14/47 | (2006.01) |

(52) U.S. Cl.
CPC ............ *C07K 14/435* (2013.01); *A61K 38/17* (2013.01); *C07K 14/47* (2013.01)

(58) Field of Classification Search
None
See application file for complete search history.

(56) References Cited

U.S. PATENT DOCUMENTS

| 4,373,071 A | 2/1983 | Itakura |
| 4,401,796 A | 8/1983 | Itakura |
| 4,458,066 A | 7/1984 | Caruthers et al. |
| 4,598,049 A | 7/1986 | Zelinka et al. |
| 7,179,650 B1 | 2/2007 | Yeh |
| 8,592,179 B2 | 11/2013 | Schraeml et al. |
| 8,790,895 B2 | 7/2014 | Fiedler et al. |
| 8,791,238 B2 | 7/2014 | Fiedler et al. |
| 2004/0214272 A1 | 10/2004 | La Rosa et al. |
| 2005/0186666 A1 | 8/2005 | Schneider et al. |
| 2006/0099686 A1 | 5/2006 | Fiedler et al. |

OTHER PUBLICATIONS

Avvakumov et al., Amino-terminal dimerization, NRDP1-rhodanese interaction, and inhibited catalytic domain conformation of the ubiquitin-specific protease 8 (USP8). *J. Biol. Chem.*, 281(49): 38061-70 (2006).

Bernassola et al., The HECT family of E3 ubiquitin ligases: multiple players in cancer development. *Cancer Cell*, 14(1): 10-21 (2008).
Case et al., Mechanistic studies of ubiquitin C-terminal hydrolase L1. *Biochemistry*, 45(7): 2443-2452 (2006).
Chen et al., Ubiquitin signalling in the NF-kappa B pathway. *Nat. Cell Biol.*, 7(8): 758-65 (2005).
Colland et al. Small-molecule inhibitor of USP7/HAUSP ubiquitin protease stabilizes and activates p53 in cells. *Molec. Cancer Therap.*, 8(8): 2286-95 (2009).
Cummins et al., HAUSP is required for p53 destabilization. *Cell Cycle*, 3(6): 689-92 (2004).
Dayal et al., Suppression of the deubiquitinating enzyme USP5 causes the accumulation of unanchored polyubiquitin and the activation of p53. *J. Biol. Chem.*, 284(8): 5030-41 (2009).
Fang et al., A field guide to ubiquitylation. *Cell Mol. Life Sci.*, 61(13): 1546-61 (2004).
Fedorov et al., A systematic interaction map of validated kinase inhibitors with Ser/Thr kinases. *Proc. Natl. Acad. Sci. USA*, 104(51): 20523-8 (2007).
Frische et al., Multiple column synthesis of a library of T-cell stimulating Tn-antigenic glycopeptide analogues for the molecular characterization of T-cell-glycan specificity. *J. Pept. Sci.*, 2(4): 212-22 (1996).
Glickman et al., The ubiquitin-proteasome proteolytic pathway: Destruction for the sake of construction. *Physiol. Rev.*, 82(2): 373-428 (2002).
Goldenberg et al., Strategies for the identification of novel inhibitors of deubiquitinating enzymes. *Biochem. Soc. Trans.*, 36:828-32 (2008).
Gray et al., Elevated expression of Unph, a protooncogene at 3p21.3, in human lung-tumors. *Oncogene*, 10(11): 2179-83 (1995).
Grunda et al., Increased expression of thymidylate synthetase (TS), ubiquitin specific protease 10 (USP10) and survivin is associated with poor survival in glioblastoma multiforme (GBM). *J. Neurooncol.*, 80(3): 261-74 (2006).
Hafner et al., Displacement of protein-bound aptamers with small molecules screened by fluorescence polarization. *Nat. Protoc.*, 3(4): 579-87 (2008).
Hershko et al., The ubiquitin system. *Ann. Rev. Biochem.*, 67: 425-79 (1998).
Hochstrasser, Origin and function of ubiquitin-like proteins, *Nature*, 458(7237):422-9 (2009).
Hu et al., Crystal structure of a UBP-family deubiquitinating enzyme in isolation and in complex with ubiquitin aldehyde. *Cell*, 111(7): 1041-54 (2002).

(Continued)

*Primary Examiner* — Fred H Reynolds
(74) *Attorney, Agent, or Firm* — Marshall, Gerstein & Borun LLP

(57) ABSTRACT

The present disclosure provides a method of producing enzyme-specific inhibitors or substrate binding partners comprising: identifying active site residues of the substrate in the enzyme substrate complex or in substrate binding partner-substrate complex; randomizing the active site residues to produce a combinatorial library of substrate variants; and selecting substrate variants that inhibit enzyme activity or bind substrate as substrate-specific binding partners. The present disclosure also provides ubiquitin enzyme specific inhibitors and ubiquitin variants that bind ubiquitin interaction motifs.

4 Claims, 26 Drawing Sheets

Specification includes a Sequence Listing.

(56) References Cited

OTHER PUBLICATIONS

Hu et al., Structure and mechanisms of the proteasome-associated deubiquitinating enzyme USP14. *EMBO J.*, 24(21): 3747-56 (2005).
Kawabe et al., Regulation of Rap2A by the ubiquitin ligase Nedd4-1 controls neurite development. *Neuron*, 65(3): 358-72 (2010).
Kirchhoff et al., Ubiquitin genes in trypanosomatidae, *J. Biol. Chem.*, 263(5):12698-704 (1988).
Komander et al., Breaking the chains: structure and function of the deubiquitinases. *Nat. Rev. Molec. Cell Biol.*, 10(8): 550-63 (2009).
Lewis et al., Structural basis for non-covalent interaction between ubiquitin and ubiquitin conjugating enzyme variant human MMS2. *J. Biomolec. NMR*, 34(2): 89-100 (2006).
Li et al., A dynamic role of HAUSP in the p53-Mdm2 pathway. *Molec. Cell*, 13(6): 879-86 (2004).
Li et al., Improving therapeutic efficacy of a complement receptor by structure-based affinity maturation. *J. Biol. Chem.*, 284(51): 35605-11 (2009).
Maspero et al., Structure of the HECT:ubiquitin complex and its role in ubiquitin chain elongation. *EMBO Rep.*, 12(4): 342-9 (2011).
Merrifield, Solid phase peptide synthesis. I. The synthesis of a tetrapeptide. *J. Am. Chem. Assoc.* 85: 2149-54 (1964).
Mizuno et al., Regulation of epidermal growth factor receptor down-regulation by UBPY-mediated deubiquitination at endosomes. *Molec. Biol. Cell*, 16(11): 5163-74 (2005).
Moffat et al., A lentiviral RNAi library for human and mouse genes applied to an arrayed viral high-content screen. *Cell*, 124(6): 1283-98 (2006).
Morgan et al., Chapter 26: Approaches to the discovery of non-peptide ligand for peptide receptors and peptidases. *Ann. Reports Med. Chem.* 24:243-52(1989).
Morita et al., Retrovirus budding. *Annu. Rev. Cell Dev. Biol.*, 20: 395-425 (2004).
Nakagawa et al., Deubiquitylation of histone H2A activates transcriptional initiation via trans-histone cross-talk with H3K4 di- and trimethylation. *Genes Dev.*, 22(1): 37-49 (2008).
Niendorf et al., Essential role of ubiquitin-specific protease 8 for receptor tyrosine kinase stability and endocytic trafficking in vivo. *Molec. Cell. Biol.*, 27(13): 5029-39 (2007).
Nijman et al., A genomic and functional inventory of deubiquitinating enzymes. *Cell*, 123(5): 773-86 (2005).
Nijman et al., The deubiquitinating enzyme USP1 regulates the Fanconi anemia pathway. *Molec. Cell*, 17(3): 331-9 (2005).
Pearce et al., Mutational analysis of thrombopoietin for identification of receptor and neutralizing antibody sites. *J. Biol. Chem.*, 272(33): 20595-602 (1997).
Priolo et al., The isopeptidase USP2a protects human prostate cancer from apoptosis. *Cancer Res.*, 66(17): 8625-32 (2006).
Ren et al., VHS domains of ESCRT-0 cooperate in high-avidity binding to polyubiquitinated cargo. *EMBO J.* 29(6): 1045-54 (2010).
Renatus et al., Structural basis of ubiquitin recognition by the deubiquitinating protease USP2. *Structure*, 14(8): 1293-302 (2006).
Reyes-Turcu et al., Regulation and cellular roles of ubiquitin-specific deubiquitinating enzymes. *Ann. Rev. Biochem.*, 78:363-97 (2009).
Saggar et al., CYLD mutations in familial skin appendage tumours. *J. Med. Genet.*, 45(5): 298-302 (2008).
Schnell et al., Non-traditional functions of ubiquitin and ubiquitin-binding proteins, *J. Biol. Chem.*, 278:(38)35857-60 (2003).
Sidhu et al., Phage display for selection of novel binding peptides. *Meth. Enzymol.*, 328: 333-63 (2000).
Sidhu et al., Phage-displayed antibody libraries of synthetic heavy chain complementarity determining regions. *J. Molec. Biol.*, 338(2): 299-310 (2004).
Simon et al., Peptoids: a modular approach to drug discovery. *Proc. Natl. Acad. Sci. USA*, 89: 9367-71 (1972).
Stevenson et al., The deubiquitinating enzyme USP2a regulates the p53 pathway by targeting Mdm2. *EMBO J.*, 26(4): 976-986 (2007).
Tao et al., ITCH K63-ubiquitinates the NOD2 binding protein, RIP2, to influence inflammatory signaling pathways. *Curr. Biol.*, 19(15): 1255-63 (2009).
Tonikian et al., Identifying specificity profiles for peptide recognition modules from phage-displayed peptide libraries. *Nat. Protoc.*, 2(6): 1368-86 (2007).
Ventii et al., Protein partners of deubiquitinating enzymes. *Biochem. J.*, 414: 161-75 (2008).
Walker eta I., The catalytic domain of USP8 in complex with USP8 specific inhibitor. EBI Database accession No. 3n3k, Jun. 23, 2010.
Walker eta I., Usp21 in complex with a ubiquitin-based, USP21-specific inhibitor. EBI Database accession No. 3mtn, Jun. 9, 2010.
Wilkinson et al., Regulation of ubiquitin-dependent processes by deubiquitinating enzymes. *FASEB J.*, 11(14): 1245-56 (1997).
Wollert et al., Molecular mechanism of multivesicular body biogenesis by ESCRT complexes. *Nature*, 464(7290): 864-9 (2010).
Xu et al., High-level expression of the recombinant hybrid peptide cecropinA(1-8)-magainin2(1-12) with an ubiquitin fusion partner in *Escherichia coli. Protein Express. Purific.* 55(1): 175-82 (2007).
Xu et al., Ubiquitin-specific Peptidase 21 Inhibits Tumor Necrosis Factor alpha-induced Nuclear Factor kappa B Activation via Binding to and Deubiquitinating Receptor-interacting Protein 1. *J. Biol. Chem.*, 285(2): 969-78 (2010).
Yampolsky et al., The exchangeability of amino acids in proteins, *Genetics*, 170:1459-72 (2005).
Ye et al., Building ubiquitin chains: E2 enzymes at work. *Nat. Rev. Molec. Cell Biol.*, 10(11): 755-64 (2009).
Yim et al., Rak functions as a tumor suppressor by regulating PTEN protein stability and function. *Cancer Cell*, 15(4): 304-14 (2009).
Yuan et al., USP10 regulates p53 localization and stability by deubiquitinating p53. *Cell*, 140(3): 384-96 (2010).
Zhang et al., A new strategy for the synthesis of glycoproteins. *Science*, 303(5656): 371-3 (2004).
Zhang et al., A role for the deubiquitinating enzyme USP28 in control of the DNA-damage response. *Cell*, 126(3): 529-42 (2006).
Zhang et al., The putative cancer stem cell marker USP22 is a subunit of the human SAGA complex required for activated transcription and cell-cycle progression. *Molec. Cell*, 29(1): 102-11 (2008).

SEQ ID NO: 1

| Ub variant | Target | 2 | 4 | 6 | 8 | 9 | 10 | 11 | 12 | 14 | 35 | 37 | 39 | 40 | 42 | 44 | 46 | 47 | 48 | 49 | 62 | 63 | 64 | 66 | 68 | 70 | 71 | 72 | SEQ ID NO |
|---|---|---|---|---|---|---|---|---|---|---|---|---|---|---|---|---|---|---|---|---|---|---|---|---|---|---|---|---|---|
| Wt | | Q | F | K | L | T | G | K | T | T | G | P | D | Q | R | I | A | G | K | Q | Q | K | E | T | H | V | L | R | 1 |
| | Region 1 | | | | | | | | | | Region 2 | | | | | | | | | | Region 3 | | | | | | | | |
| 8.2 | USP8 | R | V | - | M | - | R | - | - | - | - | - | - | - | - | - | - | - | - | - | H | N | H | A | Y | L | - | K | 2 |
| 8.3 | USP21 | Y | - | F | M | - | R | - | Y | - | - | - | - | - | - | - | - | - | - | - | S | - | V | A | Y | L | F | - | 3 |
| 21.1 | USP21 | - | - | - | - | - | - | - | - | - | - | - | - | - | - | - | - | - | - | - | - | - | I | - | F | L | M | - | 4 |
| 21.2 | USP21 | - | - | - | - | - | - | - | - | - | - | - | - | - | - | - | - | - | - | - | L | - | R | - | F | L | - | K | 5 |
| 21.3 | USP21 | - | - | - | G | - | - | - | - | - | - | - | - | - | - | - | - | - | - | - | L | - | S | - | F | L | - | - | 6 |
| 21.4 | USP21 | - | - | - | - | - | - | - | - | - | - | - | - | - | - | - | - | - | - | - | - | - | W | - | F | L | - | - | 7 |
| 21.5 | USP21 | - | - | - | - | - | - | - | - | - | - | - | - | - | - | - | - | - | - | - | - | - | D | - | F | L | - | - | 8 |

Figure 2A

| 2 | 6 | 8 | 9 | 10 | 11 | 12 | 62 | 63 | 64 | 68 | 70 | 71 | 74 | 75 | 76 | 76a | 76b | Position* | Lead** | SEQ ID NO |
|---|---|---|---|---|---|---|---|---|---|---|---|---|---|---|---|---|---|---|---|---|
| Q | K | L | T | G | K | T | Q | K | E | H | V | L | R | G | G | G | G | Ub.wt | | 21 |
| - | - | - | - | - | - | - | - | - | - | - | - | M | W | S | H | R | G | USP2-A1 | | 22 |
| - | N | - | W | T | Q | N | - | - | - | - | - | - | W | S | E | - | T | USP2-A10 | | 23 |
| - | M | - | - | - | - | - | - | - | - | - | - | - | L | S | - | - | H | USP2-A12 | | 24 |
| - | - | - | - | - | R | - | - | - | Y | - | - | - | Y | - | V | K | R | USP2-A3 | | 25 |
| - | - | - | - | - | - | - | - | - | - | - | - | - | - | - | Q | A | A | USP2-A6 | | 26 |
| D | N | I | - | - | - | - | - | P | R | Y | - | - | L | - | E | I | Q | USP2-A7 | | 27 |
| - | M | - | - | - | - | - | - | - | - | - | - | - | L | - | V | S | H | USP2-A9 | | 28 |
| - | Y | - | - | - | - | - | - | - | - | - | - | - | Y | S | L | D | R | USP2-B10 | | 29 |
| H | - | - | - | - | - | - | - | - | - | - | - | - | - | - | - | - | - | USP2-B11 | | 30 |
| - | N | - | S | - | R | H | - | - | - | - | - | - | L | S | C | R | K | USP2-B12 | | 31 |
| - | N | - | - | - | T | - | - | - | - | - | - | - | W | S | N | K | - | USP2-B7 | Ubv.02.01 | 32 |
| - | M | - | - | - | - | H | - | - | - | - | - | - | L | S | - | R | K | USP2-B8 | Ubv.02.02 | 33 |
| - | - | I | A | - | - | A | - | - | - | - | - | - | H | - | N | A | M | USP2-C10 | | 34 |
| - | - | A | S | - | - | H | - | - | - | - | - | - | L | S | - | K | R | USP2-C11 | | 35 |
| - | N | - | - | - | - | - | - | - | - | - | - | - | - | - | - | - | - | USP2-C3 | Ubv.02.03 | 36 |
| - | N | - | - | - | - | - | - | - | - | - | - | - | F | S | A | R | V | USP2-C5 | | 37 |
| - | - | - | - | - | - | - | - | - | - | - | - | - | - | - | - | - | - | USP2-C7 | Ubv.02.04 | 38 |
| - | N | - | - | - | - | - | H | - | - | - | - | - | L | S | - | R | R | USP2-C8 | | 39 |
| - | N | - | - | - | - | - | K | - | - | - | - | - | W | S | W | R | R | USP2-C9 | | 40 |
| - | N | - | - | A | R | N | - | - | - | - | - | - | - | S | E | N | L | USP2-D1 | | 41 |
| - | - | - | - | - | - | - | - | - | - | - | - | - | L | S | - | S | - | USP2-D11 | | 42 |
| D | N | - | - | - | N | - | - | - | - | F | - | - | W | S | I | S | - | USP2-D3 | Ubv.02.05 | 43 |
| E | - | - | - | - | - | - | - | - | - | - | - | - | - | - | - | - | F | USP2-D4 | | 44 |
| - | - | - | - | - | - | - | - | - | - | - | - | - | L | S | R | S | K | USP2-D6 | | 45 |
| - | A | - | - | - | - | - | - | - | - | - | - | - | L | - | Y | S | - | USP2-D7 | | 46 |
| - | N | - | A | - | N | H | - | - | - | - | - | - | L | - | - | - | - | USP2-D9 | Ubv.02.06 | 47 |

\* Positions in ubiquitin without mutations are not shown
\*\* Lead candidates with affinity 25 nM or better.

Figure 5A

Ubvs with binding specificity to USP5

| 2 | 4 | 6 | 8 | 9 | 10 | 11 | 12 | 14 | 42 | 46 | 47 | 48 | 49 | 62 | 63 | 64 | 68 | 70 | 71 | 73 | 74 | 75 | 76 | 77 | 78 | Position* | SEQ ID NO |
|---|---|---|---|---|----|----|----|----|----|----|----|----|----|----|----|----|----|----|----|----|----|----|----|----|----|-----------|-----------|
| Q | F | K | L | T | G | K | T | T | R | A | G | K | Q | Q | K | E | H | V | L | L | R | G | Q | G | G | Ub.wt | 21 |
| E | Y | N | R | L | L | E | T | N | - | - | - | - | - | - | - | K | Y | L | - | - | L | - | Q | R | H | USP5-E4 | 48 |
| - | - | Q | R | V | M | N | S | - | T | - | - | - | - | H | - | D | - | L | - | M | - | R | L | N | K | USP5-F11 | 49 |
| - | - | - | R | A | M | W | T | R | - | - | - | - | - | P | - | - | - | - | - | - | - | - | - | - | - | USP5-F3 | 50 |
| - | - | N | R | - | M | F | S | F | - | - | - | Q | - | - | - | - | - | - | - | - | - | - | - | - | - | USP5-F7 | 51 |
| R | - | - | R | M | M | E | - | - | - | D | R | - | - | - | - | - | - | - | F | - | - | S | A | R | R | USP5-F8 | 52 |
| P | - | N | R | W | N | - | S | P | - | - | - | - | - | - | - | - | - | V | - | D | L | - | V | F | C | USP5-F9 | 53 |
| - | M | H | R | V | M | N | - | - | - | - | - | - | - | - | - | - | - | - | - | - | - | - | - | - | - | USP5-G10 | 54 |
| - | S | N | R | M | M | E | S | - | - | - | - | - | - | L | P | - | - | - | - | - | - | - | - | - | - | USP5-G11 | 55 |
| - | V | - | R | - | M | E | - | - | - | - | - | - | - | - | - | - | - | - | - | - | - | - | - | - | - | USP5-G3 | 56 |
| - | - | N | R | I | M | - | - | Q | - | - | - | - | - | - | - | - | - | - | - | - | - | - | - | - | - | USP5-G4 | 57 |
| H | S | N | R | S | M | W | - | - | - | - | - | - | - | H | - | - | - | - | - | - | - | - | - | - | - | USP5-G5 | 58 |
| H | - | H | R | M | M | E | - | A | - | - | - | - | - | - | R | - | - | - | - | - | - | - | - | - | - | USP5-G6 | 59 |
| - | - | I | R | A | M | W | - | - | - | - | - | - | - | - | T | - | - | - | - | - | - | - | - | - | - | USP5-G8 | 60 |
| - | - | R | R | M | M | D | S | M | - | - | - | - | - | - | - | - | - | - | - | - | - | - | - | - | - | USP5-G9 | 61 |
| - | - | N | R | M | M | M | - | - | - | - | - | N | - | - | - | - | - | - | - | - | - | - | - | - | - | USP5-H10 | 62 |
| - | V | N | R | S | M | N | - | H | - | - | - | - | - | H | - | R | Y | - | - | - | - | - | - | - | - | USP5-H11 | 63 |
| R | V | N | R | Y | M | N | - | S | - | - | - | - | - | - | - | - | - | - | - | - | - | - | - | - | - | USP5-H12 | 64 |
| - | - | N | R | L | M | Y | S | - | - | - | - | - | - | - | - | - | - | - | - | I | S | R | A | R | - | USP5-H4 | 65 |
| - | L | R | R | I | M | E | - | A | - | - | - | - | R | - | - | S | - | - | - | - | - | - | - | - | - | USP5-H7 | 66 |
| - | - | N | R | M | M | N | - | S | - | - | - | - | - | - | - | - | - | - | - | - | - | - | - | - | - | USP5-H8 | 67 |
| - | - | - | R | M | M | N | - | D | - | - | - | - | - | - | - | - | - | - | - | - | - | - | - | - | - | USP5-H9 | 68 |

*Positions in ubiquitin without mutations are not shown

Figure 6A

USP10 bindig Ubv

| 6 | 8 | 9 | 14 | 44 | 46 | 49 | 63 | 64 | 68 | 70 | 71 | 74 | 75 | 76 | 77 | 78 | Positions* | SEQ ID NO |
|---|---|---|----|----|----|----|----|----|----|----|----|----|----|----|----|----|------------|-----------|
| K | L | T | T | I | A | Q | K | E | H | V | L | R | G | G | G | G | Ub.wt | 21 |
| E | P | M | A | V | V | L | R | W | A | K | F | L | A | K | N | L | Ubv.10.1 | 69 |

*Positions in ubiquitin without mutations are not shown.

Ubvs with binding specificity for USP48

| 2 | 4 | 6 | 9 | 11 | 12 | 14 | 44 | 46 | 47 | 48 | 49 | 62 | 63 | 64 | 68 | 70 | 73 | 74 | 76 | 77 | 78 | Position* | SEQ ID NO |
|---|---|---|---|----|----|----|----|----|----|----|----|----|----|----|----|----|----|----|----|----|----|-----------|-----------|
| Q | F | K | T | K  | T  | I  | A  | G  | K  | Q  | Q  | K  | E  | H  | V  | L  | R  | G  | G  | G  | Ub.wt     | 21        |
| - | - | - | G | -  | -  | G  | F  | -  | W  | T  | P  | -  | M  | -  | R  | F  | P  | -  | L  | K  | E  | Ubv.48.01 | 70        |
| S | - | - | N | M  | -  | T  | V  | -  | F  | -  | -  | G  | -  | H  | -  | W  | -  | L  | I  | -  | K  | Ubv.48.02 | 71        |
| - | - | N | N | N  | -  | I  | S  | F  | -  | W  | -  | P  | -  | P  | F  | -  | -  | -  | -  | -  | -  | Ubv.48.03 | 72        |
| S | - | - | G | -  | -  | -  | F  | -  | F  | T  | P  | G  | -  | Q  | -  | W  | -  | L  | E  | E  | E  | Ubv.48.04 | 73        |
| R | - | E | - | Q  | -  | N  | N  | -  | -  | -  | L  | K  | -  | W  | -  | -  | -  | -  | -  | -  | -  | Ubv.48.05 | 74        |

*Positions in ubiquitin without mutations are not shown

Figure 8A

Nedd4 binders.

| 2 | 4 | 6 | 8 | 9 | 10 | 11 | 12 | 14 | 42 | 44 | 46 | 47 | 48 | 49 | 62 | 63 | 64 | 68 | 70 | 71 | 72 | 73 | 74 | 75 | 76 | 77 | 78 | Positions | SEQ ID NO |
|---|---|---|---|---|----|----|----|----|----|----|----|----|----|----|----|----|----|----|----|----|----|----|----|----|----|----|----|-----------|-----------|
| Q | F | K | L | T | G  | K  | T  | T  | R  | I  | A  | G  | K  | Q  | Q  | K  | E  | H  | V  | L  | R  | L  | R  | G  | G  | G  | G  | Ub.wt     | 21        |
| L | - | - | - | H | S  | -  | -  | F  | -  | -  | -  | -  | H  | -  | -  | F  | -  | -  | -  | K  | -  | -  | -  | -  | R  | W  | K  | N4-A11    | 75        |
| R | T | R | A | - | -  | -  | -  | -  | -  | T  | -  | -  | K  | P  | Y  | -  | -  | -  | -  | K  | -  | -  | -  | M  | E  | Q  | -  | N4-A9*    | 76        |
| H | R | - | - | R | -  | I  | -  | -  | F  | T  | -  | -  | M  | T  | -  | -  | -  | -  | -  | -  | -  | -  | -  | -  | -  | -  | -  | N4-B1*    | 77        |
| R | L | - | - | R | -  | V  | -  | -  | Q  | R  | -  | -  | -  | -  | -  | -  | -  | -  | -  | -  | -  | -  | -  | -  | -  | -  | -  | N4-B10    | 78        |
| - | - | M | R | R | E  | S  | -  | G  | -  | -  | -  | -  | -  | -  | -  | -  | -  | -  | -  | -  | -  | P  | -  | -  | R  | Q  | Y  | N4-B4     | 79        |
| V | - | S | R | - | -  | -  | -  | -  | -  | -  | -  | -  | K  | -  | -  | -  | -  | A  | -  | K  | -  | P  | -  | M  | -  | -  | -  | N4-B5*    | 80        |
| - | F | - | - | - | -  | -  | -  | -  | -  | -  | D  | R  | N  | K  | K  | -  | G  | -  | -  | -  | -  | -  | -  | -  | -  | -  | -  | N4-B6*    | 81        |
| L | Q | R | - | - | -  | -  | -  | -  | F  | -  | -  | -  | T  | -  | -  | H  | Y  | -  | -  | -  | -  | L  | P  | -  | R  | R  | H  | N4-C1*    | 82        |
| - | - | - | - | - | -  | -  | -  | -  | -  | -  | -  | -  | L  | K  | -  | V  | -  | Y  | -  | K  | T  | F  | P  | -  | R  | R  | Q  | N4-C10    | 83        |
| - | L | - | - | A | -  | W  | G  | -  | -  | -  | -  | -  | -  | -  | R  | Y  | D  | -  | -  | -  | G  | -  | -  | -  | -  | -  | -  | N4-C11*   | 84        |
| - | - | - | - | A | R  | T  | S  | I  | -  | -  | -  | -  | -  | -  | -  | -  | -  | -  | -  | -  | -  | -  | -  | -  | -  | -  | -  | N4-C12    | 85        |
| - | - | - | - | - | -  | -  | -  | -  | -  | -  | -  | -  | -  | -  | -  | D  | -  | -  | -  | R  | -  | -  | P  | R  | M  | -  | K  | N4-C2*    | 86        |
| Y | S | - | R | E | S  | -  | -  | -  | S  | K  | F  | -  | -  | I  | L  | W  | -  | -  | -  | K  | -  | -  | -  | A  | V  | H  | M  | N4-C4     | 87        |
| - | - | - | - | - | -  | -  | -  | -  | -  | -  | -  | -  | R  | -  | -  | -  | -  | -  | -  | -  | -  | -  | -  | -  | -  | -  | -  | N4-C5     | 88        |
| P | V | A | R | Y | -  | -  | -  | -  | -  | K  | F  | N  | -  | -  | -  | G  | Y  | -  | -  | K  | -  | -  | -  | -  | -  | -  | -  | N4-C6     | 89        |
| - | - | A | R | T | S  | S  | S  | K  | -  | -  | -  | -  | N  | R  | H  | N  | G  | Y  | -  | K  | -  | -  | P  | T  | K  | R  | V  | N4-D1     | 90        |
| - | R | M | R | - | -  | -  | -  | -  | -  | -  | -  | -  | L  | -  | -  | -  | -  | -  | -  | K  | -  | I  | L  | L  | R  | E  | -  | N4-D10    | 91        |
| - | - | - | - | - | -  | -  | -  | -  | -  | -  | -  | -  | -  | -  | -  | -  | -  | -  | -  | K  | K  | -  | -  | -  | -  | -  | -  | N4-D11*   | 92        |
| Y | - | R | - | - | -  | S  | -  | -  | -  | K  | -  | -  | -  | -  | Y  | Y  | -  | -  | -  | -  | -  | -  | -  | -  | -  | -  | -  | N4-D12    | 93        |
| Y | S | R | - | - | -  | -  | -  | -  | -  | F  | R  | -  | P  | K  | -  | -  | -  | Y  | -  | Y  | -  | -  | -  | -  | K  | Q  | -  | N4-D2     | 94        |
| - | - | - | A | N | -  | -  | -  | -  | -  | -  | -  | F  | -  | -  | -  | -  | -  | -  | -  | W  | -  | F  | S  | R  | L  | M  | -  | N4-D3*    | 95        |
| K | S | N | - | - | -  | -  | -  | -  | -  | -  | -  | -  | -  | -  | -  | -  | G  | L  | -  | R  | -  | -  | R  | S  | L  | K  | Q  | N4-D5     | 96        |
| - | - | - | - | - | -  | -  | -  | -  | -  | -  | -  | -  | -  | -  | -  | -  | -  | -  | -  | K  | -  | -  | -  | -  | L  | V  | S  | N4-D8*    | 97        |
| - | P | V | Q | - | -  | -  | -  | -  | -  | -  | -  | K  | Q  | -  | L  | -  | V  | Q  | -  | -  | -  | -  | -  | -  | -  | -  | -  | N4-D9*    | 98        |

Sequence of ITCH binding Ubvs

| | 2 | 4 | 6 | 8 | 9 | 10 | 11 | 12 | 14 | 42 | 44 | 46 | 47 | 48 | 49 | 62 | 63 | 64 | 68 | 70 | 71 | 72 | 73 | 74 | 75 | 76 | 77 | 78 | Positions | SEQ ID NO |
|---|---|---|---|---|---|---|---|---|---|---|---|---|---|---|---|---|---|---|---|---|---|---|---|---|---|---|---|---|---|---|
| | Q | F | K | L | T | G | K | T | T | R | I | A | G | K | Q | Q | K | E | H | V | L | R | L | R | G | G | | | Ub.wt | 21 |
| | P | L | - | R | - | - | - | Q | S | I | F | - | R | - | H | - | - | R | Y | F | - | F | H | - | M | V | A | | Ubv.ITCH.01 | 99 |
| | H | L | - | - | - | W | R | - | - | - | - | L | G | - | N | K | - | - | Y | L | - | - | R | L | - | S | K | F | Ubv.ITCH.02 | 100 |
| | - | - | H | - | - | - | - | - | - | - | - | L | - | R | Q | K | - | D | - | - | - | I | R | - | V | S | K | R | Ubv.ITCH.03 | 101 |
| | - | - | - | - | - | - | L | S | - | I | - | G | - | - | R | - | - | K | Y | L | M | - | - | - | V | S | R | R | Ubv.ITCH.04 | 102 |
| | - | - | - | - | - | T | D | - | I | L | - | - | - | - | - | P | G | D | Y | L | M | - | F | G | N | K | R | R | Ubv.ITCH.05 | 103 |
| | P | L | Q | - | R | - | - | Q | S | I | F | - | R | T | H | - | - | - | G | Y | L | - | F | H | - | T | V | A | Ubv.ITCH.06 | 104 |

| | 2 | 4 | 6 | 8 | 9 | 10 | 11 | 12 | 14 | 42 | 44 | 46 | 47 | 48 | 49 | 62 | 63 | 64 | 68 | 70 | 71 | 72 | 73 | 74 | 75 | 76 | 77 | 78 | Positions | SEQ ID NO |
|---|---|---|---|---|---|---|---|---|---|---|---|---|---|---|---|---|---|---|---|---|---|---|---|---|---|---|---|---|---|---|
| Sequences of UIM binders | | | | | | | | | | | | | | | | | | | | | | | | | | | | | | |
| | Q | F | K | L | T | G | K | T | T | R | I | A | G | K | Q | Q | K | E | H | V | L | R | L | R | G | G | G | G | Ub.wt | 21 |
| | - | L | - | - | V | V | - | - | S | - | - | - | - | M | - | R | R | A | - | - | G | - | - | - | - | - | - | - | Ubv.UIM1.01 | 105 |
| | - | - | Q | - | - | I | - | - | I | - | Y | - | - | Y | - | G | M | - | R | - | G | - | - | - | - | - | - | - | Ubv.UIM1.02 | 106 |
| | P | S | V | - | I | V | - | - | S | - | - | - | - | - | - | N | R | - | - | - | G | - | - | - | - | - | - | - | Ubv.UIM1.03 | 107 |
| | L | - | T | V | R | V | S | - | - | - | - | - | - | M | - | L | - | K | - | - | W | I | F | - | - | N | R | T | Ubv.UIM1.04 | 108 |
| | - | L | - | V | - | V | - | - | S | - | - | - | - | - | - | R | R | A | - | - | G | - | - | - | - | - | - | - | Ubv.UIM1a.01 | 109 |
| | E | V | Q | - | I | - | - | - | - | - | - | G | - | D | F | - | H | - | L | - | S | W | - | - | - | - | - | - | Ubv.UIM1a.02 | 110 |
| | - | - | E | I | - | V | - | - | A | - | - | - | - | - | - | - | - | - | - | - | S | W | - | H | - | D | R | Q | Ubv.UIM1a.03 | 111 |
| | - | - | Q | - | - | V | M | R | I | - | Y | G | - | M | - | G | M | - | R | - | G | S | - | - | - | - | - | - | Ubv.UIM1a.04 | 112 |
| | - | - | Q | - | - | V | - | - | A | - | - | - | - | - | - | - | K | R | D | Y | S | S | - | - | S | L | R | A | Ubv.UIM1a.05 | 113 |
| | - | - | - | - | - | V | - | - | S | - | - | - | - | R | - | - | - | G | - | - | A | W | - | - | - | - | - | - | Ubv.UIM1a.06 | 114 |
| | R | - | - | - | - | - | - | S | H | - | - | - | - | - | L | - | - | - | - | - | A | K | H | - | - | M | E | V | Ubv.UIM1b.01 | 115 |
| | - | - | - | F | S | V | - | T | Y | - | - | - | - | - | - | K | - | - | - | - | - | K | F | - | A | L | V | R | Ubv.UIM1b.02 | 116 |
| | - | - | - | - | - | V | R | - | - | N | - | - | - | R | - | - | Q | - | - | - | - | S | - | - | - | T | R | E | Ubv.UIM1b.03 | 117 |
| | - | N | - | - | A | V | E | - | E | - | - | G | - | - | - | - | - | D | G | - | S | V | - | - | V | L | R | R | Ubv.UIM1b.04 | 118 |
| | - | - | - | M | V | - | - | - | - | - | F | - | A | - | - | - | - | D | G | - | Y | S | - | - | - | - | - | Q | Ubv.UIM1b.05 | 119 |
| | L | - | - | R | V | E | - | A | - | - | - | G | - | Q | - | G | - | - | - | - | F | T | - | - | V | Y | E | S | Ubv.UIM1b.06 | 120 |
| | T | - | - | - | I | - | - | - | - | - | - | - | - | - | - | - | - | - | R | - | T | - | H | - | R | T | V | K | Ubv.UIM1b.07 | 121 |
| | H | - | - | - | - | V | - | - | - | - | - | V | R | Q | H | - | - | - | G | - | S | - | - | - | - | I | A | K | Ubv.UIM1b.08 | 122 |
| | - | G | - | - | - | V | N | G | N | - | F | - | - | - | - | - | - | - | - | - | - | - | - | - | - | - | - | - | Ubv.UIM1b.09 | 123 |
| | - | - | - | - | - | V | N | - | K | - | - | S | - | - | E | - | N | K | Y | - | - | - | - | - | - | K | - | Q | Ubv.UIM1b.10 | 124 |
| | L | T | - | - | - | V | R | - | L | - | L | - | - | Q | - | - | - | - | - | - | A | S | - | - | - | D | Q | K | Ubv.UIM1b.11 | 125 |
| | - | N | - | R | - | A | F | - | - | - | - | - | - | - | H | - | - | - | S | - | - | - | - | - | - | D | - | - | Ubv.UIM1b.12 | 126 |
| | - | S | - | K | W | - | - | - | A | - | - | S | - | W | H | - | - | G | G | - | - | - | - | - | - | - | - | - | Ubv.UIM1b.13 | 127 |
| | E | - | - | A | V | - | - | - | - | F | - | - | - | - | - | - | - | - | - | G | V | M | - | - | I | Y | R | A | Ubv.UIM1b.14 | 128 |
| | K | - | T | - | - | V | - | - | A | G | - | - | - | - | - | - | - | - | L | - | - | - | - | - | A | N | R | S | Ubv.UIM1b.15 | 129 |

Figure 11A

Sequences of USP8 binders

| 6 | 8 | 9 | 11 | 12 | 14 | 42 | 44 | 46 | 47 | 49 | 62 | 63 | 64 | 68 | 70 | 71 | 72 | 73 | 74 | 75 | 76 | 77 | 78 | Positions | SEQ ID NO |
|---|---|---|---|---|---|---|---|---|---|---|---|---|---|---|---|---|---|---|---|---|---|---|---|---|---|
| K | L | T | K | T | T | R | I | A | G | Q | Q | K | E | H | V | L | R | L | R | G | G | G | G | Ub.wt | 21 |
| . | P | K | . | N | . | . | . | I | A | H | P | . | . | S | L | M | S | F | P | R | T | V | R | USP8-A01 | 130 |
| . | . | R | H | L | . | . | . | V | A | . | H | . | T | Q | M | F | K | P | . | . | Q | R | R | USP8-A03 | 131 |
| . | . | . | . | . | . | . | S | . | . | P | H | R | T | . | F | . | S | F | . | S | R | V | K | USP8-A04 | 132 |
| . | . | . | . | . | . | . | S | . | . | . | H | R | . | . | . | F | . | F | . | . | K | V | K | USP8-A06 | 133 |
| . | . | R | . | . | . | . | F | D | V | . | . | . | . | D | F | . | G | . | . | . | R | D | R | USP8-A07 | 134 |
| . | . | . | . | . | . | . | . | S | . | P | P | . | . | D | G | . | R | R | . | T | T | V | S | USP8-A08 | 135 |
| . | . | . | . | . | . | K | Y | . | V | . | N | W | . | R | W | S | . | V | . | . | K | Y | Q | USP8-A09 | 136 |
| . | V | K | E | . | V | . | . | D | V | . | . | Q | . | . | L | V | . | . | G | . | R | . | . | USP8-B03 | 137 |
| . | F | P | . | A | . | . | L | D | . | . | . | N | . | N | . | W | . | P | . | . | V | L | N | USP8-B06 | 138 |
| I | . | . | . | . | . | . | . | D | V | . | . | T | Y | . | G | . | . | . | . | . | H | T | T | USP8-B09 | 139 |
| . | . | M | R | A | . | . | . | . | . | . | H | . | A | Y | M | . | . | . | . | . | . | . | . | USP8-B10 | 140 |

Figure 12A

| 2 | 6 | 8 | 9 | 10 | 11 | 12 | 14 | 62 | 63 | 64 | 68 | 70 | 71 | 72 | 73 | 74 | 75 | 76 | 77 | 78 | | SEQ ID NO 21 |
|---|---|---|---|----|----|----|----|----|----|----|----|----|----|----|----|----|----|----|----|----|---|---|
| Q | K | L | T | G | K | T | T | Q | K | E | H | V | L | R | - | - | G | G | G | G | | |
| - | - | - | - | - | - | - | - | E | W | K | F | L | - | - | - | - | S | I | L | L | USP21-E10 | 141 |
| - | - | - | - | - | - | - | - | P | - | - | F | V | - | - | - | - | F | V | Q | I | USP21-E11 | 142 |
| - | - | - | - | - | - | - | - | E | T | G | F | L | - | - | - | - | - | M | - | T | USP21-E12 | 143 |
| - | - | - | - | - | - | - | - | - | Y | H | F | L | V | K | F | - | S | Y | M | R | USP21-E2 | 144 |
| - | - | - | - | - | - | - | - | P | N | - | F | L | - | K | F | - | - | L | T | P | USP21-E3 | 145 |
| - | - | - | - | - | - | - | - | - | - | A | F | L | - | - | F | - | P | V | Q | A | USP21-E4 | 146 |
| - | - | - | - | - | - | - | - | - | - | - | F | L | - | - | - | H | A | Q | R | R | USP21-E6 | 147 |
| - | - | - | - | - | - | - | - | - | - | F | F | L | - | - | - | G | - | W | Y | L | USP21-E7 | 148 |
| - | - | - | - | - | - | - | - | - | - | Q | F | Y | - | - | - | - | - | K | D | M | USP21-E9 | 149 |
| - | - | - | - | - | - | - | - | - | - | R | Q | L | L | - | I | H | R | R | K | R | USP21-F11 | 150 |
| - | - | - | - | - | - | - | - | - | - | H | Y | L | F | - | F | T | V | K | - | R | USP21-F12 | 151 |
| - | - | - | - | - | - | - | - | - | - | R | H | F | L | - | - | - | D | T | S | R | USP21-F2 | 152 |
| - | - | - | - | - | - | - | - | - | - | A | A | F | - | - | - | V | A | H | K | Q | USP21-F3 | 153 |
| E | - | S | - | M | - | - | - | H | - | H | H | F | - | - | - | H | V | - | N | N | USP21-F5 | 154 |
| - | - | V | - | - | - | - | - | - | - | K | F | L | - | - | F | - | H | S | R | E | USP21-F6 | 155 |
| - | - | V | - | - | - | R | S | - | T | - | K | L | - | - | - | H | - | T | L | S | USP21-F9 | 156 |
| - | - | - | - | - | - | - | - | E | - | - | F | F | - | - | F | - | P | N | T | R | USP21-G11 | 157 |
| - | - | - | P | - | - | - | - | H | L | R | F | L | - | - | - | P | S | W | K | - | USP21-G2 | 158 |
| - | Y | - | - | - | - | - | - | E | - | K | F | L | - | - | - | Y | R | L | Y | K | USP21-G3 | 159 |
| - | - | - | - | - | - | - | - | - | - | K | F | L | A | - | - | Y | W | E | D | K | USP21-G4 | 160 |
| - | - | - | - | - | - | - | - | - | Y | - | F | L | W | - | - | - | F | - | R | A | USP21-G5 | 161 |
| - | - | - | - | - | - | - | - | Y | N | - | F | I | - | K | - | T | S | A | M | V | USP21-G6 | 162 |
| - | - | - | A | - | - | - | - | - | R | - | F | L | F | - | - | - | - | N | T | L | USP21-G9 | 163 |
| - | - | S | - | - | - | - | - | N | L | V | F | L | - | - | - | T | R | R | S | M | USP21-H1 | 164 |
| - | - | - | - | - | - | - | - | - | - | - | F | L | - | - | - | S | W | D | F | K | USP21-H3 | 165 |
| - | - | - | - | - | - | - | - | - | - | H | F | L | F | K | - | W | - | R | L | K | USP21-H5 | 166 |
| - | - | - | - | - | - | - | - | - | - | - | F | L | - | - | - | - | - | S | Q | K | USP21-H6 | 167 |
| - | - | H | - | - | M | - | - | V | - | N | F | L | - | - | I | H | - | L | S | S | USP21-H7 | 168 |
| - | - | P | - | - | - | - | - | - | - | D | F | L | - | - | - | - | L | L | Q | Y | USP21-H8 | 169 |

Figure 13A

```
SEQUENCE LISTING

<160> NUMBER OF SEQ ID NOS: 173

<210> SEQ ID NO 1
<211> LENGTH: 76
<212> TYPE: PRT
<213> ORGANISM: Homo sapiens
<220> FEATURE:
<221> NAME/KEY: MISC_FEATURE
<223> OTHER INFORMATION: Ubiquitin wildtype

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 8.2

<400> SEQUENCE: 2

Met Arg Ile Val Val Lys Thr Leu Met Gly Arg Thr Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Asn His
    50                  55                  60

Ser Ala Leu Tyr Leu Leu Leu Lys Leu Arg Gly Gly
65                  70                  75

<210> SEQ ID NO 3
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 8.3
```

<400> SEQUENCE: 3

Met Tyr Ile Phe Val Lys Thr Phe Met Gly Arg Thr Ile Tyr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Ser Lys Val
        50                  55                  60

Ser Ala Leu Tyr Leu Leu Phe Arg Leu Arg Gly Gly
65                  70                  75

<210> SEQ ID NO 4
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 21.1

<400> SEQUENCE: 4

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Ile
        50                  55                  60

Ser Thr Leu Phe Leu Leu Met Arg Leu Arg Gly Gly
65                  70                  75

<210> SEQ ID NO 5
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 21.2

<400> SEQUENCE: 5

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Leu Lys Arg
        50                  55                  60

Ser Thr Leu Phe Leu Leu Leu Lys Leu Arg Gly Gly
65                  70                  75

<210> SEQ ID NO 6
<211> LENGTH: 76
<212> TYPE: PRT
<213> ORGANISM: Artificial Sequence
<220> FEATURE:

<223> OTHER INFORMATION: Synthetic peptide
<220> FEATURE:
<221> NAME/KEY: MISC_FEATURE
<223> OTHER INFORMATION: Ubiquitin variant 21.3

<400> SEQUENCE: 6

Met Gln Ile Phe Val Lys Thr Gly Thr Gly Lys Thr Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Leu Lys Ser
    50                  55                  60

Ser Thr Leu Phe Leu Leu Leu Arg Leu Arg Gly Gly
65                  70                  75

<210> SEQ ID NO 7
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 21.4

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Trp
    50                  55                  60

Ser Thr Leu Phe Leu Leu Leu Arg Leu Arg Gly Gly
65                  70                  75

<210> SEQ ID NO 8
<211> LENGTH: 76
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant 21.5

<400> SEQUENCE: 8

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Asp
    50                  55                  60

Ser Thr Leu Phe Leu Leu Leu Arg Leu Arg Gly Gly
65                  70                  75

```
<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asp Tyr Lys Asp Asp Asp Lys
1               5

<210> SEQ ID NO 10
<211> LENGTH: 69
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: pdl1
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (34)..(48)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 10
gacgatgaca aaatgnnnat tnnngtgnnn accnnnnnnn nnnnnnnnat cnnnctcgag      60
gttgaaccc                                                              69

<210> SEQ ID NO 11
<211> LENGTH: 75
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: pdl2
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(33)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (43)..(45)
<223> OTHER INFORMATION: n is a, c, g, or t
```

```
<220> FEATURE:
<221> NAME/KEY: misc_feature
<222> LOCATION: (49)..(60)
<223> OTHER INFORMATION: n is a, c, g, or t

<400> SEQUENCE: 11
atccaggata aggaannnat tnnncctnnn nnncagnnnc tgnnntttnn nnnnnnnnnn      60
ctggaagatg gacgt                                                      75

<210> SEQ ID NO 12
<211> LENGTH: 63
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: pdl3
<220> FEATURE:
<221> NAME/KEY: misc_feature
<222> LOCATION: (16)..(24)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (40)..(48)
<223> OTHER INFORMATION: n is a, c, g, or t

<400> SEQUENCE: 12
tctgactaca atattnnnnn nnnntctnnn cttnnncttn nnnnnnnnct tcgtggtggt      60
ggc                                                                   63

<210> SEQ ID NO 13
<211> LENGTH: 227
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 8.2

<400> SEQUENCE: 13
atgcggattg tcgtgaaaac ccttatgggg aggaccatca cctcgaggtt gaaccctcgg      60
atacgataga aaatgtaaag gccaagatcc aggataagga aggaattcct cctgatcagc    120
agagactgat ctttgctggc aagcagctgg aagatgacg tactttgtct gactacaata    180
ttcacaatca ctctgctctt tatctttgt tgaaacttcg tggtggt                    227

<210> SEQ ID NO 14
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 8.3

<400> SEQUENCE: 14
atgtatattt tcgtgaaaac cttcatgggg aggaccatct acctcgaggt tgaaccctcg      60
```

```
gatacgatag aaaatgtaaa ggccaagatc caggataagg aaggaattcc tcctgatcag    120
cagagactga tctttgctgg caagcagctg gaagatggac gtactttgtc tgactacaat    180
atttcaaagg tgtctgctct ttaccttctg ttcagacttc gtggtggt                228
```

<210> SEQ ID NO 15
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 21.1

<400> SEQUENCE: 15

```
atgcagattt tcgtgaaaac ccttacgggg aagaccatca ccctcgaggt tgaaccctcg     60
gatacgatag aaaatgtaaa ggccaagatc caggataagg aaggaattcc tcctgatcag    120
cagagactga tctttgctgg caagcagctg gaagatggac gtactttgtc tgactacaat    180
attcagaaga tttctactct ttttcttctt atgagacttc gtggtggt                228
```

<210> SEQ ID NO 16
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 21.2

<400> SEQUENCE: 16

```
atgcagattt tcgtgaaaac ccttacgggg aagaccatca ccctcgaggt tgaaccctcg     60
gatacgatag aaaatgtaaa ggccaagatc caggataagg aaggaattcc tcctgatcag    120
cagagactga tctttgctgg caagcagctg gaagatggac gtactttgtc tgactacaat    180
attctgaagc ggtctactct ttttcttctc ttgaaacttc gtggtggt                228
```

<210> SEQ ID NO 17
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 21.3

<400> SEQUENCE: 17

```
atgcaaattt tcgtgaaaac cggtacgggg aagaccatca ttctcgaggt tgaaccctcg     60
gatacgatag aaaatgtaaa ggccaagatc caggataagg aaggaattcc tcctgatcag    120
cagagactga tctttgctgg caagcagctg gaagatggac gtactttgtc tgactacaat    180
attcttaagt cgtctacgct ttttcttttg ttgagacttc gtggtggt                228
```

<210> SEQ ID NO 18
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature

```
<223> OTHER INFORMATION: Ubiquitin variant 21.4

<400> SEQUENCE: 18
atgcagattt cgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg gaagatggac gtactttgtc tgactacaat    180
attcaaaagt ggtctacgct ttttcttttg ttgagacttc gtggtggt                 228

<210> SEQ ID NO 19
<211> LENGTH: 228
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Ubiquitin variant 21.5

<400> SEQUENCE: 19
atgcagattt cgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg gaagatggac gtactttgtc tgactacaat    180
attcagaagg actctactct ttttcttctg ttgaggcttc gtggtggt                 228

<210> SEQ ID NO 20
<211> LENGTH: 228
<212> TYPE: DNA
<213> ORGANISM: Homo sapiens
<220> FEATURE:
<221> NAME/KEY: misc_feature
<223> OTHER INFORMATION: Ubiquitin wildtype

<400> SEQUENCE: 20
atgcagattt cgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg gaagatggac gtactttgtc tgactacaat    180
attcaaaagg agtctactct tcatcttgtg ttgagacttc gtggtggt                 228

<210> SEQ ID NO 21
<211> LENGTH: 78
<212> TYPE: PRT
<213> ORGANISM: Homo sapiens

<400> SEQUENCE: 21

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Gly
65                  70                  75

<210> SEQ ID NO 22
<211> LENGTH: 78
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP2-A1

<400> SEQUENCE: 22

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Met Arg Leu Trp Ser His Arg Arg
65                  70                  75

<210> SEQ ID NO 23
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP2-A10

<400> SEQUENCE: 23

Met Gln Ile Phe Val Asn Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Trp Ser Glu Gly Thr
65                  70                  75

<210> SEQ ID NO 24
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP2-A12

<400> SEQUENCE: 24

Met Gln Ile Phe Val Met Thr Leu Thr Gly Gln Asn Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Leu Ser Gly Gly His
65                  70                  75

```
<210> SEQ ID NO 25
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-A3

<400> SEQUENCE: 25

Met Gln Ile Phe Val Lys Thr Leu Trp Thr Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Tyr Gly Val Lys Arg
65                  70                  75

<210> SEQ ID NO 26
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-A6

<400> SEQUENCE: 26

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Tyr Gly Gln Ala Ala
65                  70                  75

<210> SEQ ID NO 27
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-A7

<400> SEQUENCE: 27

Met Asp Ile Phe Val Asn Thr Ile Thr Gly Lys Ile Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ser Asp Tyr Asn Ile Pro Arg Tyr
    50                  55                  60

Ser Thr Leu His Leu Leu Leu Arg Leu Arg Gly Glu Ile Gln
65                  70                  75
```

<210> SEQ ID NO 28
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-A9

<400> SEQUENCE: 28

```
Met Gln Ile Phe Val Met Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Tyr
    50                  55                  60

Ser Thr Leu His Leu Val Leu Arg Leu Leu Gly Val Ser His
65                  70                  75
```

<210> SEQ ID NO 29
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-B10

<400> SEQUENCE: 29

```
Met Gln Ile Phe Val Tyr Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Tyr Ser Leu Asp Arg
65                  70                  75
```

<210> SEQ ID NO 30
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-B11

<400> SEQUENCE: 30

```
Met His Ile Phe Val Asn Thr Leu Thr Gly Lys Thr Ile Thr Leu Glu
1               5                   10                  15

Val Glu Pro Ser Asp Thr Ile Glu Asn Val Lys Ala Lys Ile Gln Asp
```

```
                    20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Trp Ser Cys Lys Gly
65                  70                  75
```

<210> SEQ ID NO 31
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-B12

<400> SEQUENCE: 31

```
Met Gln Ile Phe Val Lys Thr Leu Ser Gly Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Ser Gly Arg Lys
65                  70                  75
```

<210> SEQ ID NO 32
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-B7

<400> SEQUENCE: 32

```
Met Gln Ile Phe Val Asn Thr Leu Thr Gly Thr His Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Gly
65                  70                  75
```

<210> SEQ ID NO 33
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-B8

<400> SEQUENCE: 33

```
Met Gln Ile Phe Val Met Thr Leu Thr Gly Lys His Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75
```

<210> SEQ ID NO 34
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C10

<400> SEQUENCE: 34

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu His Ser Asn Ala Met
65                  70                  75
```

<210> SEQ ID NO 35
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C11

<400> SEQUENCE: 35

```
Met Gln Ile Phe Val Lys Thr Ile Ala Gly Lys Ala Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Leu Ser Gly Lys Arg
65                  70                  75
```

<210> SEQ ID NO 36
<211> LENGTH: 78
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: USP2-C3

<400> SEQUENCE: 36

Met Gln Ile Phe Val Asn Thr Leu Ser Gly Lys His Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75

<210> SEQ ID NO 37
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C5

<400> SEQUENCE: 37

Met Gln Ile Phe Val Asn Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Phe Ser Ala Arg Val
65                  70                  75

<210> SEQ ID NO 38
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C7

<400> SEQUENCE: 38

Met Gln Ile Phe Val Asn Thr Leu Thr Gly Arg His Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75

<210> SEQ ID NO 39
```

```
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C8

<400> SEQUENCE: 39

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Glu
    50                  55                  60

Ser Thr Leu His Leu Val Leu Arg Leu Leu Ser Gly Arg Arg
65                  70                  75

<210> SEQ ID NO 40
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-C9

<400> SEQUENCE: 40

Met Gln Ile Phe Val Asn Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Lys Lys Glu
    50                  55                  60

Ser Thr Leu His Leu Val Leu Arg Leu Trp Ser Trp Arg Arg
65                  70                  75

<210> SEQ ID NO 41
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D1

<400> SEQUENCE: 41

Met Gln Ile Phe Val Asn Thr Leu Thr Ala Arg Asn Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60
```

```
Ser Thr Leu Phe Leu Val Leu Arg Leu Arg Ser Glu Asn Leu
 65                  70                  75
```

<210> SEQ ID NO 42
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D11

<400> SEQUENCE: 42

```
Met Gln Ile Phe Val Lys Thr Leu Thr Gly Lys Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Leu Ser Gly Ser Ile
 65                  70                  75
```

<210> SEQ ID NO 43
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D3

<400> SEQUENCE: 43

```
Met Asp Ile Phe Val Asn Thr Leu Thr Gly Asn Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
 65                  70                  75
```

<210> SEQ ID NO 44
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D4

<400> SEQUENCE: 44

```
Met Glu Ile Phe Val Lys Thr Leu Thr Gly Lys Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
```

```
                35                  40                  45
Gln Leu Glu Asp Gly Arg Thr Leu Ser Asp Tyr Asn Ile Gln Lys Glu
    50                  55                  60

Ser Thr Leu His Leu Val Leu Arg Leu Trp Ser Ile Ser Phe
65                  70                  75
```

<210> SEQ ID NO 45
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D6

<400> SEQUENCE: 45

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Leu Ser Arg Ser Lys
65                  70                  75
```

<210> SEQ ID NO 46
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D7

<400> SEQUENCE: 46

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Leu Gly Tyr Ser Lys
65                  70                  75
```

<210> SEQ ID NO 47
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: USP2-D9

<400> SEQUENCE: 47

```
Met Asn Ile Phe Val Lys Thr Leu Ala Gly Asn His Ile Thr Leu Glu
1               5                   10                  15
```

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75

<210> SEQ ID NO 48
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-E4

<400> SEQUENCE: 48

Met Glu Ile Tyr Val Asn Thr Arg Leu Leu Glu Thr Ile Asn Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Lys
    50                  55                  60

Ser Thr Leu Tyr Leu Val Leu Arg Leu Leu Gly Gln Arg His
65                  70                  75

<210> SEQ ID NO 49
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-F11

<400> SEQUENCE: 49

Met Gln Ile Phe Val Gln Thr Arg Val Met Asn Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Thr Lys
        35                  40                  45

Gln Leu Glu Asp Gly Arg Thr Leu Ser Asp Tyr Asn Ile His Lys Asp
    50                  55                  60

Ser Thr Leu His Leu Leu Leu Arg Met Arg Arg Leu Asn Lys
65                  70                  75

<210> SEQ ID NO 50
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-F3

<400> SEQUENCE: 50

Met Gln Ile Phe Val Gln Thr Arg Ala Met Trp Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Pro Lys Glu
    50                  55                  60

Ser Thr Leu His Leu Val Leu Arg Leu Arg Gly Gly Gly Gly
65                  70                  75

<210> SEQ ID NO 51
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-F7

<400> SEQUENCE: 51

Met Gln Ile Phe Val Asn Thr Arg Thr Met Phe Thr Ile Arg Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 52
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-F8

<400> SEQUENCE: 52

Met Arg Ile Phe Val Lys Thr Arg Met Met Glu Ser Ile Phe Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Gln
        35                  40                  45

Gln Leu Glu Asp Gly Arg Thr Leu Ser Asp Tyr Asn Ile Gln Lys Glu
    50                  55                  60

Ser Thr Leu His Leu Val Val Arg Phe Arg Ser Ala Arg Arg
65                  70                  75

<210> SEQ ID NO 53
<211> LENGTH: 78
<212> TYPE: PRT
<213> ORGANISM: Artificial Sequence -continued
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-F9

<400> SEQUENCE: 53

Met Pro Ile Phe Val Asn Thr Arg Trp Met Lys Thr Ile Pro Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Asp Arg Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Asp Leu Gly Val Phe Cys
65                  70                  75

<210> SEQ ID NO 54
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G10

<400> SEQUENCE: 54

Met Gln Ile Met Val His Thr Arg Val Met Asn Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 55
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G11

<400> SEQUENCE: 55

Met Gln Ile Ser Val Asn Thr Arg Met Met Glu Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Leu Pro Glu
    50                  55                  60

Ser Thr Leu His Leu Val Leu Arg Leu Arg Gly Gly Gly Gly
65                  70                  75

<210> SEQ ID NO 56
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G3

<400> SEQUENCE: 56

```
Met Gln Ile Val Val Asn Thr Arg Met Met Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75
```

<210> SEQ ID NO 57
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G4

<400> SEQUENCE: 57

```
Met His Ile Phe Val Asn Thr Arg Ile Met Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75
```

<210> SEQ ID NO 58
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G5

<400> SEQUENCE: 58

```
Met His Ile Ser Val Asn Thr Arg Ser Met Trp Thr Ile Gln Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
```

Ser Thr Leu His Leu Val Leu Arg Leu Arg Gly Gly Gly Gly
65                  70                  75

<210> SEQ ID NO 59
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G6

<400> SEQUENCE: 59

Met Gln Ile Phe Val His Thr Arg Met Met Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Glu
    50                  55                  60

Ser Thr Leu His Leu Val Leu Arg Leu Arg Gly Gly Gly
65                  70                  75

<210> SEQ ID NO 60
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G8

<400> SEQUENCE: 60

Met Gln Ile Ile Val Arg Thr Arg Ala Met Trp Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Arg Thr Glu
    50                  55                  60

Ser Thr Leu His Leu Val Leu Arg Leu Arg Gly Gly Gly
65                  70                  75

<210> SEQ ID NO 61
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-G9

<400> SEQUENCE: 61

Met Gln Ile Phe Val Asn Thr Arg Met Met Asp Ser Ile Met Leu Glu
1               5                   10                  15

Val Glu Pro Ser Asp Thr Ile Glu Asn Val Lys Ala Lys Ile Gln Asp
            20                  25                  30

-continued

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 62
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H10

<400> SEQUENCE: 62

Met Gln Ile Phe Val Asn Thr Arg Met Met Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 63
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H11

<400> SEQUENCE: 63

Met Gln Ile Val Val Asn Thr Arg Ser Met Asn Thr Ile His Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Arg
    50                  55                  60

Ser Thr Leu Tyr Leu Val Leu Arg Leu Arg Gly Gly Gly Gly
65                  70                  75

<210> SEQ ID NO 64
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H12

<400> SEQUENCE: 64

Met Arg Ile Val Val Asn Thr Arg Tyr Met Asn Thr Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ile Phe Ala Gly Lys
        35                  40                  45

Gln Leu Glu Asp Gly Arg Thr Leu Ser Asp Tyr Asn Ile His Lys Glu
    50                  55                  60

Ser Thr Leu His Leu Val Leu Arg Leu Arg Gly Gly Gly Gly
65                  70                  75

<210> SEQ ID NO 65
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H4

<400> SEQUENCE: 65

Met Gln Ile Phe Val Asn Thr Arg Leu Met Tyr Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Ile Ser Arg Gly Leu Pro
65                  70                  75

<210> SEQ ID NO 66
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H7

<400> SEQUENCE: 66

Met Gln Ile Leu Val Arg Thr Arg Ile Met Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Asn
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 67
<211> LENGTH: 78
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<223> OTHER INFORMATION: Ubiquitin variant USP5-H8

<400> SEQUENCE: 67

Met Gln Ile Phe Val Asn Thr Arg Met Met Glu Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ser Leu Ile Phe Ala Gly Lys
        35                  40                  45

Arg Leu Glu Asp Gly Arg Thr Leu Ser Asp Tyr Asn Ile Gln Lys Ser
    50                  55                  60

Ser Thr Leu His Leu Val Leu Arg Leu Arg Gly Gly Gly
65                  70                  75

<210> SEQ ID NO 68
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP5-H9

<400> SEQUENCE: 68

Met Gln Ile Phe Val Asn Thr Arg Met Met Asn Thr Ile Asp Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75

<210> SEQ ID NO 69
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP10-Ubv.10.1

<400> SEQUENCE: 69

Met Gln Ile Phe Val Glu Thr Pro Met Gly Lys Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Val Phe Val Gly Lys
        35                  40                  45

Leu Leu Glu Asp Gly Arg Thr Leu Ser Asp Tyr Asn Ile Gln Arg Trp
    50                  55                  60

Ser Thr Leu Ala Leu Lys Phe Arg Leu Leu Ala Lys Asn Leu
65                  70                  75

<210> SEQ ID NO 70
<211> LENGTH: 78
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP48-Ubv.48.01

<400> SEQUENCE: 70

Met Gln Ile Ile Val Lys Thr Leu Thr Gly Gly Thr Ile Gly Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Phe Phe Ala Trp Thr
            35                  40                  45

Pro Leu Glu Asp Gly Arg Thr Leu Ser Asp Tyr Asn Ile Gln Met Glu
        50                  55                  60

Ser Thr Leu Arg Leu Phe Leu Arg Pro Arg Gly Leu Lys Glu
65                  70                  75

<210> SEQ ID NO 71
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP48-Ubv.48.02

<400> SEQUENCE: 71

Met Gln Ile Ser Val Lys Thr Leu Thr Gly Asn Met Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Thr Phe Val Phe Lys
            35                  40                  45

Gln Leu Glu Asp Gly Arg Thr Leu Ser Asp Tyr Asn Ile Gly Lys His
        50                  55                  60

Ser Thr Leu His Leu Trp Leu Arg Leu Leu Gly Ile Gly Lys
65                  70                  75

<210> SEQ ID NO 72
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP48-Ubv.48.03

<400> SEQUENCE: 72

Met Gln Ile Phe Val Lys Thr Leu Asn Gly Asn Ile Ile Ser Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Phe Phe Ala Trp Lys
            35                  40                  45

Gln Leu Glu Asp Gly Arg Thr Leu Ser Asp Tyr Asn Ile Pro Lys Glu
        50                  55                  60

Ser Thr Leu Pro Leu Phe Leu Arg Leu Arg Gly Gly Gly Gly
```

-continued

```
            65                  70                  75

<210> SEQ ID NO 73
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP48-Ubv.48.04

<400> SEQUENCE: 73

Met Gln Ile Ser Val Lys Thr Leu Thr Gly Gly Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Ala Phe Thr
        35                  40                  45

Pro Leu Glu Asp Gly Arg Thr Leu Ser Asp Tyr Asn Ile Gly Lys Gln
    50                  55                  60

Ser Thr Leu His Leu Trp Leu Arg Leu Leu Gly Leu Glu Glu
65                  70                  75

<210> SEQ ID NO 74
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP48-Ubv.48.05

<400> SEQUENCE: 74

Met Arg Ile Phe Val Glu Thr Leu Thr Gly Gln Ile Ile Asn Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Asn Phe Ala Gly Lys
        35                  40                  45

Leu Leu Glu Asp Gly Arg Thr Leu Ser Asp Tyr Asn Ile Lys Lys Trp
    50                  55                  60

Ser Thr Leu His Leu Val Leu Arg Leu Arg Gly Gly Gly
65                  70                  75

<210> SEQ ID NO 75
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-A11

<400> SEQUENCE: 75

Met Leu Ile Leu Val Lys Thr Leu Thr Gly His Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Ala Gly Lys
        35                  40                  45
```

Gln Leu Glu Asp Gly Arg Thr Leu Ser Asp Tyr Asn Ile His Lys Phe
       50                  55                  60

Ser Thr Leu His Leu Val Lys Arg Leu Arg Gly Arg Trp Lys
 65                  70                  75

<210> SEQ ID NO 76
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-A9

<400> SEQUENCE: 76

Met Arg Ile Phe Val Thr Thr Leu Thr Gly Arg Ala Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Thr Gly Lys
         35                  40                  45

Lys Leu Glu Asp Gly Arg Thr Leu Ser Asp Tyr Asn Ile Pro Lys Glu
     50                  55                  60

Ser Thr Leu Tyr Leu Val Lys Arg Leu Arg Gly Met Glu Gln
 65                  70                  75

<210> SEQ ID NO 77
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-B1

<400> SEQUENCE: 77

Met His Ile Phe Val Arg Thr Leu Thr Arg Lys Ile Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Phe Phe Thr Gly Met
         35                  40                  45

Thr Leu Glu Asp Gly Arg Thr Leu Ser Asp Tyr Asn Ile Gln Lys Glu
     50                  55                  60

Ser Thr Leu His Leu Val Leu Arg Leu Arg Gly Gly Gly Gly
 65                  70                  75

<210> SEQ ID NO 78
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-B10

<400> SEQUENCE: 78

Met Arg Ile Leu Val Lys Thr Leu Thr Arg Lys Val Ile Thr Leu Glu
 1               5                  10                  15

-continued

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Gln
        35                  40                  45

Arg Leu Glu Asp Gly Arg Thr Leu Ser Asp Tyr Asn Ile Gln Lys Glu
50                  55                  60

Ser Thr Leu His Leu Val Leu Arg Leu Arg Gly Gly Gly
65                  70                  75

<210> SEQ ID NO 79
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-B4

<400> SEQUENCE: 79

Met Gln Ile Phe Val Lys Thr Met Arg Arg Glu Ser Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Thr Gly Lys
        35                  40                  45

Gln Leu Glu Asp Gly Arg Thr Leu Ser Asp Tyr Asn Ile Gln Lys Glu
50                  55                  60

Ser Thr Leu His Leu Val Lys Arg Leu Pro Gly Arg Gln Tyr
65                  70                  75

<210> SEQ ID NO 80
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-B5

<400> SEQUENCE: 80

Met Gln Ile Val Val Lys Thr Leu Ser Arg Arg Thr Ile Gly Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Lys Leu Glu Asp Gly Arg Thr Leu Ser Asp Tyr Asn Ile Gln Lys Glu
    50                  55                  60

Ser Thr Leu His Leu Ala Leu Lys Leu Pro Gly Met Gly Gly
65                  70                  75

<210> SEQ ID NO 81
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-B6

<400> SEQUENCE: 81

Met Gln Ile Phe Val Lys Thr Phe Thr Gly Lys Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Asp Arg Asn
        35                  40                  45

Lys Leu Glu Asp Gly Arg Thr Leu Ser Asp Tyr Asn Ile Lys Lys Glu
    50                  55                  60

Ser Thr Leu Gly Leu Val Leu Arg Leu Arg Gly Gly Gly
65                  70                  75

<210> SEQ ID NO 82
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C1

<400> SEQUENCE: 82

Met Gln Ile Leu Val Gln Thr Leu Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Ala Gly Thr
        35                  40                  45

Gln Leu Glu Asp Gly Arg Thr Leu Ser Asp Tyr Asn Ile Gln Lys His
    50                  55                  60

Ser Thr Leu Tyr Leu Val Leu Arg Leu Leu Gly Arg Arg His
65                  70                  75

<210> SEQ ID NO 83
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C10

<400> SEQUENCE: 83

Met Gln Ile Leu Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Leu
        35                  40                  45

Lys Leu Glu Asp Gly Arg Thr Leu Ser Asp Tyr Asn Ile Gln Lys Val
    50                  55                  60

Ser Thr Leu Tyr Leu Val Lys Thr Phe Pro Gly Arg Arg Gln
65                  70                  75

<210> SEQ ID NO 84
<211> LENGTH: 78
<212> TYPE: PRT
<213> ORGANISM: Artificial Sequence
<220> FEATURE:

<223> OTHER INFORMATION: Synthetic peptide
<220> FEATURE:
<221> NAME/KEY: MISC_FEATURE
<223> OTHER INFORMATION: Ubiquitin variant Nedd4-N4-C11

<400> SEQUENCE: 84

```
Met Gln Ile Phe Val Lys Thr Leu Ala Gly Trp Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Arg Tyr Asp
    50                  55                  60

Ser Thr Leu His Leu Val Gly Arg Leu Arg Gly Gly Gly
65                  70                  75
```

<210> SEQ ID NO 85
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C12

<400> SEQUENCE: 85

```
Met Gln Ile Leu Val Lys Thr Leu Ala Arg Thr Ser Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly
65                  70                  75
```

<210> SEQ ID NO 86
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C2

<400> SEQUENCE: 86

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Asp
    50                  55                  60

Ser Thr Leu His Leu Val Arg Arg Leu Pro Arg Met Gly Lys
65                  70                  75
```

```
<210> SEQ ID NO 87
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C4

<400> SEQUENCE: 87

Met Tyr Ile Ser Val Lys Thr Leu Thr Gly Glu Ser Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Phe Phe Ala Gly Lys
        35                  40                  45

Ile Leu Glu Asp Gly Arg Thr Leu Ser Asp Tyr Asn Ile Leu Lys Trp
    50                  55                  60

Ser Thr Leu His Leu Val Lys Arg Leu Arg Ala Val His Met
65                  70                  75

<210> SEQ ID NO 88
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C5

<400> SEQUENCE: 88

Met Gln Ile Phe Val Lys Thr Leu Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Arg Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 89
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-C6

<400> SEQUENCE: 89

Met Pro Ile Val Val Lys Thr Leu Ala Gly Tyr Thr Ile His Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Leu Phe Ala Gly Asn
        35                  40                  45

Arg Leu Glu Asp Gly Arg Thr Leu Ser Asp Tyr Asn Ile His Asn Gly
    50                  55                  60
```

Ser Thr Leu Tyr Leu Val Lys Arg Leu Arg Gly Gly Gly
65                  70                  75

<210> SEQ ID NO 90
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D1

<400> SEQUENCE: 90

Met Gln Ile Phe Val Asn Thr Leu Ala Arg Thr Ser Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Arg Leu Pro Gly Thr Lys Val
65                  70                  75

<210> SEQ ID NO 91
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D10

<400> SEQUENCE: 91

Met Gln Ile Phe Val Arg Thr Leu Met Arg Lys Ser Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Ile Phe Ala Gly Lys
        35                  40                  45

Leu Leu Glu Asp Gly Arg Thr Leu Ser Asp Tyr Asn Ile Gln Lys Glu
    50                  55                  60

Ser Thr Leu His Leu Val Lys Lys Leu Ile Leu Leu Arg Glu
65                  70                  75

<210> SEQ ID NO 92
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D11

<400> SEQUENCE: 92

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

```
Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Gly Gly
65                  70                  75

<210> SEQ ID NO 93
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D12

<400> SEQUENCE: 93

Met Gln Ile Tyr Val Lys Thr Leu Thr Arg Lys Arg Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Phe Phe Asn Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly
65                  70                  75

<210> SEQ ID NO 94
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D2

<400> SEQUENCE: 94

Met Gln Ile Tyr Val Lys Thr Leu Thr Arg Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Tyr Leu Val Leu Arg Leu Arg Gly Gly Gly Gly
65                  70                  75

<210> SEQ ID NO 95
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D3

<400> SEQUENCE: 95

Met Lys Ile Ser Val Asn Thr Leu Thr Gly Lys Thr Ile Thr Leu Glu
```

```
                 1               5                  10                 15
Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Ile Phe Ala Gly Lys
           35                  40                 45

Gln Leu Glu Asp Gly Arg Thr Leu Ser Asp Tyr Asn Ile Gln Lys Tyr
       50                  55                 60

Ser Thr Leu Tyr Leu Val Lys Arg Leu Arg Arg Leu Lys Gln
65                  70                  75

<210> SEQ ID NO 96
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D5

<400> SEQUENCE: 96

Met Gln Ile Phe Val Pro Thr Leu Val Gln Lys Ala Ile Asn Leu Glu
1               5                  10                 15

Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Phe Phe Phe Arg Lys
           35                  40                 45

Pro Leu Glu Asp Gly Arg Thr Leu Ser Asp Tyr Asn Ile Lys Lys Glu
       50                  55                 60

Ser Thr Leu His Leu Leu Trp Arg Phe Ser Arg Leu Met
65                  70                  75

<210> SEQ ID NO 97
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Nedd4-N4-D8

<400> SEQUENCE: 97

Met Gln Ile Phe Val Arg Thr Leu Thr Gly Lys Thr Ile Thr Leu Glu
1               5                  10                 15

Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Ile Phe Ala Lys Gln
           35                  40                 45

Gln Leu Glu Asp Gly Arg Thr Leu Ser Asp Tyr Asn Ile Leu Lys Glu
       50                  55                 60

Ser Thr Leu Gly Leu Val Arg Arg Leu Arg Gly Leu Val Ser
65                  70                  75

<210> SEQ ID NO 98
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

<223> OTHER INFORMATION: Ubiquitin variant Nedd4-N4-D9

<400> SEQUENCE: 98

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Gln Val
    50                  55                  60

Ser Thr Leu Tyr Leu Val Lys Arg Leu Arg Gly Gly Gly
65                  70                  75

<210> SEQ ID NO 99
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.01
<220> FEATURE:
<221> NAME/KEY: MISC_FEATURE
<223> OTHER INFORMATION: Ubv.ITCH.0

<400> SEQUENCE: 99

Met Pro Ile Leu Val Lys Thr Leu Arg Gly Gln Ser Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Phe Leu Ile Phe Ala Arg Lys
        35                  40                  45

His Leu Glu Asp Gly Arg Thr Leu Ser Asp Tyr Asn Ile Gln Lys Arg
    50                  55                  60

Ser Thr Leu Tyr Leu Phe Leu Arg Phe His Gly Met Val Ala
65                  70                  75

<210> SEQ ID NO 100
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.02

<400> SEQUENCE: 100

Met His Ile Leu Val Lys Thr Leu Arg Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Gly Gly Asn
        35                  40                  45

Lys Leu Glu Asp Gly Arg Thr Leu Ser Asp Tyr Asn Ile Gln Lys Glu
    50                  55                  60

Ser Thr Leu Tyr Leu Leu Leu Arg Arg Leu Gly Ser Lys Phe
65                  70                  75

-continued

```
<210> SEQ ID NO 101
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.03

<400> SEQUENCE: 101
```

Met Gln Ile Phe Val Ile Thr His Thr Trp Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Ala Arg Gln
        35                  40                  45

Lys Leu Glu Asp Gly Arg Thr Leu Ser Asp Tyr Asn Ile Gln Lys Asp
    50                  55                  60

Ser Thr Leu His Leu Val Leu Ile Arg Arg Val Ser Lys Arg
65                  70                  75

```
<210> SEQ ID NO 102
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.04

<400> SEQUENCE: 102
```

Met Gln Ile Phe Val Lys Thr Leu Thr Gly Leu Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Gly Gly Lys
        35                  40                  45

Arg Leu Glu Asp Gly Arg Thr Leu Ser Asp Tyr Asn Ile Gln Lys Lys
    50                  55                  60

Ser Thr Leu Tyr Leu Leu Met Arg Leu Arg Gly Val Ser Arg
65                  70                  75

```
<210> SEQ ID NO 103
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.05

<400> SEQUENCE: 103
```

Met Gln Ile Phe Val Lys Thr Leu Thr Gly Thr Asp Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Leu Phe Ala Gly Lys
        35                  40                  45

Gln Leu Glu Asp Gly Arg Thr Leu Ser Asp Tyr Asn Ile Pro Gly Asp
    50                  55                  60

Ser Thr Leu Tyr Leu Leu Met Arg Phe Gly Val Asn Lys Arg
65                  70                  75

<210> SEQ ID NO 104
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.ITCH.06

<400> SEQUENCE: 104

Met Pro Ile Leu Val Gln Thr Leu Arg Gly Gln Ser Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Phe Leu Ile Phe Ala Arg Thr
        35                  40                  45

His Leu Glu Asp Gly Arg Thr Leu Ser Asp Tyr Asn Ile Gln Lys Gly
    50                  55                  60

Ser Thr Leu Tyr Leu Leu Arg Phe His Gly Thr Val Ala
65                  70                  75

<210> SEQ ID NO 105
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1.01

<400> SEQUENCE: 105

Met Gln Ile Leu Val Lys Thr Val Ile Val Lys Thr Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ile Phe Ala Gly Met
        35                  40                  45

Gln Leu Glu Asp Gly Arg Thr Leu Ser Asp Tyr Asn Ile Arg Arg Ala
    50                  55                  60

Ser Thr Leu His Leu Val Gly Arg Leu Arg Gly Gly Gly
65                  70                  75

<210> SEQ ID NO 106
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1.02

<400> SEQUENCE: 106

Met Gln Ile Phe Val Gln Thr Leu Ile Val Lys Thr Ile Ile Leu Glu
1               5                   10                  15

Val Glu Pro Ser Asp Thr Ile Glu Asn Val Lys Ala Lys Ile Gln Asp
            20                  25                  30

```
Lys Glu Gly Ile Pro Pro Asp Gln Gln Tyr Leu Ile Phe Ala Gly Lys
             35                  40                  45

Gln Leu Glu Asp Gly Arg Thr Leu Ser Asp Tyr Asn Ile Gly Met Glu
 50                  55                  60

Ser Thr Leu Arg Leu Val Gly Arg Leu Arg Gly Gly Gly
 65                  70                  75
```

<210> SEQ ID NO 107
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1.03

<400> SEQUENCE: 107

```
Met Pro Ile Ser Val Val Thr Leu Ile Val Lys Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Ser Leu Ile Phe Ala Gly Lys
             35                  40                  45

Gln Leu Glu Asp Gly Arg Thr Leu Ser Asp Tyr Asn Ile Gln Asn Arg
 50                  55                  60

Ser Thr Leu His Leu Val Gly Arg Leu Arg Gly Gly Gly
 65                  70                  75
```

<210> SEQ ID NO 108
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1.04

<400> SEQUENCE: 108

```
Met Leu Ile Phe Val Thr Thr Val Arg Val Ser Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ser Asp Tyr Asn Ile Leu Lys Glu
 50                  55                  60

Ser Thr Leu Lys Leu Val Trp Ile Phe Arg Gly Asn Arg Thr
 65                  70                  75
```

<210> SEQ ID NO 109
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1a.01

<400> SEQUENCE: 109

```
Met Gln Ile Leu Val Lys Thr Val Ile Val Lys Thr Ile Ser Leu Glu
```

```
                1               5                  10                 15
Val Glu Pro Ser Asp Thr Ile Glu Asn Val Lys Ala Lys Ile Gln Asp
                20                 25                 30

Lys Glu Gly Ile Pro Pro Asp Gln Gln Thr Leu Ile Phe Ala Gly Met
            35                 40                 45

Gln Leu Glu Asp Gly Arg Thr Leu Ser Asp Tyr Asn Ile Arg Arg Ala
        50                 55                 60

Ser Thr Leu His Leu Val Gly Arg Leu Arg Gly Gly Gly
65                 70                 75

<210> SEQ ID NO 110
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1a.02

<400> SEQUENCE: 110

Met Glu Ile Val Val Gln Thr Leu Ile Val Lys Ser Ile Thr Leu Glu
1               5                  10                 15

Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Ile Phe Gly Gly Asp
            35                 40                 45

Phe Leu Glu Asp Gly Arg Thr Leu Ser Asp Tyr Asn Ile Gln Lys Glu
        50                 55                 60

Ser Thr Leu His Leu Val Ser Trp Leu Arg Gly Gly Gly
65                 70                 75

<210> SEQ ID NO 111
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1a.03

<400> SEQUENCE: 111

Met Gln Ile Ile Val Glu Thr Ile Thr Val Lys Thr Ile Ala Leu Glu
1               5                  10                 15

Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Ile Phe Ala Gly Lys
            35                 40                 45

Gln Leu Glu Asp Gly Arg Thr Leu Ser Asp Tyr Asn Ile His Lys Glu
        50                 55                 60

Ser Thr Leu Leu Leu Val Ser Trp Leu His Gly Asp Arg Gln
65                 70                 75

<210> SEQ ID NO 112
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

<223> OTHER INFORMATION: Ubiquitin variant Ubv.UIM1a.04

<400> SEQUENCE: 112

Met Gln Ile Phe Val Gln Thr Leu Ile Val Lys Thr Ile Ile Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Tyr Leu Ile Phe Ala Gly Lys
        35                  40                  45

Gln Leu Glu Asp Gly Arg Thr Leu Ser Asp Tyr Asn Ile Gly Met Glu
    50                  55                  60

Ser Thr Leu Arg Leu Val Gly Arg Leu Arg Gly Gly Gly
65                  70                  75

<210> SEQ ID NO 113
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1a.05

<400> SEQUENCE: 113

Met Gln Ile Phe Val Gln Thr Ile Thr Val Met Arg Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Met
        35                  40                  45

Gln Leu Glu Asp Gly Arg Thr Leu Ser Asp Tyr Asn Ile Lys Arg Asp
    50                  55                  60

Ser Thr Leu Tyr Leu Val Ser Ser Leu Arg Gly Leu Arg Ala
65                  70                  75

<210> SEQ ID NO 114
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1a.06

<400> SEQUENCE: 114

Met Gln Ile Phe Val Gln Thr Leu Thr Val Lys Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Arg
        35                  40                  45

Gln Leu Glu Asp Gly Arg Thr Leu Ser Asp Tyr Asn Ile Gln Lys Gly
    50                  55                  60

Ser Thr Leu His Leu Val Ala Trp Leu Arg Gly Gly Gly Gly
65                  70                  75

<210> SEQ ID NO 115
<211> LENGTH: 78
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.01

<400> SEQUENCE: 115

Met Arg Ile Phe Val Lys Thr Ile Thr Val Lys Ser Ile His Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ile Phe Ala Gly Lys
        35                  40                  45

Leu Leu Glu Asp Gly Arg Thr Leu Ser Asp Tyr Asn Ile Lys Lys Glu
    50                  55                  60

Ser Thr Leu His Leu Val Ala Lys His Arg Gly Met Glu Val
65                  70                  75

<210> SEQ ID NO 116
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.02

<400> SEQUENCE: 116

Met Gln Ile Phe Val Lys Thr Leu Thr Val Thr Ile Tyr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Asp
    50                  55                  60

Ser Thr Leu Gly Leu Val Leu Lys Phe Arg Ala Leu Val Arg
65                  70                  75

<210> SEQ ID NO 117
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.03

<400> SEQUENCE: 117

Met Gln Ile Phe Val Ile Thr Phe Ser Gly Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Asn Leu Ile Phe Gly Gly Arg
        35                  40                  45

Gln Leu Glu Asp Gly Arg Thr Leu Ser Asp Tyr Asn Ile Gln Gln Val
    50                  55                  60

Ser Thr Leu Leu Leu Val Leu Ser Leu Arg Gly Thr Arg Glu
65                  70                  75
```

<210> SEQ ID NO 118
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.04

<400> SEQUENCE: 118

Met Gln Ile Phe Val Lys Thr Leu Ala Val Lys Thr Ile Glu Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Asp
    50                  55                  60

Ser Thr Leu Gly Leu Val Leu Ser Val Arg Val Leu Arg Arg
65                  70                  75

<210> SEQ ID NO 119
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.05

<400> SEQUENCE: 119

Met Gln Ile Asn Val Asn Thr Leu Met Val Lys Ala Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Gly Ala Lys
        35                  40                  45

Gln Leu Glu Asp Gly Arg Thr Leu Ser Asp Tyr Asn Ile Gln Lys Glu
    50                  55                  60

Ser Thr Leu Tyr Leu Val Phe Ser Leu Arg Gly Lys Gly Gln
65                  70                  75

<210> SEQ ID NO 120
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.06

<400> SEQUENCE: 120

Met Leu Ile Phe Val Lys Thr Leu Arg Val Glu Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

```
Gln Leu Glu Asp Gly Arg Thr Leu Ser Asp Tyr Asn Ile Gly Lys Glu
 50                  55                  60

Ser Thr Leu Gly Leu Val Thr Arg Leu Arg Val Tyr Glu Ser
 65                  70                  75
```

```
<210> SEQ ID NO 121
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.07

<400> SEQUENCE: 121

Met Thr Ile Phe Val Thr Thr Ile Ile Val Asn Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ser Asp Tyr Asn Ile Lys Lys Glu
 50                  55                  60

Ser Thr Leu Arg Leu Val Ser Arg His Arg Thr Val Lys
 65                  70                  75
```

```
<210> SEQ ID NO 122
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.08

<400> SEQUENCE: 122

Met His Ile Phe Val Lys Thr Leu Thr Val Lys Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ile Phe Val Arg Gln
             35                  40                  45

His Leu Glu Asp Gly Arg Thr Leu Ser Asp Tyr Asn Ile Gln Lys Glu
 50                  55                  60

Ser Thr Leu Gly Leu Val Leu Ser Leu Arg Gly Ile Ala Lys
 65                  70                  75
```

```
<210> SEQ ID NO 123
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.09

<400> SEQUENCE: 123

Met Gln Ile Phe Val Gly Thr Leu Thr Val Asn Gly Ile Asn Leu Glu
 1               5                  10                  15

Val Glu Pro Ser Asp Thr Ile Glu Asn Val Lys Ala Lys Ile Gln Asp
```

```
            20                  25                  30

Lys Glu Gly Ile Pro Pro Asp Gln Gln Arg Leu Phe Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Gly
65                  70                  75

<210> SEQ ID NO 124
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.10

<400> SEQUENCE: 124

Met Gln Ile Phe Val Lys Thr Leu Thr Val Asn Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Ile Phe Ala Gly Lys
            35                  40                  45

Gln Leu Glu Asp Gly Arg Thr Leu Ser Asp Tyr Asn Ile Gln Lys Asp
        50                  55                  60

Ser Thr Leu Gly Leu Val Ser Arg Leu Arg Gly Gly Gly
65                  70                  75

<210> SEQ ID NO 125
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.11

<400> SEQUENCE: 125

Met Gln Ile Leu Val Thr Thr Ile Ile Val Arg Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ser Gly Lys
            35                  40                  45

Glu Leu Glu Asp Gly Arg Thr Leu Ser Asp Tyr Asn Ile Arg Asn Lys
        50                  55                  60

Ser Thr Leu Tyr Leu Val Gly Arg Leu Arg Gly Gly Gly
65                  70                  75

<210> SEQ ID NO 126
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.12

<400> SEQUENCE: 126
```

Met Gln Ile Phe Val Asn Thr Leu Arg Ala Lys Phe Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Ala Gly Gln
        35                  40                  45

Gln Leu Glu Asp Gly Arg Thr Leu Ser Asp Tyr Asn Ile His Lys Glu
    50                  55                  60

Ser Thr Leu Ser Leu Val Ala Ser Leu Arg Gly Asp Gln Lys
65                  70                  75

<210> SEQ ID NO 127
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.13

<400> SEQUENCE: 127

Met Gln Ile Phe Val Leu Thr Leu Lys Trp Lys Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ser Gly Trp
        35                  40                  45

His Leu Glu Asp Gly Arg Thr Leu Ser Asp Tyr Asn Ile Glu Lys Gly
    50                  55                  60

Ser Thr Leu Gly Leu Val Leu Thr Leu Arg Gly Gly Gly Gly
65                  70                  75

<210> SEQ ID NO 128
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant Ubv.UIM1b.14

<400> SEQUENCE: 128

Met Glu Ile Ser Val Lys Thr Leu Ala Val Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Ala Gly Lys
        35                  40                  45

Leu Leu Glu Asp Gly Arg Thr Leu Ser Asp Tyr Asn Ile His Arg Glu
    50                  55                  60

Ser Thr Leu Leu Leu Val Leu Arg Ile Tyr Arg Arg Ala Ser
65                  70                  75

<210> SEQ ID NO 129
<211> LENGTH: 78
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Ubiquitin variant Ubv.UIM1b.15

<400> SEQUENCE: 129

Met Lys Ile Phe Val Thr Thr Leu Thr Val Lys Thr Ile Ala Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Gly Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu Leu Leu Gly Val Met Leu Arg Ala Asn Arg Ser
65                  70                  75

<210> SEQ ID NO 130
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A01

<400> SEQUENCE: 130

Met Gln Ile Phe Val Lys Thr Pro Lys Gly Lys Asn Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ile Ala Lys
            35                  40                  45

His Leu Glu Asp Gly Arg Thr Leu Ser Asp Tyr Asn Ile Pro Lys Glu
        50                  55                  60

Ser Thr Leu Ser Leu Leu Met Ser Phe Pro Arg Thr Val Arg
65                  70                  75

<210> SEQ ID NO 131
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A03

<400> SEQUENCE: 131

Met Gln Ile Phe Val Lys Thr Leu Arg Gly His Leu Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Val Ala Lys
            35                  40                  45

Gln Leu Glu Asp Gly Arg Thr Leu Ser Asp Tyr Asn Ile His Lys Glu
        50                  55                  60

Ser Thr Leu Gln Leu Met Phe Lys Pro Arg Gly Gln Arg Arg
65                  70                  75

<210> SEQ ID NO 132
```

```
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A04

<400> SEQUENCE: 132

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ser Leu Ser Phe Ala Gly Lys
        35                  40                  45

Pro Leu Glu Asp Gly Arg Thr Leu Ser Asp Tyr Asn Ile His Arg Thr
    50                  55                  60

Ser Thr Leu His Leu Val Phe Ser Phe Arg Ser Arg Val Lys
65                  70                  75

<210> SEQ ID NO 133
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A06

<400> SEQUENCE: 133

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ser Leu Ser Phe Ala Gly Lys
        35                  40                  45

Pro Leu Glu Asp Gly Arg Thr Leu Ser Asp Tyr Asn Ile His Arg Thr
    50                  55                  60

Ser Thr Leu His Leu Val Phe Ser Phe Arg Ser Lys Val Lys
65                  70                  75

<210> SEQ ID NO 134
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A07

<400> SEQUENCE: 134

Met Gln Ile Phe Val Lys Thr Leu Arg Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Phe Phe Asp Val Lys
        35                  40                  45

Gln Leu Glu Asp Gly Arg Thr Leu Ser Asp Tyr Asn Ile Gln Lys Glu
    50                  55                  60
```

Ser Thr Leu Asp Leu Phe Leu Gly Leu Arg Gly Arg Ser Arg
65      70      75

<210> SEQ ID NO 135
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A08

<400> SEQUENCE: 135

Met Gln Ile Phe Val Lys Thr Leu Thr Gly Lys Thr Ile Thr Leu Glu
1     5      10      15

Val Glu Pro Ser Asp Thr Ile Glu Asn Val Lys Ala Lys Ile Gln Asp
     20      25      30

Lys Glu Gly Ile Pro Pro Asp Gln Gln Arg Leu Ile Phe Ser Gly Lys
    35      40      45

Pro Leu Glu Asp Gly Arg Thr Leu Ser Asp Tyr Asn Ile Pro Lys Glu
  50      55      60

Ser Thr Leu Asp Leu Gly Leu Arg Arg Arg Thr Thr Val Ser
65      70      75

<210> SEQ ID NO 136
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-A09

<400> SEQUENCE: 136

Met Gln Ile Phe Val Lys Thr Leu Thr Gly Lys Thr Ile Thr Leu Glu
1     5      10      15

Val Glu Pro Ser Asp Thr Ile Glu Asn Val Lys Ala Lys Ile Gln Asp
     20      25      30

Lys Glu Gly Ile Pro Pro Asp Gln Gln Arg Leu Ile Phe Ala Gly Lys
    35      40      45

Gln Leu Glu Asp Gly Arg Thr Leu Ser Asp Tyr Asn Ile Asn Trp Glu
  50      55      60

Ser Thr Leu Arg Leu Trp Ser Arg Val Arg Gly Lys Tyr Gln
65      70      75

<210> SEQ ID NO 137
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-B03

<400> SEQUENCE: 137

Met Gln Ile Phe Val Lys Thr Val Lys Gly Glu Thr Ile Val Leu Glu
1     5      10      15

Val Glu Pro Ser Asp Thr Ile Glu Asn Val Lys Ala Lys Ile Gln Asp
     20      25      30

Lys Glu Gly Ile Pro Pro Asp Gln Gln Lys Leu Tyr Phe Asp Val Lys

```
                    35                  40                  45

Gln Leu Glu Asp Gly Arg Thr Leu Ser Asp Tyr Asn Ile Gln Gln Glu
    50                  55                  60

Ser Thr Leu His Leu Leu Val Arg Leu Gly Gly Arg Gly Gly
65                  70                  75
```

<210> SEQ ID NO 138
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-B06

<400> SEQUENCE: 138

```
Met Gln Ile Phe Val Ile Thr Phe Pro Gly Lys Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Leu Phe Asp Val Lys
        35                  40                  45

Gln Leu Glu Asp Gly Arg Thr Leu Ser Asp Tyr Asn Ile Gln Asn Glu
    50                  55                  60

Ser Thr Leu Asn Leu Val Trp Arg Pro Arg Gly Val Leu Asn
65                  70                  75
```

<210> SEQ ID NO 139
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-B09

<400> SEQUENCE: 139

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Asp Val Lys
        35                  40                  45

Gln Leu Glu Asp Gly Arg Thr Leu Ser Asp Tyr Asn Ile Gln Thr Tyr
    50                  55                  60

Ser Thr Leu His Leu Gly Leu Arg Leu Arg Gly His Thr Thr
65                  70                  75
```

<210> SEQ ID NO 140
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP8-B10

<400> SEQUENCE: 140

```
Met Gln Ile Phe Val Lys Thr Leu Met Gly Arg Ala Ile Thr Leu Glu
1               5                   10                  15
```

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Ala
    50                  55                  60

Ser Thr Leu Tyr Leu Met Leu Arg Leu Arg Gly Gly Gly
65                  70                  75

<210> SEQ ID NO 141
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 141

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Glu Trp Lys
    50                  55                  60

Ser Thr Leu Phe Leu Leu Leu Arg Leu Arg Ser Ile Leu Leu
65                  70                  75

<210> SEQ ID NO 142
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 142

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Pro Lys Glu
    50                  55                  60

Ser Thr Leu Phe Leu Leu Val Arg Leu Phe Val Lys Gln Ile
65                  70                  75

<210> SEQ ID NO 143
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 143

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Glu Thr Gly
    50                  55                  60

Ser Thr Leu Phe Leu Leu Phe Arg Leu Arg Gly Met Gly Thr
65                  70                  75

<210> SEQ ID NO 144
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 144

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Leu
    50                  55                  60

Ser Thr Leu Phe Leu Leu Arg Phe Arg Ser Tyr Met Arg
65                  70                  75

<210> SEQ ID NO 145
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 145

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Tyr His Lys
    50                  55                  60

Ser Thr Leu Phe Leu Leu Val Lys Phe Arg Gly Leu Thr Pro
65                  70                  75

<210> SEQ ID NO 146
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 146

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Asn Glu
    50                  55                  60

Ser Thr Leu Phe Leu Leu Arg Phe Pro Arg Val Gln Ala
65                  70                  75

<210> SEQ ID NO 147
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 147

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Pro Lys Ala
    50                  55                  60

Ser Thr Leu Phe Leu Leu Arg Leu His Ala Gln Arg Arg
65                  70                  75

<210> SEQ ID NO 148
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 148

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Phe
    50                  55                  60

Ser Thr Leu Phe Leu Leu Arg Leu Gly Gly Trp Tyr Leu
65                  70                  75

-continued

```
<210> SEQ ID NO 149
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 149

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Gln
    50                  55                  60

Ser Thr Leu Phe Leu Val Leu Arg Leu Arg Gly Lys Asp Met
65                  70                  75

<210> SEQ ID NO 150
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 150

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Arg Gln
    50                  55                  60

Ser Thr Leu Tyr Leu Leu Ile Arg Ile His Arg Arg Lys Arg
65                  70                  75

<210> SEQ ID NO 151
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 151

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys His
```

Ser Thr Leu Tyr Leu Leu Phe Arg Phe Thr Val Lys Gly Arg
65                  70                  75

<210> SEQ ID NO 152
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 152

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Pro Arg His
    50                  55                  60

Ser Thr Leu Phe Leu Leu Phe Arg Leu Arg Asp Thr Ser Arg
65                  70                  75

<210> SEQ ID NO 153
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 153

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Ala
    50                  55                  60

Ser Thr Leu Phe Leu Val Leu Arg Val Arg Ala His Lys Gln
65                  70                  75

<210> SEQ ID NO 154
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 154

Met Glu Ile Phe Val Lys Thr Leu Ser Gly Met Thr Ile Thr Leu Glu
1               5                   10                  15

Val Glu Pro Ser Asp Thr Ile Glu Asn Val Lys Ala Lys Ile Gln Asp
            20                  25                  30

```
Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys His
    50                  55                  60

Ser Thr Leu Phe Leu Val Leu Arg Leu His Val Gly Asn Asn
65                  70                  75
```

<210> SEQ ID NO 155
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 155

```
Met Gln Ile Phe Val Lys Thr Val Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Lys
    50                  55                  60

Ser Thr Leu Phe Leu Val Leu Arg Leu His Ser Thr Arg Glu
65                  70                  75
```

<210> SEQ ID NO 156
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 156

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Glu
    50                  55                  60

Ser Thr Leu Phe Leu Leu Leu Arg Phe Arg Gly Thr Leu Ser
65                  70                  75
```

<210> SEQ ID NO 157
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 157

Met Gln Ile Phe Val Lys Thr Val Thr Gly Arg Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Thr Lys
    50                  55                  60

Ser Thr Leu Phe Leu Val Leu Arg Phe Arg Gly Asn Thr Arg
65                  70                  75

<210> SEQ ID NO 158
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 158

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Glu Lys Glu
    50                  55                  60

Ser Thr Leu Phe Leu Leu Leu Arg Leu Pro Ser Trp Lys Gly
65                  70                  75

<210> SEQ ID NO 159
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 159

Met Gln Ile Tyr Val Lys Thr Leu Pro Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Leu Arg
    50                  55                  60

Ser Thr Leu Phe Leu Leu Phe Arg Pro Arg Arg Leu Tyr Lys
65                  70                  75

<210> SEQ ID NO 160
<211> LENGTH: 78
<212> TYPE: PRT
<213> ORGANISM: Artificial Sequence
<220> FEATURE:
<223> OTHER INFORMATION: Synthetic peptide
<220> FEATURE:

-continued

<221> NAME/KEY: MISC_FEATURE
<223> OTHER INFORMATION: Ubiquitin variant USP21-

<400> SEQUENCE: 160

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Glu Lys Lys
        50                  55                  60

Ser Thr Leu Phe Leu Leu Leu Arg Leu Tyr Trp Glu Asp Lys
65                  70                  75

<210> SEQ ID NO 161
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 161

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Tyr Asn Glu
        50                  55                  60

Ser Thr Leu Phe Leu Leu Ala Arg Leu Arg Phe Gly Arg Ala
65                  70                  75

<210> SEQ ID NO 162
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 162

Met Gln Ile Phe Val Lys Thr Ser Thr Gly Arg Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Arg Gln
        50                  55                  60

Ser Thr Leu Phe Leu Ile Trp Arg Leu Thr Ser Ala Met Val
65                  70                  75

<210> SEQ ID NO 163
<211> LENGTH: 78

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 163

Met Gln Ile Phe Val Lys Thr His Thr Ala Lys Thr Ile Leu Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Asn Leu Glu
    50                  55                  60

Ser Thr Leu Phe Leu Leu Phe Arg Phe Arg Gly Asn Thr Leu
65                  70                  75

<210> SEQ ID NO 164
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 164

Met Gln Ile Phe Val Lys Thr Pro Thr Gly Met Ser Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Val
    50                  55                  60

Ser Thr Leu Phe Leu Val Phe Lys Leu Trp Arg Arg Ser Met
65                  70                  75

<210> SEQ ID NO 165
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 165

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys Glu
    50                  55                  60

Ser Thr Leu Phe Leu Leu Leu Arg Leu Ser Trp Asp Phe Lys
```

```
                65                  70                  75

<210> SEQ ID NO 166
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 166

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile His Lys His
    50                  55                  60

Ser Thr Leu Phe Leu Leu Leu Arg Leu Arg Ser Arg Leu Lys
65                  70                  75

<210> SEQ ID NO 167
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 167

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Val Lys Asn
    50                  55                  60

Ser Thr Leu Phe Leu Leu Leu Arg Ile His Gly Ser Gln Lys
65                  70                  75

<210> SEQ ID NO 168
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 168

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

Gln Leu Glu Asp Gly Arg Thr Leu Ser Asp Tyr Asn Ile His Lys Gln
            50                  55                  60

Ser Thr Leu Phe Leu Val Leu Arg Leu Arg Gly Leu Ser Ser
65                  70                  75

<210> SEQ ID NO 169
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Ubiquitin variant USP21-

<400> SEQUENCE: 169

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Asp
    50                  55                  60

Ser Thr Leu Phe Leu Leu Arg Leu Arg Gly Leu Gln Tyr
65                  70                  75

<210> SEQ ID NO 170
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: UIM1

<400> SEQUENCE: 170

Gly Gly Gly Gly Ala Ala Asp Glu Glu Glu Leu Ile Arg Lys Ala Ile
1               5                   10                  15

Glu Leu Ser Leu Lys Glu Ser Arg Asn Ser Gly Gly Tyr
            20                  25

<210> SEQ ID NO 171
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: UIM1a

<400> SEQUENCE: 171

Gly Gly Gly Gly Ala Ala Asp Glu Glu Glu Leu Ile Arg Lys Ala Ile
1               5                   10                  15

Glu Leu Ala Leu Lys Glu Ser Arg Asn Ser Gly Gly Tyr
            20                  25

<210> SEQ ID NO 172
<211> LENGTH: 29
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<223> OTHER INFORMATION: UIM1b

<400> SEQUENCE: 172

Gly Gly Gly Gly Ala Ala Asp Glu Glu Glu Leu Ile Arg Lys Leu Ile
1               5                   10                  15

Glu Leu Ser Leu Lys Glu Ser Arg Asn Ser Gly Gly Tyr
            20                  25

<210> SEQ ID NO 173
<211> LENGTH: 78
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Arg, Tyr, Asp, His, Glu, Pro, Leu, Thr,
      or Lys
<220> FEATURE:
<221> NAME/KEY: MISC_FEATURE
<222> LOCATION: (4)..(4)
<223> OTHER INFORMATION: Xaa is Val, Asp, Met, Tyr, Ser, Ile or Leu
<220> FEATURE:
<221> NAME/KEY: MISC_FEATURE
<222> LOCATION: (6)..(6)
<223> OTHER INFORMATION: Xaa is Asn, Met, Iso, Gln, His, Arg, Glu, Thr,
      Pro, Val, Gly, Leu or Tyr
<220> FEATURE:
<221> NAME/KEY: MISC_FEATURE
<222> LOCATION: (8)..(8)
<223> OTHER INFORMATION: Xaa is Phe, Gly, Ile, Arg, Pro, Met, His, Val
      or Ser
<220> FEATURE:
<221> NAME/KEY: MISC_FEATURE
<222> LOCATION: (9)..(9)
<223> OTHER INFORMATION: Xaa is Met, Trp, Ser, Ala, Leu, Val, Ile, Tyr,
      Asn, Arg, Lys or Pro
<220> FEATURE:
<221> NAME/KEY: MISC_FEATURE
<222> LOCATION: (10)..(10)
<223> OTHER INFORMATION: Xaa is Thr, Ala, Leu, Met, Arg, Gln, Trp, Val,
      His or Glu
<220> FEATURE:
<221> NAME/KEY: MISC_FEATURE
<222> LOCATION: (11)..(11)
<223> OTHER INFORMATION: Xaa is Arg, Thr, Asn, Glu, Trp, Phe, Asp, Met,
      Tyr, Gly, Gln, His, Leu, Ser or Ala
<220> FEATURE:
<221> NAME/KEY: MISC_FEATURE
<222> LOCATION: (12)..(12)
<223> OTHER INFORMATION: Xaa is Ile, His, Ala, Asn, Ser, Met, Val, Gly,
      Arg, Asp or Phe
<220> FEATURE:
<221> NAME/KEY: MISC_FEATURE
<222> LOCATION: (14)..(14)
<223> OTHER INFORMATION: Xaa is Ile, Tyr, Asn, Arg, Phe, Pro, Gln, Ala,
      Met, His, Ser, Gly, Asp, Glu or Leu
<220> FEATURE:
<221> NAME/KEY: MISC_FEATURE
<222> LOCATION: (42)..(42)
<223> OTHER INFORMATION: Xaa is Thr, Ser, Lys, Phe, Ile, Tyr, Asn or Gly
<220> FEATURE:
<221> NAME/KEY: MISC_FEATURE
<222> LOCATION: (44)..(44)
<223> OTHER INFORMATION: Xaa is Val, Phe, Thr, Asn, Leu, Ser or Tyr
<220> FEATURE:
<221> NAME/KEY: MISC_FEATURE
<222> LOCATION: (46)..(46)
<223> OTHER INFORMATION: Xaa is Asp, Val, Thr, Asn, Phe, Gly, Ser or Ile
<220> FEATURE:
<221> NAME/KEY: MISC_FEATURE
<222> LOCATION: (47)..(47)
```

```
<223> OTHER INFORMATION: Xaa is Thr, Arg, Trp, Phe, Arg, Lys, Ala or Val
<220> FEATURE:
<221> NAME/KEY: MISC_FEATURE
<222> LOCATION: (48)..(48)
<223> OTHER INFORMATION: Xaa is Gln, Asn, Thr, Met, Leu, Asp, Arg or Trp
<220> FEATURE:
<221> NAME/KEY: MISC_FEATURE
<222> LOCATION: (49)..(49)
<223> OTHER INFORMATION: Xaa is Arg, Leu, Pro, Lys, Thr, Ile, His, Phe
      or Glu
<220> FEATURE:
<221> NAME/KEY: MISC_FEATURE
<222> LOCATION: (62)..(62)
<223> OTHER INFORMATION: Xaa is His, Ser, Leu, Pro, Arg, Gly, Lys, Glu,
      Asn, Tyr or Val
<220> FEATURE:
<221> NAME/KEY: MISC_FEATURE
<222> LOCATION: (63)..(63)
<223> OTHER INFORMATION: Xaa is Asn, Arg, Lys, Pro, Thr, Met, Tyr, Gln,
      Gly, Trp, His or Leu
<220> FEATURE:
<221> NAME/KEY: MISC_FEATURE
<222> LOCATION: (64)..(64)
<223> OTHER INFORMATION: Xaa is His, Val, Ile, Arg, Ser, Trp, Asp, Tyr,
      Lys, Gln, Phe, Gly, Ala, Thr, Leu or Asn
<220> FEATURE:
<221> NAME/KEY: MISC_FEATURE
<222> LOCATION: (66)..(66)
<223> OTHER INFORMATION: Xaa is Ala or Tyr
<220> FEATURE:
<221> NAME/KEY: MISC_FEATURE
<222> LOCATION: (68)..(68)
<223> OTHER INFORMATION: Xaa is Tyr, Phe, Ala, Arg, Pro, Gly, Lys, Leu,
      Ser, Gln, Asp or Asn
<220> FEATURE:
<221> NAME/KEY: MISC_FEATURE
<222> LOCATION: (70)..(70)
<223> OTHER INFORMATION: Xaa is Leu, Lys, Phe, Trp, Ala, Gly, Met or Ile
<220> FEATURE:
<221> NAME/KEY: MISC_FEATURE
<222> LOCATION: (71)..(71)
<223> OTHER INFORMATION: Xaa is Phe, Met, Val, Lys, Gly, Arg, Trp, Ser,
      Ala, Thr or Ile
<220> FEATURE:
<221> NAME/KEY: MISC_FEATURE
<222> LOCATION: (72)..(72)
<223> OTHER INFORMATION: Xaa is Lys, Thr, Ile, Trp, Ser, Met or Gly
<220> FEATURE:
<221> NAME/KEY: MISC_FEATURE
<222> LOCATION: (73)..(73)
<223> OTHER INFORMATION: Xaa is Met, Phe, Asp, Ile, Pro, Arg, His or Val
<220> FEATURE:
<221> NAME/KEY: MISC_FEATURE
<222> LOCATION: (74)..(74)
<223> OTHER INFORMATION: Xaa is Trp, Leu, Tyr, His, Phe, Ser, Pro, Ile,
      Gly or Thr
<220> FEATURE:
<221> NAME/KEY: MISC_FEATURE
<222> LOCATION: (75)..(75)
<223> OTHER INFORMATION: Xaa is Ser, Arg, Ala, Leu, Val, Thr, Asp, Trp
      or Phe
<220> FEATURE:
<221> NAME/KEY: MISC_FEATURE
<222> LOCATION: (76)..(76)
<223> OTHER INFORMATION: Xaa is His, Glu, Val, Gln, Leu, Cys, Asn, Ala,
      Trp, Ile, Arg, Tyr, Met, Thr Asp or Lys
<220> FEATURE:
<221> NAME/KEY: MISC_FEATURE
<222> LOCATION: (77)..(77)
<223> OTHER INFORMATION: Xaa is Arg, Lys, Ala, Ile, Ser, Asp, Asn, Phe,
      Glu, Trp, Gln, His, Leu, Val, Tyr, Thr or Met
<220> FEATURE:
<221> NAME/KEY: MISC_FEATURE
<222> LOCATION: (78)..(78)
<223> OTHER INFORMATION: Xaa is Arg, Thr, Ala, Gln, His, Lys, Met, Val,
      Leu, Ile, Phe, Cys, Glu, Tyr, Ser, Asn or Pro

<400> SEQUENCE: 173
```

```
Met Xaa Ile Xaa Val Xaa Thr Xaa Xaa Xaa Xaa Ile Xaa Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Xaa Leu Xaa Phe Xaa Xaa Xaa
            35              40                  45

Xaa Leu Glu Asp Gly Arg Thr Leu Ser Asp Tyr Asn Ile Xaa Xaa Xaa
    50              55                  60

Ser Xaa Leu Xaa Leu Xaa Xaa Xaa Xaa Xaa Xaa Xaa
65              70              75
```

SPECIFIC ACTIVE SITE INHIBITORS OF ENZYMES OR SUBSTRATE BINDING PARTNERS AND METHODS OF PRODUCING SAME

FIELD OF THE DISCLOSURE

The disclosure relates to specific active site inhibitors of substrate binding partners including, but not limited to, enzymes, and methods of producing said inhibitors. The disclosure also relates to ubiquitin variants that specifically bind ubiquitin binding partners and, in some embodiments, inhibit enzymes.

BACKGROUND OF THE DISCLOSURE

Ubiquitination is a reversible post-translational modification that plays major roles in multiple signaling events and in determining the longevity of proteins in cells [Hershko and Ciechanover 1998; Glickman and Ciechanover 2002; Chen 2005; Ye and Rape 2009]. Over the past decade, it has become clear that the biological importance of ubiquitination rivals and may exceed that of phosphorylation, and consequently, there is great interest in deciphering the details of this process in both normal and diseased cells.

The process of ubiquitination is hierarchical and involves an enzyme cascade with increasing complexity [Hershko and Ciechanover 1998]. In the last step of the cascade, E3 ligases facilitate the transfer of ubiquitin (Ub) onto protein substrates through a covalent linkage between the C-terminal glycine of Ub and the ε-amino group of a substrate lysine. Subsequently, polymeric Ub chains are extended on the substrate through linkages between the C termini and lysines of additional Ub monomers. The nature of these Ub-substrate and Ub-Ub linkages is precisely controlled by diverse Ub ligases, and in humans, more than 600 E3 ligases mediate substrate specificity.

Deubiquitinating enzymes (DUBs) counteract the processes initiated by ubiquitination, and thus regulate cellular homeostasis and signaling. The human genome encodes approximately 95 putative DUBs which have been divided into five structural families, as follows [Nijman, Luna-Vargas et al. 2005]: Ubiquitin specific proteases (USPs), Ubiquitin C-terminal hydrolases (UCHs), ovarian tumor proteases (OTUs), Machado-Joseph disease proteases (MJDs) and JAB1/MPN/MOV34 metalloenzymes (JAMMs). Aside from approximately eight JAMM family members, which are metalloproteases, most known human DUBs are cysteine proteases. The general understanding of deubiquitination has lagged behind the general understanding of ubiquitination within the scientific community, but several recent studies have revealed central roles for DUBs in the control of cell signaling.

In particular, the largest DUB family consists of 58 USPs that are essential for many cellular processes and pathways. For example, USP21 and USP22 have been implicated in the deubiquitination of histones [Nakagawa, Kajitani et al. 2008; Zhang, Varthi et al. 2008], while USP1, USP2a, USP7 and USP28 are involved in the DNA damage response [Cummins and Vogelstein 2004; Li, Brooks et al. 2004; Nijman, Huang et al. 2005; Zhang, Zaugg et al. 2006; Stevenson, Sparks et al. 2007]. The USP family members share a structurally conserved catalytic domain with a well-defined catalytic cleft, suggesting that it may be possible to develop a general structure-based strategy for inhibiting family members by using similar yet specific molecular entities, as has been the case for kinases that have been targeted with small molecules built on common scaffolds [Fedorov, Marsden et al. 2007]. Unfortunately, no specific inhibitors of USPs or other DUBs have yet been reported, and a lack of such inhibitors imposes a formidable roadblock to attempts to understand and manipulate deubiquitination pathways for therapeutic benefit.

Numerous USPs have been implicated in diseases including neurodegeneration, haematological diseases, viral and bacterial infections, and cancer [Goldenberg, McDermott et al. 2008]. Indeed, DUBs are direct antagonists of oncogenic and tumor-suppressive E3 ligases, and USPs are increasingly seen as potential targets for cancer therapy. Several USPs are up-regulated in cancer (e.g. USP2a, USP4, USP10) [Gray, Inazawa et al. 1995; Grunda, Nabors et al. 2006; Priolo, Tang et al. 2006], are directly involved in the regulation of tumor-suppressive proteins (e.g. USP2a and USP7) [Cummins and Vogelstein 2004; Li, Brooks et al. 2004; Priolo, Tang et al. 2006] or carry mutations which are found in hereditary cancers (CYLD) [Saggar, Chernoff et al. 2008]. USP8 is implicated in ubiquitin remodeling, down regulation of epidermal growth factor receptor (EGFR), clathrin-mediated internalization, endosomal sorting, the control of receptor tyrosine kinases and it may be involved in the patho-physiology of breast cancer [Mizuno, lura et al. 2005; Avvakumov, Walker et al. 2006; Niendorf, Oksche et al. 2007]. USP21 deubiquitinates histone 2A, and in doing so, influences the methylation status of histone 3, which has a major impact on transcriptional control. More recently USP21 was also shown to be involved in NF-κB activation induced by tumor-necrosis factor α [Xu, Tan et al. 2010] and therefore could be involved in many disease areas such as cancer, inflammation, viral infections and auto-immune diseases.

One of the best-studied examples of USP function is the role of USP7 in the regulation of the tumor suppressor p53 and its associated E3 ligase mdm2. USP7 deubiquitinates both p53 and mdm2 but the net effect of its function is to stabilize mdm2, and consequently, to destabilize p53. Thus, an inhibitor of USP7 would stabilize p53 and could be a potential cancer therapeutic, because p53-induced apoptosis in response to DNA damage has been proposed as a therapeutic strategy for several cancers [Chen 2005; Colland, Formstecher et al. 2009]. Mdm2 is also deubiquitinated by USP2a, which is up-regulated in prostate cancer [Priolo, Tang et al. 2006], and thus, inhibitors of USP2a would also be promising therapeutics. Recently, it has been shown that USP10 counteracts the effects of USP7 and USP2a by deubiquitinating and stabilizing p53 [Yuan, Luo et al. 2010].

USPs are multi-domain proteins that, in addition to a catalytic domain, typically contain various Ub recognition motifs and other protein-protein interaction domains [Komander, Clague et al. 2009]. Although catalytic domains of different USPs often share low sequence homology, crystal structures have revealed a common fold that defines the family [Hu, Li et al. 2002; Reyes-Turcu, Ventii et al. 2009] and a common catalytic triad that mediates catalysis [Wilkinson 1997]. The pKa of the catalytic cysteine is lowered by a histidine, and a third residue, usually asparagine or aspartate, polarizes and aligns the histidine side-chain.

Structures of five USP catalytic domains in complex with Ub also reveal a common binding site for the substrate [Hu, Li et al. 2002; Hu, Li et al. 2005; Renatus, Parrado et al. 2006]. In all cases, Ub is bound in the same orientation and the isopeptide linkage is aligned in the active site. While the affinity of USPs for Ub is low, the contact surface between Ub and the USP is large, as for example, the contact surface of the Ub and USP7 complex is known to be 1800 Å². Notably, despite a common function, the Ub-binding sites of USP family members differ in sequence, and consequently, the Ub-binding surfaces are similar but exhibit significant topological variation. In the case of USP7, approximately 75% of the Ub-binding surface is composed of residues that are not conserved in the USP family.

In US 2006/0099686 A1, a modified Ub was used to establish an alternative binding-scaffold to a predetermined binding partner it did not recognize before. The modified ubiquitin had the point mutations I44A, K48R, R54L, V70A, R72L, G75A and the last glycine in the protein was removed. These mutations prevented ubiquitin from interacting with its natural binding partner and avoided conjugation with other ubiquitin molecules through Lys48. In this modified ubiquitin the inventors also randomized the residues 2, 4 and 6 in the N-terminal part and residues 62-66 in addition to the point mutations to produce a continuous surface on one side of the ubiquitin and used phage display to select for high affinity variants to hydrocortisone (hapten) and proteins such as vascular endothelial growth factor (VEGF) and Fc part of IgG antibodies. They achieved affinities in the 170 nM-10 µM range. The surface of ubiquitin is not particularly well suited to generate binding surfaces to haptens since it lacks a cavity to allow an efficient shielding of the hydrophobic surface of a molecule like hydrocortisone. In addition, the solvent accessible binding surface covered by these residues is relatively small (500 Å²), and does not provide enough structural diversity for an efficient binding of other proteins. This explains the comparable low affinity interactions the inventors have observed which makes a diagnostic or pharmaceutical usage difficult.

SUMMARY OF THE DISCLOSURE

The present disclosure focuses on the existing interactions of substrates with their binding partners, including enzymes, and using as an example, the ubiquitination pathway that already have a ubiquitin (Ub)-binding site, to develop higher affinity binding partners that are more suited to diagnostic or pharmaceutical usage. The present disclosure provides a method of preparing ubiquitin variants that specifically bind to a ubiquitin specific protease (USP), a ubiquitin ligase, or a ubiquitin interaction motif (UIM). Based on this method, specific Ub variants were identified that bind tightly to particular USPs, ubiquitin ligases, and UIMs, but not to others. These specific Ub variants act as potent, competitive inhibitors of USP activity by blocking the binding or interfering with the binding of Ub substrates to their binding partners, i.e. USP, ubiquitin ligase, or UIM.

The disclosure includes a ubiquitin binding partner, wherein the ubiquitin binding partner is a ubiquitin polypeptide or a fragment thereof comprising an amino acid mutation in a region selected from the group consisting of: (a) region 1 (amino acids 2-14), region 2 (amino acids 35-49), or region 3 (amino acids 62-72) of the amino acid sequence of ubiquitin (Ub) set forth in SEQ ID NO:1; and (b) region 1 (amino acids 2-14), region 2 (amino acids 42-49), or region 3 (amino acids 62-78) of the amino acid sequence of a ubiquitin variant (Ubv) set forth in SEQ ID NO:21. In some aspects, the ubiquitin binding partner is a ubiquitin-interacting motif (UIM) or a ubiquitin enzyme inhibitor. In some aspects, the ubiquitin binding partner inhibits a ubiquitin enzyme selected from the group consisting of: a ubiquitin-activating enzyme (E1 enzyme), a ubiquitin-conjugating enzyme (E2 enzyme), a ubiquitin ligase (E3 enzyme), and a deubiquitinating enzyme. In some aspects, the ubiquitin binding partner is a ubiquitin ligase. In some aspects, the ubiquitin ligase is neural precursor cell expressed developmentally down-regulated protein 4 (Nedd4) or ITCH. In some aspects, the ubiquitin binding partner is a deubiquitinating enzyme. In some aspects, the deubiquitinating enzyme is a ubiquitin-specific protease (USP), a ubiquitin C-terminal hydrolase (UCH), an ovarian tumor-related protease (OTU), a Machado-Joseph disease (MJD) protease or a JAB1/MPN/MOV34 metalloenzyme (JAMM) protease. In other aspects, the deubiquitinating enzyme is a ubiquitin-specific protease (USP).

The disclosure includes a ubiquitin binding partner wherein the ubiquitin binding partner is a ubiquitin polypeptide or a fragment thereof comprising an amino acid mutation wherein the mutation is a substitution in a region of a ubiquitin polypeptide or a fragment thereof selected from the group consisting of: (a) region 1 (amino acids 2-14) wherein the polypeptide comprises the structure:

$$X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14},$$ (SEQ ID NO: 173)

wherein, $X_2$ is selected from the group consisting of Arg, Tyr, Asp, His, Glu, Pro, Leu, Thr and Lys;

$X_4$ is selected from the group consisting of Val, Asp, Met, Tyr, Ser, Ile and Leu;

$X_6$ is selected from the group consisting of Asn, Met, Ile, Gln, His, Arg, Glu, Thr, Pro, Val, Gly, Leu and Tyr;

$X_8$ is selected from the group consisting of Phe, Gly, Ile, Arg, Pro, Met, His, Val and Ser;

$X_9$ is selected from the group consisting of Met, Trp, Ser, Ala, Leu, Val, Ile, Tyr, Asn, Arg, Lys and Pro; $X_{10}$ is selected from the group consisting of Thr, Ala, Leu, Met, Arg, Gln, Trp, Val, His and Glu;

$X_{11}$ is selected from the group consisting of Arg, Thr, Asn, Glu, Trp, Phe, Asp, Met, Tyr, Gly, Gln, His, Leu, Ser and Ala;

$X_{12}$ is selected from the group consisting of Ile, His, Ala, Asn, Ser, Met, Val, Gly, Arg, Asp and Phe;

$X_{14}$ is selected from the group consisting of Ile, Tyr, Asn, Arg, Phe, Pro, Gln, Ala, Met, His, Ser, Gly, Asp, Glu and Leu;

(b) region 2 (amino acids 35-49) wherein the polypeptide comprises the structure:

$$X_{35}\text{-}X_{36}\text{-}X_{37}\text{-}X_{38}\text{-}X_{39}\text{-}X_{40}\text{-}X_{41}\text{-}X_{42}\text{-}X_{43}\text{-}X_{44}\text{-}X_{45}\text{-}X_{46}\text{-}X_{47},$$ (SEQ ID NO: 173)

wherein, $X_{35}$ is Gln;

$X_{37}$ is Asp;

$X_{42}$ is selected from the group consisting of Thr, Ser, Lys, Phe, Ile, Tyr, Asn, and Gly;

$X_{44}$ is selected from the group consisting of Val, Phe, Thr, Asn, Leu, Ser, and Tyr;

$X_{46}$ is selected from the group consisting of Asp, Val, Thr, Asn, Phe, Gly, Ser and Ile;

$X_{47}$ is selected from the group consisting of Thr, Arg, Trp, Phe, Arg, Lys, Ala, and Val;

$X_{48}$ is selected from the group consisting of Gln, Asn, Thr, Met, Leu, Asp, Arg, and Trp;

X$_{49}$ is selected from the group consisting of Arg, Leu, Pro, Lys, Thr, Ile, His, Phe, and Glu; and (c) region 3 (amino acids 62-78) wherein the polypeptide comprises the structure:

(SEQ ID NO: 173)
X$_{62}$-X$_{63}$-X$_{64}$-X$_{65}$-X$_{66}$-X$_{67}$-X$_{68}$-X$_{69}$-X$_{70}$-X$_{71}$-X$_{72}$-X$_{73}$-X$_{74}$-X$_{75}$-X$_{76}$-X$_{77}$-X$_{78}$, wherein, X$_{62}$ is selected from the group consisting of His, Ser, Leu, Pro, Arg, Gly, Lys, Glu, Asn, Tyr and Val;

X$_{63}$ is selected from the group consisting of Asn, Arg, Lys, Pro, Thr, Met, Tyr, Gln, Gly, Trp, His and Leu;

X$_{64}$ is selected from the group consisting of His, Val, Ile, Arg, Ser, Trp, Asp, Tyr, Lys, Gln, Phe, Gly, Ala, Thr, Leu and Asn;

X$_{66}$ is selected from the group consisting of Ala and Tyr;

X$_{68}$ is selected from the group consisting of Tyr, Phe, Ala, Arg, Pro, Gly, Lys, Leu, Ser, Gln, Asp, and Asn;

X$_{70}$ is selected from the group consisting of Leu, Lys, Phe, Trp, Ala, Gly, Met, and Ile;

X$_{71}$ is selected from the group consisting of Phe, Met, Val, Lys, Gly, Arg, Trp, Ser, Ala, Thr and Ile;

X$_{72}$ is selected from the group consisting of Lys, Thr, Ile, Trp, Ser, Met and Gly;

X$_{73}$ is selected from the group consisting of Met, Phe, Asp, Ile, Pro, Arg, His and Val;

X$_{74}$ is selected from the group consisting of Trp, Leu, Tyr, His, Phe, Ser, Pro, Ile, Gly and Thr;

X$_{75}$ is selected from the group consisting of Ser, Arg, Ala, Leu, Val, Thr, Asp, Trp and Phe;

X$_{76}$ is selected from the group consisting of His, Glu, Val, Gln, Leu, Cys, Asn, Ala, Trp, Ile, Arg, Tyr, Met, Thr Asp and Lys;

X$_{77}$ is selected from the group consisting of Arg, Lys, Ala, Ile, Ser, Asp, Asn, Phe, Glu, Trp, Gln, His, Leu, Val, Tyr, Thr and Met; and X$_{78}$ is selected from the group consisting of Arg, Thr, Ala, Gln, His, Lys, Met, Val, Leu, Ile, Phe, Cys, Glu, Tyr, Ser, Asn and Pro.

In some aspects, the ubiquitin binding partner comprises an amino acid mutation at position 2, 4, 6, 8, 9, 10, 11, 12, 14, 35, 37, 39, 40, 42, 44, 46, 47, 48, 49, 62, 63, 64, 66, 68, 70, 71 or 72 in the amino acid sequence of ubiquitin set forth in SEQ ID NO:1. In other aspects, the ubiquitin binding partner comprises an amino acid mutation at position 2, 4, 6, 8, 9, 10, 11, 12, 14, 62, 63, 64, 66, 68, 70, 71 or 72 in the amino acid sequence of ubiquitin set forth in SEQ ID NO: 1. In more particular aspects, the ubiquitin binding partner comprises an amino acid mutation at position 2, 4, 8, 9, 11, 14, 62, 63, 64, 66, 68, 70, 71 or 72 in the amino acid sequence of ubiquitin set forth in SEQ ID NO:1. In some aspects, the ubiquitin binding partner binds to ubiquitin-specific protease 8 (USP8). In some aspects, the ubiquitin binding partner comprises the amino acid sequence of any one of SEQ ID NOS: 2-3.

In some aspects, the ubiquitin binding partner comprises an amino acid mutation at position 8, 14, 62, 64, 68, 70, 71 or 72 in the amino acid sequence of ubiquitin set forth in SEQ ID NO: 1. In some aspects, the ubiquitin binding partner binds to ubiquitin-specific protease 21 (USP21). In some aspects, the ubiquitin binding partner comprises an amino acid sequence of any one of SEQ ID NOS: 4-8.

In some aspects, the ubiquitin binding partner comprises an amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 in the amino acid sequence of a ubiquitin variant (Ubv) set forth in SEQ ID NO: 21. In other aspects, the ubiquitin binding partner comprises an amino acid mutation at position 2, 6, 8, 9, 10, 11, 12, 62, 63, 64, 68, 70, 71, 74, 75, 76, 77, or 78 in the amino acid sequence of the ubiquitin variant (Ubv) set forth in SEQ ID NO: 21. In some aspects, the ubiquitin binding partner binds to ubiquitin-specific protease 2a (USP2a). In some aspects, the ubiquitin binding partner comprises an amino acid sequence of any one of SEQ ID NOS: 22-47. In particular aspects, the ubiquitin binding partner binds to USP2a and increases cell death. In some aspects, the cell death is apoptosis. In some aspects, the cells are cancer cells. In certain aspects, the cancer cells are prostate cancer cells.

In some aspects, the ubiquitin binding partner comprises an amino acid mutation at position 2, 4, 6, 8, 9, 10, 11, 12, 14, 42, 46, 47, 48, 49, 62, 63, 64, 68, 70, 71, 73, 74, 75, 76, 77, or 78 in the amino acid sequence of the ubiquitin variant (Ubv) set forth in SEQ ID NO:21. In some aspects, the ubiquitin binding partner binds to ubiquitin-specific protease USP5. In some aspects, the ubiquitin binding partner comprises the amino acid sequence set forth in any one of SEQ ID NOS: 48-68. In particular aspects, the ubiquitin binding partner increases transcription of tumor suppressor protein p53 and or increases free poly-ubiquitin. In some aspects, increases in transcription of p53 decreases proliferation of p53-dependent tumor cells. In certain aspects, the tumor cells are cancer cells.

In some aspects, the ubiquitin binding partner comprises an amino acid mutation at position 6, 8, 9, 14, 44, 46, 49, 63, 64, 68, 70, 71, 74, 75, 76, 77, or 78 in the amino acid sequence of the ubiquitin variant (Ubv) set forth in SEQ ID NO: 21. In some aspects, the ubiquitin binding partner binds ubiquitin-specific protease 10 (USP10). In some aspects, the ubiquitin binding partner comprises the amino acid sequence set forth in SEQ ID NO: 69. In some aspects, the ubiquitin binding partner increases transcription of tumor suppressor protein p53. In particular aspects, such increase in transcription of p53 decreases proliferation of p53-dependent tumor cells. In some aspects, such tumor cells are cancer cells.

In some aspects, the ubiquitin binding partner comprises an amino acid mutation at position 2, 4, 6, 8, 9, 11, 12, 14, 44, 46, 47, 48, 49, 62, 63, 64, 68, 70, 73, 74, 76, 77, or 78 in the amino acid sequence of the ubiquitin variant (Ubv) set forth in SEQ ID NO:21. In some aspects, the ubiquitin binding partner binds ubiquitin-specific protease 48 (USP48). In some aspects, the ubiquitin binding partner comprises the amino acid sequence set forth in any one of SEQ ID NOS: 70-74. In particular aspects, the ubiquitin binding partner decreases proliferation of cancer cells. In some aspects, such cancer cells are pancreatic cancer cells.

In some aspects, the ubiquitin binding partner comprises an amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 in the amino acid sequence of the ubiquitin variant (Ubv) set forth in SEQ ID NO:21. In some aspects, such ubiquitin binding partner binds neural precursor cell expressed developmentally down-regulated protein 4 (Nedd4). In some aspects, such ubiquitin binding partner comprises the amino acid sequence set forth in any one of SEQ ID NOS: 75-98. In some aspects, the ubiquitin binding partner binds E3 ubiquitin ligase ITCH. In some aspects, the ubiquitin binding partner comprises the amino acid sequence set forth in any one of SEQ ID NOS: 99-104. In some aspects, such binding to ITCH results in decreased ubiquitination of proteins. In some aspects, such binding to ITCH decreases proliferation of tumor cells. In further aspects, the ubiquitin binding partner binds ubiquitin interaction motifs (UIM). In some aspects, the ubiquitin binding partner comprises the amino acid sequence set forth in any one of SEQ ID NOS: 105-129.

In some aspects, the ubiquitin binding partner comprises an amino acid mutation at position 6, 8, 9, 11, 12, 14, 42, 44, 46, 47, 49, 62, 63, 64, 68, 70, 71, 72, 73, 74, 75, 76, 77, or 78 in the amino acid sequence of the ubiquitin variant (Ubv) set forth in SEQ ID NO:21. In some aspects, the ubiquitin binding partner binds to ubiquitin-specific protease 8 (USP8). In some aspects, the ubiquitin binding partner comprises the amino acid sequence set forth in any one of SEQ ID NOS: 130-140.

In some aspects, the ubiquitin binding partner comprises an amino acid mutation at position 2, 6, 8, 9, 10, 11, 12, 14, 62, 63, 64, 68, 70, 71, 72, 73, 74, 75, 76, 77, or 78 in the amino acid sequence of the ubiquitin variant (Ubv) set forth in SEQ ID NO: 21. In some aspects, the ubiquitin binding partner binds to ubiquitin-specific protease 21 (USP21). In some aspects, the ubiquitin binding partner comprises the amino acid sequence set forth in any one of SEQ ID NOS: 141-169.

The disclosure also includes nucleic acids encoding any of the ubiquitin binding partners described herein. The disclosure further includes recombinant expression vectors comprising such nucleic acid molecules. The disclosure also includes host cells comprising such nucleic acid molecules or recombinant expression vectors.

The disclosure also includes methods of identifying a substrate variant as a substrate-specific binding partner comprising: (a) randomizing active site residues of a substrate in an enzyme substrate complex or in a complex comprising a substrate binding partner and a substrate to produce a combinatorial library of substrate variants; and (b) selecting the substrate variant that binds the substrate as a substrate-specific binding partner. In some aspects, such active site residues are identified by a method selected from analysis of 3D structures, alanine scanning, shotgun scanning or mutational analysis of interaction interfaces. In some aspects, such randomizing of the active site residues is performed by genetic engineering. In certain aspects, the randomizing is performed to yield 75% wild type amino acid residues and 25% mutated amino acid residues in the active site residues.

In some aspects, selecting the substrate variant that inhibits enzyme activity or binds substrate is performed by phage display to determine inhibition of enzyme activity or substrate binding in the variant compared to a control. In certain aspects, when the substrate binding partner is an enzyme, the control is an enzyme different than the enzyme in the enzyme substrate complex thereby selecting for enzyme specificity. In other aspects, when the substrate binding partner is an enzyme the control is the enzyme in the enzyme substrate complex thereby testing for amount of enzyme activity inhibition. In some aspects, such inhibition is competitive inhibition, product inhibition or allosteric inhibition. In some aspects, the enzyme is a transferase, hydrolase, lyase, or ligase. In further aspects, the substrate is ubiquitin (Ub) and the enzyme is a ubiquitin-activating enzyme (E1 enzyme), a ubiquitin-conjugating enzyme (E2 enzyme), a ubiquitin ligase (E3 enzyme), and a deubiquitinating enzyme. In particular aspects, such ubiquitin ligase is neural precursor cell expressed developmentally down-regulated protein 4 (Nedd4) or ITCH. In more particular aspects, such deubiquitinating enzyme is a ubiquitin specific protease (USP), a ubiquitin C-terminal hydrolase (UCH), an ovarian tumor protease (OTU), a Machado-Joseph disease (MJD) protease or a JAB1/MPN/MOV34 metalloenzyme (JAMM) protease. In other aspects, the deubiquitinating enzyme is a ubiquitin specific protease (USP). In some aspects, such USP is USP2, USP5, USP8, USP10, USP21 or USP48. In other aspects, such methods as described herein above are included wherein the substrate is ubiquitin (Ub) and the substrate binding partner is a ubiquitin-interacting motif (UIM).

The disclosure also includes methods of identifying a substrate variant as a substrate-specific binding partner, wherein the substrate is ubiquitin as set forth in SEQ ID NO:1 or a ubiquitin variant as set forth in SEQ ID NO: 21 and the ubiquitin binding partner is a ubiquitin polypeptide or a fragment thereof comprising an amino acid mutation in a region selected from the group consisting of: (a) region 1 (amino acids 2-14), region 2 (amino acids 35-49), or region 3 (amino acids 62-72) of the amino acid sequence of ubiquitin (Ub) set forth in SEQ ID NO:1; and (b) region 1 (amino acids 2-14), region 2 (amino acids 42-49), or region 3 (amino acids 62-78) of the amino acid sequence of a ubiquitin variant (Ubv) set forth in SEQ ID NO:21. In some aspects, such mutation is a substitution in a region of a ubiquitin polypeptide or a fragment thereof selected from the group consisting of:

(a) region 1 (amino acids 2-14) wherein the polypeptide comprises the structure:

(SEQ ID NO: 173)
$X_2-X_3-X_4-X_5-X_6-X_7-X_8-X_9-X_{10}-X_{11}-X_{12}-X_{13}-X_{14}$, wherein, $X_2$ is selected from the group consisting of Arg, Tyr, Asp, His, Glu, Pro, Leu, Thr and Lys;

$X_4$ is selected from the group consisting of Val, Asp, Met, Tyr, Ser, Ile and Leu;

$X_6$ is selected from the group consisting of Asn, Met, Ile, Gln, His, Arg, Glu, Thr, Pro, Val, Gly, Leu and Tyr;

$X_8$ is selected from the group consisting of Phe, Gly, Ile, Arg, Pro, Met, His, Val and Ser;

$X_9$ is selected from the group consisting of Met, Trp, Ser, Ala, Leu, Val, Ile, Tyr, Asn, Arg, Lys and Pro;

$X_{10}$ is selected from the group consisting of Thr, Ala, Leu, Met, Arg, Gln, Trp, Val, His and Glu;

$X_{11}$ is selected from the group consisting of Arg, Thr, Asn, Glu, Trp, Phe, Asp, Met, Tyr, Gly, Gln, His, Leu, Ser and Ala;

$X_{12}$ is selected from the group consisting of Ile, His, Ala, Asn, Ser, Met, Val, Gly, Arg, Asp and Phe;

$X_{14}$ is selected from the group consisting of Ile, Tyr, Asn, Arg, Phe, Pro, Gln, Ala, Met, His, Ser, Gly, Asp, Glu and Leu;

(b) region 2 (amino acids 35-49) wherein the polypeptide comprises the structure:

(SEQ ID NO: 173)
$X_{35}-X_{36}-X_{37}-X_{38}-X_{39}-X_{40}-X_{41}-X_{42}-X_{43}-X_{44}-X_{45}-X_{46}-X_{47}$, wherein, $X_{35}$ is Gln;

$X_{37}$ is Asp;

$X_{42}$ is selected from the group consisting of Thr, Ser, Lys, Phe, Ile, Tyr, Asn, and Gly;

$X_{44}$ is selected from the group consisting of Val, Phe, Thr, Asn, Leu, Ser, and Tyr;

X$_{46}$ is selected from the group consisting of Asp, Val, Thr, Asn, Phe, Gly, Ser and Ile;
X$_{47}$ is selected from the group consisting of Thr, Arg, Trp, Phe, Arg, Lys, Ala, and Val;
X$_{48}$ is selected from the group consisting of Gln, Asn, Thr, Met, Leu, Asp, Arg, and Trp;
X$_{49}$ is selected from the group consisting of Arg, Leu, Pro, Lys, Thr, Ile, His, Phe, and Glu; and
(c) region 3 (amino acids 62-78) wherein the polypeptide comprises the structure:

(SEQ ID NO: 173)
X$_{62}$-X$_{63}$-X$_{64}$-X$_{65}$-X$_{66}$-X$_{67}$-X$_{68}$-X$_{69}$-X$_{70}$-X$_{71}$-X$_{72}$-X$_{73}$-

X$_{74}$-X$_{75}$-X$_{76}$-X$_{77}$-X$_{78}$, wherein,
X$_{62}$ is selected from the group consisting of His, Ser, Leu, Pro, Arg, Gly, Lys, Glu, Asn, Tyr and Val;
X$_{63}$ is selected from the group consisting of Asn, Arg, Lys, Pro, Thr, Met, Tyr, Gln, Gly, Trp, His and Leu;
X$_{64}$ is selected from the group consisting of His, Val, Ile, Arg, Ser, Trp, Asp, Tyr, Lys, Gln, Phe, Gly, Ala, Thr, Leu and Asn;
X$_{66}$ is selected from the group consisting of Ala and Tyr;
X$_{68}$ is selected from the group consisting of Tyr, Phe, Ala, Arg, Pro, Gly, Lys, Leu, Ser, Gln, Asp, and Asn;
X$_{70}$ is selected from the group consisting of Leu, Lys, Phe, Trp, Ala, Gly, Met, and Ile;
X$_{71}$ is selected from the group consisting of Phe, Met, Val, Lys, Gly, Arg, Trp, Ser, Ala, Thr and Ile;
X$_{72}$ is selected from the group consisting of Lys, Thr, Ile, Trp, Ser, Met and Gly;
X$_{73}$ is selected from the group consisting of Met, Phe, Asp, Ile, Pro, Arg, His and Val;
X$_{74}$ is selected from the group consisting of Trp, Leu, Tyr, His, Phe, Ser, Pro, Ile, Gly and Thr;
X$_{75}$ is selected from the group consisting of Ser, Arg, Ala, Leu, Val, Thr, Asp, Trp and Phe;
X$_{76}$ is selected from the group consisting of His, Glu, Val, Gln, Leu, Cys, Asn, Ala, Trp, Ile, Arg, Tyr, Met, Thr Asp and Lys;
X$_{77}$ is selected from the group consisting of Arg, Lys, Ala, Ile, Ser, Asp, Asn, Phe, Glu, Trp, Gln, His, Leu, Val, Tyr, Thr and Met; and
X$_{78}$ is selected from the group consisting of Arg, Thr, Ala, Gln, His, Lys, Met, Val, Leu, Ile, Phe, Cys, Glu, Tyr, Ser, Asn and Pro.

In some aspects of the disclosed methods, the ubiquitin binding partner comprises an amino acid mutation at position 2, 4, 6, 8, 9, 10, 11, 12, 14, 35, 37, 39, 40, 42, 44, 46, 47, 48, 49, 62, 63, 64, 66, 68, 70, 71 or 72 in the amino acid sequence of ubiquitin set forth in SEQ ID NO: 1. In some other aspects of the disclosed methods, the ubiquitin binding partner comprises an amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 in the amino acid sequence of a ubiquitin variant set forth in SEQ ID NO: 21.

Accordingly, in more specific aspects, the present disclosure provides a method of producing enzyme-specific inhibitors comprising: a) identifying active site residues of a substrate in an enzyme-substrate complex; b) randomizing the active site residues to produce a combinatorial library of substrate variants; and c) selecting substrate variants that inhibit enzyme activity.

The present disclosure also includes uses of the ubiquitin variants described herein for methods of inducing cell death in various cell types. In some aspects, the cell death is apoptosis. In some aspects, the ubiquitin variants described herein are used in the treatment of cancer or in a medicament for the treatment of cancer.

In further aspects, the ubiquitin variants described herein are used in screening small molecule libraries for inhibitors of the ubiquitin pathway, including inhibitors of USPs, OTUs, E3 ligases and E2-conjugating enzymes.

In more specific aspects, the active site residues of ubiquitin comprise regions 1-3 as shown in FIGS. 1A-1B.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

(FIG. 1A) The library design mapped onto the Ub structure (PDB entry 1 UBQ). The Ub main-chain is shown as a black tube and positions that were diversified in the library are shown as spheres, highlighted as follows: region 1 (light gray), region 2 (gray), region 3 (dark gray). (FIG. 1B) The primary sequence of the regions targeted in the library design. Diversified sequences are shaded and highlighted as in panel A.

FIGS. 2A-2B shows the sequences and specificity profiles of Ub variants. (FIG. 2A) Sequence alignment of Ub.wt (SEQ ID NO: 1) and Ub variants selected for binding to USP8 or USP21. The alignment shows only those positions that were diversified in the Ub library, and positions that were conserved as the wt sequence are indicated by dashes. (FIG. 2B) The Ub variants were assayed by phage ELISA for binding to the following immobilized USP proteins: USP2 (downward diagonal), USP7 (upward diagonal), USP8 (black), USP10 (grid), USP21 (gray). Bound phage were detected spectrophotometrically (optical density at 450 nm) and background binding to neutravidin was subtracted from the signal.

(FIG. 3A) The activity of USP8 (white bars) or USP21 (grey bars) in the presence of 1.0 μM Ub.wt (SEQ ID NO: 1), Ubv.8.2 (SEQ ID NO: 2) or Ubv.21.3 (SEQ ID NO: 6). The activity of USP8 (1.0 nM) or USP21 (25 nM) was measured with Ub-AMC substrate at 1.0 μM, and is normalized to the activity in the absence of Ub variants. Dose response curves for the activity of USP21 (FIG. 3B) or USP8 (FIG. 3C) (right panel) in the presence of varying concentrations of Ubv.8.2 (SEQ ID NO: 2) or UBv.21.3 (SEQ ID NO: 6), respectively. The IC$_{50}$ value was determined as the concentration of Ub variant that reduced USP activity by 50%. The activity of USP8 (1.0 nM) or USP21 (25 nM) was measured with Ub-AMC substrate at 1.0 μM, and is normalized to the activity in the absence of Ub variants.

(FIG. 4A) USP21 in complex with the Ubv.21.4 (SEQ ID NO: 7) (FIG. 4B) USP8 in complex with Ubv.8.2 (SEQ ID NO: 2).

FIGS. 5A-5B shows phage-derived Ub variants are potent and specific inhibitors of USP2. (FIG. 5A) Sequence alignment of Ub.wt variant comprising two additional C-terminal amino acids (two glycines at positions 76a and 76b, i.e., amino acids 77 and 78 of SEQ ID NO: 21) with phage-derived variants that bind USP2. The alignment shows only those randomized positions that were divergent from Ub.wt (SEQ ID NO: 1), and positions that were conserved as the wt sequence are indicated by dashes. (FIG. 5B) ELISA demonstrating binding specificity of Ub variants to various USPs, UIMs, ITCH, and NEDD4. Selected phages were tested against Ub-binding domains.

FIGS. 6A-6B shows phage-derived Ub variants are potent and specific inhibitors of USP5. (FIG. 6A) Sequence alignment of Ub.wt variant comprising two additional C-terminal amino acids (two glycines at positions 76a and 76b, i.e., amino acids 77 and 78 of SEQ ID NO: 21) with phage-derived variants that bind USP5. The alignment shows only those randomized positions that were divergent from Ub.wt (SEQ ID NO: 1), and positions that were conserved as the wt sequence are indicated by dashes. (FIG. 6B) ELISA demonstrating binding specificity of selected Ubv, i.e. ubiquitin enzyme inhibitors, with binding activity to USP5. Phage shows intrinsically non-specific binding to USP2a, explaining the high binding signal of selected Ubvs with binding activity to USP5.

(FIG. 7A) Sequence alignment of Ub.wt variant (SEQ ID NO: 21) with variant that binds USP10. The alignment shows only the 17 randomized positions that were divergent from Ub.wt (SEQ ID NO: 1). (FIG. 7B) ELISA demonstrating binding specificity of Ubv.10.1 (SEQ ID NO: 69) to USP10.

FIGS. 8A-8B shows the identification of five Ub variants (Ubv.48.01-Ubv.48.05 (SEQ ID NOs: 70-74, respectively)) as potent and specific inhibitors of USP48. (FIG. 8A) Sequence alignment of Ub.wt variant (SEQ ID NO: 21) with variants that bind USP48. The alignment shows only those randomized positions that were divergent from Ub.wt (SEQ ID NO: 1), and positions that were conserved as the wt sequence are indicated by dashes. (FIG. 8B) ELISA demonstrating binding specificity of Ubv to USP48.

FIGS. 9A-9B shows the identification of Ub variants as potent and specific inhibitors of Nedd4. (FIG. 9A) Sequence alignment of Ub.wt variant (SEQ ID NO: 21) with variants that binds Nedd4. Positions that were conserved as the wt sequence are indicated by dashes (FIG. 9B) ELISA demonstrating binding specificity of Ubvs to Nedd4.

FIGS. 10A-10B shows the identification of Ub variants as potent and specific inhibitors of ITCH. (FIG. 10A) Sequence alignment of Ub.wt variant (SEQ ID NO: 21) with variants that binds ITCH. Positions that were conserved as the wt sequence are indicated by dashes. (FIG. 10B) ELISA demonstrating binding specificity of Ubvs to ITCH.

FIGS. 11A-11D shows the identification of Ub variants as potent and specific inhibitors of UIM. (FIG. 11A) Sequence alignment of Ub.wt variant (SEQ ID NO: 21) with variants that binds UIM. Positions that were conserved as the wt sequence are indicated by dashes. (FIGS. 11B-D) ELISA demonstrating binding specificity of Ubvs to UIMs (peptides designated Rensselaer Polytech George Makhadatze (RPGM)-1, RPGM-2, and RPGM-3, (UIM1, UIM1a, and UIM1b, respectively) from Rensselaer Polytechnic Institute).

FIGS. 12A-12B shows the identification of additional Ub variants as potent and specific inhibitors of USP8. (FIG. 12A) Sequence alignment of Ub.wt variant (SEQ ID NO: 21) with variants that binds USP8. Positions that were conserved as the wt sequence are indicated by dashes. (FIG. 12B) ELISA demonstrating binding specificity of Ubvs to USP8.

FIGS. 13A-13B shows the identification of additional Ub variants as potent and specific inhibitors of USP21. (FIG. 13A) Sequence alignment of Ub.wt variant (SEQ ID NO: 21) with variants that binds USP21. Positions that were conserved as the wt sequence are indicated by dashes. (FIG. 13B) ELISA demonstrating binding specificity of Ubvs to USP21.

(FIG. 15A) NF-κB and control *Renilla luciferase* reporter plasmids were co-transfected into HEK293T cells with increased amounts of expression plasmid for USP21; 36 hours later, transfected cells were treated with TNFα for 6 hours. NF-κB activation in the cells was determined by measuring luciferase activity in the cell lysates. (FIG. 15B) NF-κB and control *Renilla luciferase* reporter plasmids were co-transfected into HEK293T cells with expression plasmid for RIP1 as well as increased amounts of expression plasmid for USP21; 36 hours later, NF-κB activation in the cells was determined by measuring luciferase activity in the cell lysates. (FIG. 15C) NF-κB and control *Renilla* luciferase reporter plasmids were co-transfected into HEK293T cells with expression plasmid for USP21 as well as increased amounts of expression plasmid for Ubv.21.4 (SEQ ID NO: 7) or Ub.wt (SEQ ID NO: 1); 36 hours later, cells were treated with TNFα for 6 hours. NF-κB activation in the cells was determined by measuring luciferase activity in the cell lysates. (FIG. 15D) NF-κB and control *Renilla* luciferase reporter plasmids were co-transfected into HEK293T cells with expression plasmid for RIP1 and USP21 as well as increased amounts of expression plasmid for Ubv.21.4 (SEQ ID NO: 7) or Ub.wt (SEQ ID NO: 1); 36 hours later, NF-κB activation in the cells was determined by measuring luciferase activity in the cell lysates. (FIG. 15E) Expression plasmids for RIP1 and USP21 were co-transfected with increased amounts of expression plasmid for Ubv.21.4 (SEQ ID NO: 7) or Ub.wt (SEQ ID NO: 1); 36 hours later, RIP1 polyubiquitination was determined by immunoblotting of cell lysates with anti-RIP1 antibody. (FIG. 15F) Expression plasmid for vector control or Myc-USP21 was co-transfected into HEK293T cells with expression plasmid for Flag-Ubv.21.4 (SEQ ID NO: 7) or Ub.wt (SEQ ID NO: 1); 36 hours later, immunoprecipitations were performed with anti-Myc antibody for Myc-USP21, followed by immunoblotting with anti-Flag antibody for Flag-Ub.

DETAILED DESCRIPTION OF THE DISCLOSURE

Definitions

Figures 1A, 1B:
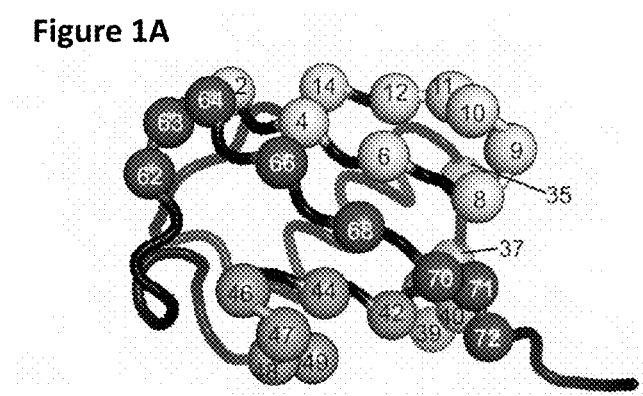
FIGS. 1A-1B shows the Ub library design.

The term "active site" as used herein refers to the surface exposed residues of the substrate which are located in the substrate binding site of the enzyme or the substrate binding partner.

The term "analog" as used herein includes any active agent capable of performing the function of the enzyme inhibitors or substrate binding partners disclosed herein, and may include peptide mimetics and the like.

The term "allosteric inhibition" as used herein refers to a change in the shape of the active site of an enzyme or substrate binding partner when an inhibitor binds to it. For example, an allosteric inhibitor changes the shape of the active site such that the substrate is no longer able to bind the enzyme or substrate binding partner.

The term "cofactor" as used herein refers to non-protein molecules that must be associated with certain enzymes for such enzymes to function. Cofactors can be inorganic compounds, such as metal ions or organic compounds, such as flavin or heme.

The term "combinatorial library" as used herein refers to a collection of substrate variants that have been randomized or mutated in the active site.

The term "competitive inhibition" as used herein refers to competition between the variant and the substrate for the enzyme or the substrate binding partner, for example, competition for binding of the enzyme where only one can bind at a time.

A "conservative amino acid substitution" as used herein, is one in which one amino acid residue is replaced with another amino acid residue without abolishing the desired function or activity of the enzyme inhibitors or substrate variants disclosed herein. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Conserved amino acid substitutions involve replacing one or more amino acids of the polypeptides of the disclosure with amino acids of similar charge, size, and/or hydrophobicity characteristics. When only conserved substitutions are made the resulting molecule should be functionally equivalent. Changes which result in production of a chemically equivalent or chemically similar amino acid sequence are included within the scope of the disclosure. If the enzyme inhibitors or substrate variants of the present disclosure are made using recombinant DNA technology, conservative substituted variants of the enzyme inhibitors or substrate variants may be made by using polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine. The phrase "conservative substitution" also includes the use of a chemically derivatized residue in place of a non-derivatized residue provided that such polypeptide displays the requisite activity.

The term "control" as used herein refers to a positive control such as a protein known to inhibit the enzyme or a negative control such as a protein known not to inhibit the enzyme, the wild type substrate or an absence of inhibitor. The term also includes a predetermined standard.

The term "derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. A derivative of a polypeptide also optionally includes polypeptides comprising forms of amino acids that are oxidized.

The term "enzyme" as used herein refers to a protein or protein-based molecule that catalyzes a specific reaction in a living organism, converting a substrate or substrates into a product or products. For example, an enzyme provides a binding surface that mediates high specificity for its substrate and associated cofactors and also allows release of the reaction products. Enzymes regulate a wide variety of processes in a living organism, including without limitation, signal transduction, cell regulation, cell movement, cell death and protein degradation. Typical enzymes include transferases, anhydrases, synthases, synthetases, polymerases, hydrolases, such as proteases, lyases, and ligases. In various aspects of the disclosure, the term "enzyme" includes ubiquitin-specific proteases (USPs) and ubiquitin ligases.

The term "enzyme-substrate complex" as used herein refers to the complex formed when a substrate molecule binds with the active site of an enzyme and optionally, a cofactor. In addition, the term "substrate binding partner-substrate complex" as used herein is formed when a substrate molecule binds with the active site of a protein interacting motif, which in some aspects may be parts of larger proteins. For example, in more particular aspects, ubiquitin or ubiquitin variants interact with ubiquitin interaction motifs (UIM).

The term "fragment" as used herein means a portion of a polypeptide that contains at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or more of the entire length of the reference polypeptide.

The term "isolated and purified" as used herein refers to a nucleic acid or amino acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e. sequences located at the 5' and 3' ends of the nucleic acid) from which the nucleic acid is derived.

The term "nucleic acid" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present disclosure may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The term "product" as used herein refers to the resulting compound or compounds produced by an enzyme from its substrate.

The term "substrate" as used herein refers to a molecule at the beginning of an enzymatic reaction i.e. the substance that is acted upon by an enzyme or binds to a substrate binding partner. In some aspects, the term substrate is used herein to identify ubiquitin or a ubiquitin variant.

The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the disclosure. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

The term "ubiquitin" or "Ub" as used herein refers to ubiquitin from any species or source and includes the full-length protein as well as fragments or portions of the protein. Human ubiquitin has the amino acid sequence as shown in SEQ ID NO: 1 and has the Genbank Accession No. for poly-ubiquitin of: BAA23486 and for the ubiquitin isoform C of: EAX04505.

The term "ubiquitin variant" or "Ubv" as used herein refers to a ubiquitin polypeptide that comprises at least one amino acid substitution, deletion, insertion, addition, or modification with respect to the native or wildtype (wt) ubiquitin polypeptide of SEQ ID NO: 1. In some aspects, a ubiquitin variant, Ub.wt variant, comprising two additional C-terminal amino acids (two glycines at positions 76a and 76b, i.e., amino acids 77 and 78 of SEQ ID NO: 21) is used in the methods described herein to identify ubiquitin enzyme inhibitors or ubiquitin variants that bind ubiquitin interaction motifs.

The term "ubiquitin enzyme" as used herein refers to an enzyme whose substrate is ubiquitin and includes, without limitation, Ub-activating enzymes (E1 enzymes), Ub-conjugating enzymes (E2 enzymes), Ub ligase (E3 enzymes) and deubiquitinating enzymes (DUBs).

Compounds of the Disclosure

Exemplary ubiquitin inhibitors are provided in Tables 1-10.

TABLE 1

UBIQUITIN INHIBITORS WITH BINDING SPECIFICITY TO USP8 and USP21

| UBIQUITIN VARIANT | SEQ ID NO | SEQUENCE |
|---|---|---|
| Ubv.8.2 | 2 | MRIVVKTLMGRTIILEVEPSDTIENVKAKI QDKEGIPPDQQRLIFAGKQLEDGRTLSDYN IHNHSALYLLLKLRGG |
| Ubv.8.3 | 3 | MYIFVKTFMGRTIYLEVEPSDTIENVKAKI QDKEGIPPDQQRLIFAGKQLEDGRTLSDYN ISKVSALYLLFRLRGG |
| Ubv.21.1 | 4 | MQIFVKTLTGKTITLEVEPSDTIENVKAKI QDKEGIPPDQQRLIFAGKQLEDGRTLSDYN IQKISTLFLLMRLRGG |
| Ubv.21.2 | 5 | MQIFVKTLTGKTITLEVEPSDTIENVKAKI QDKEGIPPDQQRLIFAGKQLEDGRTLSDYN ILKRSTLFLLLKLRGG |
| Ubv.21.3 | 6 | MQIFVKTGTGKTIILEVEPSDTIENVKAKI QDKEGIPPDQQRLIFAGKQLEDGRTLSDYN ILKSSTLFLLLRLRGG |
| Ubv.21.4 | 7 | MQIFVKTLTGKTITLEVEPSDTIENVKAKI QDKEGIPPDQQRLIFAGKQLEDGRTLSDYN IQKWSTLFLLLRLRGG |
| Ubv.21.5 | 8 | MQIFVKTLTGKTITLEVEPSDTIENVKAKI QDKEGIPPDQQRLIFAGKQLEDGRTLSDYN IQKDSTLFLLLRLRGG |

TABLE 2

UBIQUITIN INHIBITORS WITH BINDING SPECIFICITY TO USP2

| UBIQUITIN VARIANT | SEQ ID NO | SEQUENCE |
|---|---|---|
| USP2-A1 | 22 | MQIFVKTLTGKTITLEVEPSDTIENVKAKI QDKEGIPPDQQRLIFAGKQLEDGRTLSDYN IQKESTLHLVMRLWSHRR |
| USP2-A10 | 23 | MQIFVNTLTGKTITLEVEPSDTIENVKAKI QDKEGIPPDQQRLIFAGKQLEDGRTLSDYN IQKESTLHLVLRLWSEGT |
| USP2-A12 | 24 | MQIFVMTLTGQNITLEVEPSDTIENVKAKI QDKEGIPPDQQRLIFAGKQLEDGRTLSDYN IQKESTLHLVLRLLSGGH |
| USP2-A3 | 25 | MQIFVKTLWTRTITLEVEPSDTIENVKAKI QDKEGIPPDQQRLIFAGKQLEDGRTLSDYN IQKESTLHLVLRLYGVKR |
| USP2-A6 | 26 | MQIFVKTLTGKTITLEVEPSDTIENVKAKI QDKEGIPPDQQRLIFAGKQLEDGRTLSDYN IQKESTLHLVLRLYGQAA |
| USP2-A7 | 27 | MDIFVNTITGKIITLEVEPSDTIENVKAKI QDKEGIPPDQQRLIFAGKQLEDGRTLSDYN IPRYSTLHLLLRLRGEIQ |
| USP2-A9 | 28 | MQIFVMTLTGKTITLEVEPSDTIENVKAKI QDKEGIPPDQQRLIFAGKQLEDGRTLSDYN IQKYSTLHLVLRLLGVSH |
| USP2-B10 | 29 | MQIFVYTLTGKTITLEVEPSDTIENVKAKI QDKEGIPPDQQRLIFAGKQLEDGRTLSDYN IQKESTLHLVLRLYSLDR |

TABLE 2-continued

UBIQUITIN INHIBITORS WITH BINDING SPECIFICITY TO USP2

| UBIQUITIN VARIANT | SEQ ID NO | SEQUENCE |
|---|---|---|
| USP2-B11 | 30 | MHIFVNTLTGKTITLEVEPSDTIENVKAKIQDKEGIPPDQQRLIFAGKQLEDGRTLSDYNIQKESTLHLVLRLWSCKG |
| USP2-B12 | 31 | MQIFVKTLSGRTITLEVEPSDTIENVKAKIQDKEGIPPDQQRLIFAGKQLEDGRTLSDYNIQKESTLHLVLRLLSGRK |
| USP2-B7 | 32 | MQIFVNTLTGTHITLEVEPSDTIENVKAKIQDKEGIPPDQQRLIFAGKQLEDGRTLSDYNIQKESTLHLVLRLGGGG |
| USP2-B8 | 33 | MQIFVMTLTGKHITLEVEPSDTIENVKAKIQDKEGIPPDQQRLIFAGKQLEDGRTLSDYNIQKESTLHLVLRLGGGG |
| USP2-C10 | 34 | MQIFVKTLTGKTITLEVEPSDTIENVKAKIQDKEGIPPDQQRLIFAGKQLEDGRTLSDYNIQKESTLHLVLRLHSNAM |
| USP2-C11 | 35 | MQIFVKTIAGKAITLEVEPSDTIENVKAKIQDKEGIPPDQQRLIFAGKQLEDGRTLSDYNIQKESTLHLVLRLLSGKR |
| USP2-C3 | 36 | MQIFVNTLSGKHITLEVEPSDTIENVKAKIQDKEGIPPDQQRLIFAGKQLEDGRTLSDYNIQKESTLHLVLRLGGGG |
| USP2-C5 | 37 | MQIFVNTLTGKTITLEVEPSDTIENVKAKIQDKEGIPPDQQRLIFAGKQLEDGRTLSDYNIQKESTLHLVLRLFSARV |
| USP2-C7 | 38 | MQIFVNTLTGRHITLEVEPSDTIENVKAKIQDKEGIPPDQQRLIFAGKQLEDGRTLSDYNIQKESTLHLVLRLGGGG |
| USP2-C8 | 39 | MQIFVKTLTGKTITLEVEPSDTIENVKAKIQDKEGIPPDQQRLIFAGKQLEDGRTLSDYNIHKESTLHLVLRLLSGRR |
| USP2-C9 | 40 | MQIFVNTLTGKTITLEVEPSDTIENVKAKIQDKEGIPPDQQRLIFAGKQLEDGRTLSDYNIKKESTLHLVLRLWSWRR |
| USP2-D1 | 41 | MQIFVNTLTARNITLEVEPSDTIENVKAKIQDKEGIPPDQQRLIFAGKQLEDGRTLSDYNIQKESTLFLVLRLRSENL |
| USP2-D11 | 42 | MQIFVKTLTGKTITLEVEPSDTIENVKAKIQDKEGIPPDQQRLIFAGKQLEDGRTLSDYNIQKESTLHLVLRLLSGSI |
| USP2-D3 | 43 | MDIFVNTLTGNTITLEVEPSDTIENVKAKIQDKEGIPPDQQRLIFAGKQLEDGRTLSDYNIQKESTLHLVLRLGGGG |
| USP2-D4 | 44 | MEIFVKTLTGKTITLEVEPSDTIENVKAKIQDKEGIPPDQQRLIFAGKQLEDGRTLSDYNIQKESTLHLVLRLWSISF |
| USP2-D6 | 45 | MQIFVKTLTGKTITLEVEPSDTIENVKAKIQDKEGIPPDQQRLIFAGKQLEDGRTLSDYNIQKESTLHLVLRLLSRSK |
| USP2-D7 | 46 | MQIFVKTLTGKTITLEVEPSDTIENVKAKIQDKEGIPPDQQRLIFAGKQLEDGRTLSDYNIQKESTLHLVLRLLGYSK |
| USP2-D9 | 47 | MNIFVKTLAGNHITLEVEPSDTIENVKAKIQDKEGIPPDQQRLIFAGKQLEDGRTLSDYNIQKESTLHLVLRLGGGG |

TABLE 3

UBIQUITIN INHIBITORS WITH BINDING SPECIFICITY TO USP5

| UBIQUITIN VARIANT | SEQ ID NO | SEQUENCE |
|---|---|---|
| USP5-E4 | 48 | MEIYVNTRLLETINLEVEPSDTIENVKAKIQDKEGIPPDQQRLIFAGKQLEDGRTLSDYNIQKKSTLYLVLRLLGQRH |
| USP5-F11 | 49 | MQIFVQTRVMNTITLEVEPSDTIENVKAKIQDKEGIPPDQQRLIFATKQLEDGRTLSDYNIHKDSTLHLLLRMRRLNK |
| USP5-F3 | 50 | MQIFVQTRAMWTITLEVEPSDTIENVKAKIQDKEGIPPDQQRLIFAGKQLEDGRTLSDYNIPKESTLHLVLRLGGGG |
| USP5-F7 | 51 | MQIFVNTRTMFTIRLEVEPSDTIENVKAKIQDKEGIPPDQQRLIFAGKQLEDGRTLSDYNIQKESTLHLVLRLGGGG |
| USP5-F8 | 52 | MRIFVKTRMMESIFLEVEPSDTIENVKAKIQDKEGIPPDQQRLIFAGQQLEDGRTLSDYNIQKESTLHLVVRFRSARR |
| USP5-F9 | 53 | MPIFVNTRWMKTIPLEVEPSDTIENVKAKIQDKEGIPPDQQRLIFDRKQLEDGRTLSDYNIQKESTLHLVLRDLGVFC |
| USP5-G10 | 54 | MQIMVHTRVMNSITLEVEPSDTIENVKAKIQDKEGIPPDQQRLIFAGKQLEDGRTLSDYNIQKESTLHLVLRLGGGG |
| USP5-G11 | 55 | MQISVNTRMMESITLEVEPSDTIENVKAKIQDKEGIPPDQQRLIFAGKQLEDGRTLSDYNILPESTLHLVLRLGGGG |
| USP5-G3 | 56 | MQIVVNTRMMETITLEVEPSDTIENVKAKIQDKEGIPPDQQRLIFAGKQLEDGRTLSDYNIQKESTLHLVLRLGGGG |
| USP5-G4 | 57 | MHIFVNTRIMETITLEVEPSDTIENVKAKIQDKEGIPPDQQRLIFAGKQLEDGRTLSDYNIQKESTLHLVLRLGGGG |
| USP5-G5 | 58 | MHISVNTRSMWTIQLEVEPSDTIENVKAKIQDKEGIPPDQQRLIFAGKQLEDGRTLSDYNIQKESTLHLVLRLGGGG |
| USP5-G6 | 59 | MQIFVHTRMMETITLEVEPSDTIENVKAKIQDKEGIPPDQQRLIFAGKQLEDGRTLSDYNIHKESTLHLVLRLGGGG |
| USP5-G8 | 60 | MQIIVRTRAMWTIALEVEPSDTIENVKAKIQDKEGIPPDQQRLIFAGKQLEDGRTLSDYNIRTESTLHLVLRLGGGG |
| USP5-G9 | 61 | MQIFVNTRMMDSIMLEVEPSDTIENVKAKIQDKEGIPPDQQRLIFAGKQLEDGRTLSDYNIQKESTLHLVLRLGGGG |
| USP5-H10 | 62 | MQIFVNTRMMTITLEVEPSDTIENVKAKIQDKEGIPPDQQRLIFAGKQLEDGRTLSDYNIQKESTLHLVLRLGGGG |
| USP5-H11 | 63 | MQIVVNTRSMNTIHLEVEPSDTIENVKAKIQDKEGIPPDQQRLIFAGKQLEDGRTLSDYNIQKRSTLYLVLRLGGGG |
| USP5-H12 | 64 | MRIVVNTRYMNTISLEVEPSDTIENVKAKIQDKEGIPPDQQTLIFAGKQLEDGRTLSDYNIHKESTLHLVLRLGGGG |
| USP5-H4 | 65 | MQIFVNTRLMYSITLEVEPSDTIENVKAKIQDKEGIPPDQQRLIFAGKQLEDGRTLSDYNIQKESTLHLVLRISRGLP |

TABLE 3-continued

UBIQUITIN INHIBITORS WITH BINDING SPECIFICITY TO USP5

| UBIQUITIN VARIANT | SEQ ID NO | SEQUENCE |
|---|---|---|
| USP5-H7 | 66 | MQILVRTRIMETITLEVEPSDTIENVKAKI QDKEGIPPDQQRLIFAGNQLEDGRTLSDYN IQKESTLHLVLRLGGGG |
| USP5-H8 | 67 | MQIFVNTRMMETIALEVEPSDTIENVKAKI QDKEGIPPDQQSLIFAGKRLEDGRTLSDYN IQKSSTLHLVLRLGGGG |
| USP5-H9 | 68 | MQIFVNTRMMNTIDLEVEPSDTIENVKAKI QDKEGIPPDQQRLIFAGKQLEDGRTLSDYN IQKESTLHLVLRLGGGG |

TABLE 4

UBIQUITIN INHIBITORS WITH BINDING SPECIFICITY TO USP10

| UBIQUITIN VARIANT | SEQ ID NO | SEQUENCE |
|---|---|---|
| Ubv.10.1 | 69 | MQIFVETPMGKTIALEVEPSDTIENVKAKI QDKEGIPPDQQRLVFVGKLLEDGRTLSDYN IQRWSTLALKFRLLAKNL |

TABLE 5

UBIQUITIN INHIBITORS WITH BINDING SPECIFICITY TO USP48

| UBIQUITIN VARIANT | SEQ ID NO | SEQUENCE |
|---|---|---|
| USP48-Ubv.48.01 | 70 | MQIIVKTLTGGTIGLEVEPSDTIENVKAKI QDKEGIPPDQQRLFFAWTPLEDGRTLSDYN IQMESTLRLFLRPRGLKE |
| USP48-Ubv.48.02 | 71 | MQISVKTLTGNMITLEVEPSDTIENVKAKI QDKEGIPPDQQRLTFVFKQLEDGRTLSDYN IGKHSTLHLWLRLLGIGK |
| USP48-Ubv.48.03 | 72 | MQIFVKTLNGNIISLEVEPSDTIENVKAKI QDKEGIPPDQQRLFFAWKQLEDGRTLSDYN IPKESTLPLFLRLGGGG |
| USP48-Ubv.48.04 | 73 | MQISVKTLTGGTITLEVEPSDTIENVKAKI QDKEGIPPDQQRLFFAFTPLEDGRTLSDYN IGKQSTLHLWLRLLGLEE |
| USP48-Ubv.48.05 | 74 | MRIFVETLTGQIINLEVEPSDTIENVKAKI QDKEGIPPDQQRLNFAGKLLEDGRTLSDYN IKKWSTLHLVLRLGGGG |

TABLE 6

UBIQUITIN INHIBITORS WITH BINDING SPECIFICITY TO NEDD4

| UBIQUITIN VARIANT | SEQ ID NO | SEQUENCE |
|---|---|---|
| Nedd4-N4-A11 | 75 | MLILVKTLTGHSITLEVEPSDTIENVKAKI QDKEGIPPDQQRLFFAGKQLEDGRTLSDYN IHKFSTLHLVKRLRGRWK |

TABLE 6-continued

UBIQUITIN INHIBITORS WITH BINDING SPECIFICITY TO NEDD4

| UBIQUITIN VARIANT | SEQ ID NO | SEQUENCE |
|---|---|---|
| Nedd4-N4-A9 | 76 | MRIFVTTLTGRAITLEVEPSDTIENVKAKI QDKEGIPPDQQRLIFTGKKLEDGRTLSDYN IPKESTLYLVKRLRGMEQ |
| Nedd4-N4-B1 | 77 | MHIFVRTLTRKIITLEVEPSDTIENVKAKI QDKEGIPPDQQRLFFTGMTLEDGRTLSDYN IQKESTLHLVLRLRGGGG |
| Nedd4-N4-B10 | 78 | MRILVKTLTRKVITLEVEPSDTIENVKAKI QDKEGIPPDQQRLIFAGQRLEDGRTLSDYN IQKESTLHLVLRLRGGGG |
| Nedd4-N4-B4 | 79 | MQIFVKTMRRESISLEVEPSDTIENVKAKI QDKEGIPPDQQRLFFTGKQLEDGRTLSDYN IQKESTLHLVKRLPGRQY |
| Nedd4-N4-B5 | 80 | MQIVVKTLSRRTIGLEVEPSDTIENVKAKI QDKEGIPPDQQRLIFAGKKLEDGRTLSDYN IQKESTLHLALKLPGMGG |
| Nedd4-N4-B6 | 81 | MQIFVKTFTGKSITLEVEPSDTIENVKAKI QDKEGIPPDQQRLIFDRNKLEDGRTLSDYN IKKESTLGLVLRLRGGGG |
| Nedd4-N4-C1 | 82 | MQILVQTLTRKTITLEVEPSDTIENVKAKI QDKEGIPPDQQRLFFAGTQLEDGRTLSDYN IQKHSTLYLVLRLLGRRH |
| Nedd4-N4-C10 | 83 | MQILVKTLTGKTITLEVEPSDTIENVKAKI QDKEGIPPDQQRLIFAGLKLEDGRTLSDYN IQKVSTLYLVKTFPGRRQ |
| Nedd4-N4-C11 | 84 | MQIFVKTLAGWGITLEVEPSDTIENVKAKI QDKEGIPPDQQRLIFAGKQLEDGRTLSDYN IRYDSTLHLVGRLRGGGG |
| Nedd4-N4-C12 | 85 | MQILVKTLARTSIILEVEPSDTIENVKAKI QDKEGIPPDQQRLIFAGKQLEDGRTLSDYN IQKESTLHLVLRLRGGGG |
| Nedd4-N4-C2 | 86 | MQIFVKTLTGKTITLEVEPSDTIENVKAKI QDKEGIPPDQQRLIFAGKQLEDGRTLSDYN IQKDSTLHLVRRLPRMGK |
| Nedd4-N4-C4 | 87 | MYISVKTLTGESISLEVEPSDTIENVKAKI QDKEGIPPDQQKLFFAGKILEDGRTLSDYN ILKWSTLHLVKRLRAVHM |
| Nedd4-N4-C5 | 88 | MQIFVKTLTRKTITLEVEPSDTIENVKAKI QDKEGIPPDQQRLIFAGKRLEDGRTLSDYN IQKESTLHLVLRLRGGGG |
| Nedd4-N4-C6 | 89 | MPIVVKTLAGYTIHLEVEPSDTIENVKAKI QDKEGIPPDQQKLLFAGNRLEDGRTLSDYN IHNGSTLYLVKRLRGGGG |
| Nedd4-N4-D1 | 90 | MQIFVNTLARTSISLEVEPSDTIENVKAKI QDKEGIPPDQQRLIFAGKQLEDGRTLSDYN IQKESTLHLVLRLPGTKV |
| Nedd4-N4-D10 | 91 | MQIFVRTLMRKSISLEVEPSDTIENVKAKI QDKEGIPPDQQKLIFAGKLLEDGRTLSDYN IQKESTLHLVKKLILLRE |
| Nedd4-N4-D11 | 92 | MQIFVKTLTGKTITLEVEPSDTIENVKAKI QDKEGIPPDQQRLIFAGKQLEDGRTLSDYN IQKESTLHLVLRLRGGGG |
| Nedd4-N4-D12 | 93 | MQIYVKTLTRKRITLEVEPSDTIENVKAKI QDKEGIPPDQQKLFFNGKQLEDGRTLSDYN IQKESTLHLVLRLRGGGG |

TABLE 6-continued

UBIQUITIN INHIBITORS WITH BINDING SPECIFICITY TO NEDD4

| UBIQUITIN VARIANT | SEQ ID NO | SEQUENCE |
|---|---|---|
| Nedd4-N4-D2 | 94 | MQIYVKTLTRKTITLEVEPSDTIENVKAKI QDKEGIPPDQQRLIFVGKQLEDGRTLSDYN IQKESTLYLVLRLRGGGG |
| Nedd4-N4-D3 | 95 | MKISVNTLTGKTITLEVEPSDTIENVKAKI QDKEGIPPDQQRLIFAGKQLEDGRTLSDYN IQKYSTLYLVKRLRRLKQ |
| Nedd4-N4-D5 | 96 | MQIFVPTLVQKAINLEVEPSDTIENVKAKI QDKEGIPPDQQRLFFFRKPLEDGRTLSDYN IKKESTLHLLWRFSSRLM |
| Nedd4-N4-D8 | 97 | MQIFVRTLTGKTITLEVEPSDTIENVKAKI QDKEGIPPDQQRLIFAKQQLEDGRTLSDYN ILKESTLGLVRRLRGLVS |
| Nedd4-N4-D9 | 98 | MQIFVKTLTGKTITLEVEPSDTIENVKAKI QDKEGIPPDQQRLIFAGKQLEDGRTLSDYN IQQVSTLYLVKRLRGGGG |

TABLE 7

UBIQUITIN INHIBITORS WITH BINDING SPECIFICITY TO ITCH

| UBIQUITIN VARIANT | SEQ ID NO | SEQUENCE |
|---|---|---|
| Ubv.ITCH.01 | 99 | MPILVKTLRGQSIILEVEPSDTIENVKAKI QDKEGIPPDQQFLIPARKHLEDGRTLSDYN IQKRSTLYLFLRFHGMVA |
| Ubv.ITCH.02 | 100 | MHILVKTLRGKTITLEVEPSDTIENVKAKI QDKEGIPPDQQRLLFGGNKLEDGRTLSDYN IQKESTLYLLLRRLGSKF |
| Ubv.ITCH.03 | 101 | MQIFVITHTWRTITLEVEPSDTIENVKAKI QDKEGIPPDQQRLLFARQKLEDGRTLSDYN IQKDSTLHLVLIRRVSKR |
| Ubv.ITCH.04 | 102 | MQIFVKTLTGLSITLEVEPSDTIENVKAKI QDKEGIPPDQQILIFGGKRLEDGRTLSDYN IQKKSTLYLLMRLRGVSR |
| Ubv.ITCH.05 | 103 | MQIFVKTLTGTDITLEVEPSDTIENVKAKI QDKEGIPPDQQILLFAGKQLEDGRTLSDYN IPGDSTLYLLMRFGVNKR |
| Ubv.ITCH.06 | 104 | MPILVQTLRGQSIILEVEPSDTIENVKAKI QDKEGIPPDQQFLIFARTHLEDGRTLSDYN IQKGSTLYLLLRFHGTVA |

TABLE 8

UBIQUITIN INHIBITORS WITH BINDING SPECIFICITY TO UIM

| UBIQUITIN VARIANT | SEQ ID NO | SEQUENCE |
|---|---|---|
| Ubv.UIM1.01 | 105 | MQILVKTVIVKTISLEVEPSDTIENVKAKI QDKEGIPPDQQTLIFAGMQLEDGRTLSDYN IRRASTLHLVGRLRGGGG |
| Ubv.UIM1.02 | 106 | MQIFVQTLIVKTIILEVEPSDTIENVKAKI QDKEGIPPDQQYLIFAGKQLEDGRTLSDYN IGMESTLRLVGRLRGGGG |
| Ubv.UIM1.03 | 107 | MPISVVTLIVKTITLEVEPSDTIENVKAKI QDKEGIPPDQQSLIFAGKQLEDGRTLSDYN IQNRSTLHLVGRLRGGGG |
| Ubv.UIM1.04 | 108 | MLIFVTTVRVSTITLEVEPSDTIENVKAKI QDKEGIPPDQQRLIFAGKQLEDGRTLSDYN ILKESTLKLVWIFRGNRT |
| Ubv.UIM1a.01 | 109 | MQILVKTVIVKTISLEVEPSDTIENVKAKI QDKEGIPPDQQTLIFAGMQLEDGRTLSDYN IRRASTLHLVGRLRGGGG |
| Ubv.UIM1a.02 | 110 | MEIVVQTLIVKSITLEVEPSDTIENVKAKI QDKEGIPPDQQRLIFGGDFLEDGRTLSDYN IQKESTLHLVSWLRGGGG |
| Ubv.UIM1a.03 | 111 | MQIIVETITVKTIALEVEPSDTIENVKAKI QDKEGIPPDQQRLIFAGKQLEDGRTLSDYN IHKESTLLLVSWLHGDRQ |
| Ubv.UIM1a.04 | 112 | MQIFVQTLIVKTIILEVEPSDTIENVKAKI QDKEGIPPDQQYLIFAGKQLEDGRTLSDYN IGMESTLRLVGRLRGGGG |
| Ubv.UIM1a.05 | 113 | MQIFVQTIVMRIALEVEPSDTIENVKAKI QDKEGIPPDQQRLIFAGMQLEDGRTLSDYN IKRDSTLYLVSSLRGLRA |
| Ubv.UIM1a.06 | 114 | MQIFVQTLTVKSITLEVEPSDTIENVKAKI QDKEGIPPDQQRLIFAGRQLEDGRTLSDYN IQKGSTLHLVAWLRGGGG |
| Ubv.UIM1b.01 | 115 | MRIFVKTITVKSIHLEVEPSDTIENVKAKI QDKEGIPPDQQTLIFAGKLLEDGRTLSDYN IKKESTLHLVAKHRGMEV |
| Ubv.UIM1b.02 | 116 | MQIFVKTLTVTTIYLEVEPSDTIENVKAKI QDKEGIPPDQQRLIFAGKQLEDGRTLSDYN IQKDSTLGLVLKFRALVR |
| Ubv.UIM1b.03 | 117 | MQIFVITFSGRTITLEVEPSDTIENVKAKI QDKEGIPPDQQNLIFGGRQLEDGRTLSDYN IQQVSTLLLVLSLRGTRE |
| Ubv.UIM1b.04 | 118 | MQIFVKTLAVKTIELEVEPSDTIENVKAKI QDKEGIPPDQQRLIFAGKQLEDGRTLSDYN IQKDSTLGLVLSVRVLRR |
| Ubv.UIM1b.05 | 119 | MQINVNTLMVKAITLEVEPSDTIENVKAKI QDKEGIPPDQQRLIFGAKQLEDGRTLSDYN IQKESTLYLVFSLRGKGQ |
| Ubv.UIM1b.06 | 120 | MLIFVKTLRVETITLEVEPSDTIENVKAKI QDKEGIPPDQQRLIFAGKQLEDGRTLSDYN IGKESTLGLVTRLRVYES |
| Ubv.UIM1b.07 | 121 | MTIFVTTIIVNTITLEVEPSDTIENVKAKI QDKEGIPPDQQRLIFAGKQLEDGRTLSDYN IKKESTLRLVSRHRRTVK |
| Ubv.UIM1b.08 | 122 | MHIFVKTLTVKTITLEVEPSDTIENVKAKI QDKEGIPPDQQRLIFVRQHLEDGRTLSDYN IQKESTLGLVLSLRGIAK |
| Ubv.UIM1b.09 | 123 | MQIFVGTLTVNGINLEVEPSDTIENVKAKI QDKEGIPPDQQRLFFAGKQLEDGRTLSDYN IQKESTLHLVLRLRGGGG |
| Ubv.UIM1b.10 | 124 | MQIFVKTLTVNTITLEVEPSDTIENVKAKI QDKEGIPPDQQKLIFAGKQLEDGRTLSDYN IQKDSTLGLVSRLRGGGG |

TABLE 8-continued

UBIQUITIN INHIBITORS WITH BINDING SPECIFICITY TO UIM

| UBIQUITIN VARIANT | SEQ ID NO | SEQUENCE |
|---|---|---|
| Ubv.UIM1b.11 | 125 | MQILVTTIIVRTITLEVEPSDTIENVKAKI QDKEGIPPDQQRLIFSGKELEDGRTLSDYN IRNKSTLYLVGRLRGGGG |
| Ubv.UIM1b.12 | 126 | MQIFVNTLRAKFITLEVEPSDTIENVKAKI QDKEGIPPDQQRLLFAGQQLEDGRTLSDYN IHKESTLSLVASLRGDQK |
| Ubv.UIM1b.13 | 127 | MQIFVLTLKWKTIALEVEPSDTIENVKAKI QDKEGIPPDQQRLIFSGWHLEDGRTLSDYN IEKGSTLGLVLTLRGGGG |
| Ubv.UIM1b.14 | 128 | MEISVKTLAVKTITLEVEPSDTIENVKAKI QDKEGIPPDQQRLFFAGKLLEDGRTLSDYN IHRESTLLLVLRIYRRAS |
| Ubv.UIM1b.15 | 129 | MKIFVTTLTVKTIALEVEPSDTIENVKAKI QDKEGIPPDQQGLIFAGKQLEDGRTLSDYN IQKESTLLLGVMLRANRS |

TABLE 9

UBIQUITIN INHIBITORS WITH BINDING SPECIFICITY TO USP8

| UBIQUITIN VARIANT | SEQ ID NO | SEQUENCE |
|---|---|---|
| USP8-A01 | 130 | MQIFVKTPKGKNITLEVEPSDTIENVKAKI QDKEGIPPDQQRLIFIAKHLEDGRTLSDYN IPKESTLSLLMSFPRTVR |
| USP8-A03 | 131 | MQIFVKTLRGHLITLEVEPSDTIENVKAKI QDKEGIPPDQQRLIFVAKQLEDGRTLSDYN IHKESTLQLMFKPRGQRR |
| USP8-A04 | 132 | MQIFVKTLTGKTITLEVEPSDTIENVKAKI QDKEGIPPDQQSLSFAGKPLEDGRTLSDYN IHRTSTLHLVFSFRSRVK |
| USP8-A06 | 133 | MQIFVKTLTGKTITLEVEPSDTIENVKAKI QDKEGIPPDQQSLSFAGKPLEDGRTLSDYN IHRTSTLHLVFSFRSKVK |
| USP8-A07 | 134 | MQIFVKTLRGKTITLEVEPSDTIENVKAKI QDKEGIPPDQQRLFFDVKQLEDGRTLSDYN IQKESTLDLFLGLRGRSR |
| USP8-A08 | 135 | MQIFVKTLTGKTITLEVEPSDTIENVKAKI QDKEGIPPDQQRLIFSGKPLEDGRTLSDYN IPKESTLDLGLRRRTTVS |
| USP8-A09 | 136 | MQIFVKTLTGKTITLEVEPSDTIENVKAKI QDKEGIPPDQQRLIFAGKQLEDGRTLSDYN INWESTLRLWSRVRGKYQ |
| USP8-B03 | 137 | MQIFVKTVKGETIVLEVEPSDTIENVKAKI QDKEGIPPDQQKLYFDVKQLEDGRTLSDYN IQQESTLHLLVRLGGRGG |
| USP8-B06 | 138 | MQIFVITFPGKTIALEVEPSDTIENVKAKI QDKEGIPPDQQRLLFDVKQLEDGRTLSDYN IQNESTLNLVWRPRGVLN |
| USP8-B09 | 139 | MQIFVKTLTGKTITLEVEPSDTIENVKAKI QDKEGIPPDQQRLIFDVKQLEDGRTLSDYN IQTYSTLHLGLRLRGHTT |

TABLE 9-continued

UBIQUITIN INHIBITORS WITH BINDING SPECIFICITY TO USP8

| UBIQUITIN VARIANT | SEQ ID NO | SEQUENCE |
|---|---|---|
| USP8-B10 | 140 | MQIFVKTLMGRAITLEVEPSDTIENVKAKI QDKEGIPPDQQRLIFAGKQLEDGRTLSDYN IHKASTLYLMLRLRGGGG |

TABLE 10

UBIQUITIN INHIBITORS WITH BINDING SPECIFICITY TO USP21

| UBIQUITIN VARIANT | SEQ ID NO | SEQUENCE |
|---|---|---|
| USP21-E10 | 141 | MQIFVKTLTGKTITLEVEPSDTIENVKAKI QDKEGIPPDQQRLIFAGKQLEDGRTLSDYN IEWKSTLFLLLRLRSILL |
| USP21-E11 | 142 | MQIFVKTLTGKTITLEVEPSDTIENVKAKI QDKEGIPPDQQRLIFAGKQLEDGRTLSDYN IPKESTLFLLVRLFVKQI |
| USP21-E12 | 143 | MQIFVKTLTGKTITLEVEPSDTIENVKAKI QDKEGIPPDQQRLIFAGKQLEDGRTLSDYN IETGSTLFLLFRLRGMGT |
| USP21-E2 | 144 | MQIFVKTLTGKTITLEVEPSDTIENVKAKI QDKEGIPPDQQRLIFAGKQLEDGRTLSDYN IQKLSTLFLLLRFRSYMR |
| USP21-E3 | 145 | MQIFVKTLTGKTITLEVEPSDTIENVKAKI QDKEGIPPDQQRLIFAGKQLEDGRTLSDYN IYHKSTLFLLVKFRGLTP |
| USP21-E4 | 146 | MQIFVKTLTGKTITLEVEPSDTIENVKAKI QDKEGIPPDQQRLIFAGKQLEDGRTLSDYN IQNESTLFLLLRFPRVQA |
| USP21-E6 | 147 | MQIFVKTLTGKTITLEVEPSDTIENVKAKI QDKEGIPPDQQRLIFAGKQLEDGRTLSDYN IPKASTLFLLLRLHAQRR |
| USP21-E7 | 148 | MQIFVKTLTGKTITLEVEPSDTIENVKAKI QDKEGIPPDQQRLIFAGKQLEDGRTLSDYN IQKFSTLFLLLRLGGWYL |
| USP21-E9 | 149 | MQIFVKTLTGKTITLEVEPSDTIENVKAKI QDKEGIPPDQQRLIFAGKQLEDGRTLSDYN IQKQSTLFLVLRLRGKDM |
| USP21-F11 | 150 | MQIFVKTLTGKTITLEVEPSDTIENVKAKI QDKEGIPPDQQRLIFAGKQLEDGRTLSDYN IQRQSTLYLLIRIHRRKR |
| USP21-F12 | 151 | MQIFVKTLTGKTITLEVEPSDTIENVKAKI QDKEGIPPDQQRLIFAGKQLEDGRTLSDYN IQKHSTLYLLFRFTVKGR |
| USP21-F2 | 152 | MQIFVKTLTGKTITLEVEPSDTIENVKAKI QDKEGIPPDQQRLIFAGKQLEDGRTLSDYN IPRHSTLFLLFRLRDTSR |
| USP21-F3 | 153 | MQIFVKTLTGKTITLEVEPSDTIENVKAKI QDKEGIPPDQQRLIFAGKQLEDGRTLSDYN IHKASTLFLVLRVRAHKQ |
| USP21-F5 | 154 | MEIFVKTLSGMTITLEVEPSDTIENVKAKI QDKEGIPPDQQRLIFAGKQLEDGRTLSDYN IQKHSTLFLVLRLHVGNN |

TABLE 10-continued

UBIQUITIN INHIBITORS WITH BINDING SPECIFICITY TO USP21

| UBIQUITIN VARIANT | SEQ ID NO | SEQUENCE |
|---|---|---|
| USP21-F6 | 155 | MQIFVKTVTGKTITLEVEPSDTIENVKAKI QDKEGIPPDQQRLIFAGKQLEDGRTLSDYN IQKKSTLFLVLRLHSTRE |
| USP21-F9 | 156 | MQIFVKTLTGKTITLEVEPSDTIENVKAKI QDKEGIPPDQQRLIFAGKQLEDGRTLSDYN IHKESTLFLLLRFRGTLS |
| USP21-G11 | 157 | MQIFVKTVTGRSITLEVEPSDTIENVKAKI QDKEGIPPDQQRLIFAGKQLEDGRTLSDYN IQTKSTLFLVLRFRGNTR |
| USP21-G2 | 158 | MQIFVKTLTGKTITLEVEPSDTIENVKAKI QDKEGIPPDQQRLIFAGKQLEDGRTLSDYN IEKESTLFLLLRLPSWKG |
| USP21-G3 | 159 | MQIYVKTLPGKTITLEVEPSDTIENVKAKI QDKEGIPPDQQRLIFAGKQLEDGRTLSDYN IHLRSTLFLLFRPRRLYK |
| USP21-G4 | 160 | MQIFVKTLTGKTITLEVEPSDTIENVKAKI QDKEGIPPDQQRLIFAGKQLEDGRTLSDYN IEKKSTLFLLLRLYWEDK |
| USP21-G5 | 161 | MQIFVKTLTGKTITLEVEPSDTIENVKAKI QDKEGIPPDQQRLIFAGKQLEDGRTLSDYN IYNESTLFLLARLRFGRA |
| USP21-G6 | 162 | MQIFVKTSTGRTITLEVEPSDTIENVKAKI QDKEGIPPDQQRLIFAGKQLEDGRTLSDYN IQRQSTLFLIWRLTSAMV |
| USP21-G9 | 163 | MQIFVKTHTAKTILLEVEPSDTIENVKAKI QDKEGIPPDQQRLIFAGKQLEDGRTLSDYN INLESTLFLLFRFRGNTL |
| USP21-H1 | 164 | MQIFVKTPTGMSITLEVEPSDTIENVKAKI QDKEGIPPDQQRLIFAGKQLEDGRTLSDYN IQKVSTLFLVFKLWRRSM |
| USP21-H3 | 165 | MQIFVKTLTGKTITLEVEPSDTIENVKAKI QDKEGIPPDQQRLIFAGKQLEDGRTLSDYN IHKESTLFLLLRLSWDFK |
| USP21-H5 | 166 | MQIFVKTLTGKTITLEVEPSDTIENVKAKI QDKEGIPPDQQRLIFAGKQLEDGRTLSDYN IHKHSTLFLLLRLRSRLK |
| USP21-H6 | 167 | MQIFVKTLTGKTITLEVEPSDTIENVKAKI QDKEGIPPDQQRLIFAGKQLEDGRTLSDYN IVKNSTLFLLLRIHGSQK |
| USP21-H7 | 168 | MQIFVKTLTGKTITLEVEPSDTIENVKAKI QDKEGIPPDQQRLIFAGKQLEDGRTLSDYN IHKQSTLFLVLRLRGLSS |
| USP21-H8 | 169 | MQIFVKTLTGKTITLEVEPSDTIENVKAKI QDKEGIPPDQQRLIFAGKQLEDGRTLSDYN IQKDSTLFLLLRLRGLQY |

Methods

The present disclosure demonstrates that by enhancing the binding properties of ubiquitin (Ub) to existing natural ubiquitin binding sites of ubiquitin-specific-proteases (USP) the function of these enzymes was inhibited. To do so a combinatorial library of Ub variants was created by genetically engineering diversity in the interface region buried by the interaction of both proteins. As a proof of concept using this novel method, site specific inhibitors to USP8 and USP21 were created.

Accordingly, the present disclosure provides a method of producing enzyme-specific inhibitors comprising:

(a) identifying active site residues of a substrate in an enzyme-substrate complex;
(b) randomizing the active site residues to produce a combinatorial library of substrate variants; and
(c) selecting substrate variants that inhibit enzyme activity.

Identification of active site residues is performed by using various methods known in the art, including without limitation, analysis of 3D structures, alanine scanning, shotgun scanning and other mutational analysis of interaction interfaces.

In one embodiment, randomizing the active site residues in b) is by genetic engineering. For example, variants can be created where each active site residue is replaced with a different amino acid, such that a library of variants comprising all 20 amino acids in each active site position is produced. In one embodiment, randomization is performed to yield 75% wild type amino acid residues and 25% mutated amino acid residues at the active site residues. For ubiquitin, the active site residues comprise regions 1-3 as shown in FIGS. 1A-1B.

The combinatorial library can be screened for enzymatic inhibition, for example, by phage display, mRNA display, ribosome display, yeast display or other similar technologies to determine the inhibition of enzyme activity compared to a control. In one embodiment, the control is a different enzyme to test for enzyme specificity. In another embodiment, the control is the wild type enzyme to test for amount of inhibition.

Enzyme activity can be inhibited in a variety of ways. In one embodiment, the substrate variant has a higher affinity to the active site of the enzyme, which provides competitive inhibition. In another embodiment, the substrate variant blocks the active site of the enzyme after an enzymatic reaction, which provides product inhibition. In yet another embodiment, the substrate variant induces a change in the shape of the enzymatic active site, which provides allosteric inhibition.

The enzyme can be any enzyme, for example, a transferase, hydrolase, lyase, or ligase.

In one embodiment, the substrate is ubiquitin and the enzyme is a Ub-activating enzyme (E1 enzyme), a Ub-conjugating enzymes (E2 enzyme) or a Ub ligase (E3 enzyme). In one embodiment, the Ub ligase is a HECT ubiquitin Ligase, such as NEDD4 or ITCH. In another embodiment, the substrate is ubiquitin and the enzyme is a deubiquitinating enzyme. In one embodiment, the deubiquitinating enzyme is a ubiquitin specific protease (USP), a ubiquitin C-terminal hydrolase (UCH), an ovarian tumor protease (OTU), a Machado-Joseph disease protease (MJD) or a JAB1/MPN/MOV34 metalloenzyme (JAMM). In one embodiment, the deubiquitinating enzyme is a ubiquitin specific protease (USP). In an embodiment, the USP is USP2, USP4, USP5, USP7, USP8, USP9x, USP9y, USP10, USP12, USP14, USP16, USP21, USP28, USP42, USP46 or USP48. In one embodiment, the USP is USP2, USP5, USP8, USP10, USP21, or USP48. In a further embodiment, the USP includes all splice forms, i.e. isoforms, of USP2, USP4, USP5, USP7, USP8, USP9x, USP9y, USP10, USP12, USP14, USP16, USP21, USP28, USP42, USP46 or USP48.

In another embodiment, the substrate is ubiquitin as shown in SEQ ID NO: 1 and the resulting variant comprises mutations in the active site residues present in region 1 (amino acids 2-14) and region 3 (amino acids 62-72). In yet another embodiment, the substrate is ubiquitin as shown in SEQ ID NO: 1 and the resulting variant comprises mutations in the active site residues present in region 3 (amino acids 62-72). In yet another embodiment, the substrate is ubiquitin and the resulting variant comprises mutations in at least one of positions 2, 4, 6, 8, 9, 10, 11, 12, 14, 35, 37, 39, 40, 42, 44, 46, 47, 48, 49, 62, 63, 64, 66, 68, 70, 71 or 72, optionally in at least one of positions 2, 4, 6, 8, 9, 10, 11, 12, 14, 62, 63, 64, 66, 68, 70, 71 or 72 or in at least one of positions 62, 63, 64, 66, 68, 70, 71 or 72. In another embodiment, the resulting variant comprises mutations in at least 2, 4, 6 or 8 of the positions.

In another embodiment, the substrate is a ubiquitin variant as shown in SEQ ID NO: 21 and the resulting inhibitors comprises an amino acid mutation in region 1 (amino acids 2-14), region 2 (amino acids 42-49), or region 3 (amino acids 62-78) in the amino acid sequence of a ubiquitin variant (Ubv) as set forth in SEQ ID NO: 21. In yet another embodiment, the substrate is ubiquitin and the resulting inhibitors comprises an amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 of the amino acid sequence of a ubiquitin variant (Ubv) set forth in SEQ ID NO: 21.

Enzyme Inhibitors

The methods described herein are applied, by way of example, on the protein substrate ubiquitin and enzymes in the ubiquitination and deubiquitination pathway.

Within the ubiquitination-pathway multiple enzymes rely on the efficient recognition of ubiquitin and ubiquitin chains as their primary substrate. By modifying ubiquitin as protein substrate in the above-described manner, enzymes in the ubiquitin-pathway can be inhibited. Target molecules in the ubiquitination pathway for an Ub-based inhibitor are Ub-activating enzymes (E1 enzymes), Ub-conjugating enzymes (E2 enzymes) and Ub ligases (E3 enzymes). These enzymes are responsible for attaching ubiquitin to other proteins and by that influence the homeostasis of proteins, their localization within the cell and regulate cellular signalling. The human genome encodes for 2 Ub-activating E1 enzymes while at least 38 conjugating E2-enzymes are known to date [Ye and Rape 2009]. Additionally, more than 600 E3 enzymes have been identified so far and can be divided into 2 major families: HECT domain—E3 ligases and RING-domain E3-ligases. More than 90% of the E3 ligases belong to the RING domain ligase family which main functions are to interact with Ub conjugated E2's and the corresponding substrate. RING domain E3 ligases facilitate the transfer of Ub directly from the E2 enzyme to the substrate. The chain topology found in poly-ubiquitinated proteins often depend on the involved E2 enzyme. Therefore, Ub based inhibitors of E2-conjugating enzymes can be used to interfere and control multiple targets at once due to their involvement in many different aspects of ubiquitination. In contrast to RING domain E3 ligases, HECT domain E3 ligases covalently interact through a thio-ester bond with Ub and transfer Ub to the substrate without the involvement of E2-conjugating enzymes. Therefore, targeting HECT-domain E3-ligases with Ub-based inhibitors would allow a more direct and limited interference with ubiquitylated substrates. In summary, multiple levels of intracellular control are conceivable by targeting the ubiquitination machinery either through inhibiting E2 or E3 enzymes. Another group of target molecules are deubiquitinating enzymes such as Ubiquitin specific proteases (USPs), Ubiquitin C-terminal hydrolases (UCHs), ovarian tumor proteases (OTUs), Machado-Joseph disease proteases (MJDs) and JAB1/MPN/MOV34 metalloenzymes (JAMMs) [Ventii and Wilkinson 2008; Komander, Clague et al. 2009; Reyes-Turcu, Ventii et al. 2009]. Deubiquitinating enzymes provide a large binding surface for the recognition and subsequent proteolysis of mono-ubiqutinated and poly-ubiquitinated proteins. In poly-ubiquitinated proteins Ub can appear in different conformations such as K6, K11, K27, K29, K33, K48, K63 linked Ub-chains as well as linear Ub-chains.

Accordingly, the present disclosure provides a ubiquitin enzyme inhibitor comprising mutations in region 3 (amino acids 62-72) of the amino acid sequence of ubiquitin as shown in SEQ ID NO: 1 and optionally, further comprising mutations in region 1 (amino acids 2-14) of the amino acid sequence of ubiquitin as shown in SEQ ID NO: 1.

In another embodiment, the ubiquitin enzyme inhibitor comprises mutations in at least one of positions 2, 4, 6, 8, 9, 10, 11, 12, 14, 35, 37, 39, 40, 42, 44, 46, 47, 48, 49, 62, 63, 64, 66, 68, 70, 71 or 72 of the amino acid sequence of ubiquitin as shown in SEQ ID NO:1, optionally in at least one of positions 2, 4, 6, 8, 9, 10, 11, 12, 14, 62, 63, 64, 66, 68, 70, 71 or 72 of the amino acid sequence of ubiquitin as shown in SEQ ID NO:1 or in at least one of positions 62, 63, 64, 66, 68, 70, 71 or 72 of the amino acid sequence of ubiquitin as shown in SEQ ID NO:1. In another embodiment, the ubiquitin enzyme inhibitor comprises mutations in at least 2, 4, 6 or 8 of the positions.

The present disclosure also provides a ubiquitin enzyme inhibitor comprising an amino acid mutation in region 1 (amino acids 2-14), region 2 (amino acids 42-49), or region 3 (amino acids 62-78) of the amino acid sequence of a ubiquitin variant (Ubv) set forth in SEQ ID NO: 21.

In one embodiment, a ubiquitin enzyme inhibitor of the disclosure comprises an amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 in the amino acid sequence of the ubiquitin wildtype variant (Ubv) polypeptide set forth in SEQ ID NO: 21.

In one embodiment, the enzyme is a Ub-activating enzyme (E1 enzyme), a Ub-conjugating enzymes (E2 enzyme) or a Ub ligase (E3 enzyme). In one aspect, the E3 ligase is Nedd4 or ITCH. In another embodiment, the enzyme is a deubiquitinating enzyme. In one embodiment, the deubiquitinating enzyme is a ubiquitin specific protease (USP), a ubiquitin C-terminal hydrolase (UCH), an ovarian tumor protease (OTU), a Machado-Joseph disease protease (MJD) or a JAB1/MPN/MOV34 metalloenzyme (JAMM).

In an embodiment, the deubiquitinating enzyme is a USP. In one embodiment, the USP inhibitor comprises a mutation at position 68 optionally Tyr or Phe for His of the amino acid sequence of ubiquitin as shown in SEQ ID NO: 1. In another embodiment, the USP inhibitor comprises a Val to Leu mutation at position 70 of the amino acid sequence of ubiquitin as shown in SEQ ID NO: 1.

In another embodiment, the USP is USP8 or USP21. In one embodiment, the USP8 inhibitor comprises the sequence shown in SEQ ID NO: 2 (Ub variant 8.2) or SEQ ID NO: 3 (Ub variant 8.3). In another embodiment, the USP21 inhibitor comprises the sequence shown in SEQ ID NO:4 (Ub variant 21.1), SEQ ID NO:5 (Ub variant 21.2), SEQ ID NO:6 (Ub variant 21.3), SEQ ID NO:7 (Ub variant 21.4) or SEQ ID NO:8 (Ub variant 21.5).

In additional embodiments, the USP is USP2, USP5, USP8, USP10, USP21, or USP48. In one embodiment, the USP inhibitor inhibits USP2 and comprises any of the amino acid sequences of SEQ ID NOS: 22-47. In another embodiment, the USP inhibitor inhibits USP5 and comprises any of the amino acid sequences of SEQ ID NOS: 48-68. In another embodiment, the USP inhibitor inhibits USP10 and comprises the amino acid sequence of SEQ ID NO: 69. In another embodiment, the USP inhibitor inhibits USP48 and comprises any of the amino acid sequences of SEQ ID NOS: 70-74. In another embodiment, the USP inhibitor inhibits USP8 and comprises any of the amino acid sequences of SEQ ID NOS: 130-140. In another embodiment, the USP inhibitor inhibits USP21 and comprises any of the amino acid sequences of SEQ ID NOS: 141-169.

In another embodiment, the E3 ubiquitin ligase is Nedd4 or ITCH. In one embodiment, the Nedd4 binder comprises any of the amino acid sequences of SEQ ID NOS: 75-98. In another embodiment, the ITCH binder comprises any of the amino acid sequences of SEQ ID NOS: 99-104.

In another embodiment, the UIM binder comprises any of the amino acid sequences of SEQ ID NOS: 105-129.

The enzyme inhibitors disclosed herein also include conservative substitutions, as well as deletions and or additions that work in substantially the same way as an inhibitor of ubiquitin. In one embodiment, the enzyme inhibitor is a fragment of an amino acid sequence disclosed herein that performs substantially the same function in substantially the same way.

The enzyme inhibitors disclosed herein also include analogs and derivatives thereof.

The enzyme inhibitors may also contain or be used to obtain or design "peptide mimetics." Peptide mimetics include synthetic structures that may serve as substitutes for peptides in interactions between molecules (see Morgan and Gainor. (1989), Ann. Reports Med. Chem. 24:243-252 for a review). Peptide mimetics include synthetic structures which may or may not contain amino acids and/or peptide bonds but are designed to retain the desired structural and functional features and thus may be suitable substitutes of the peptide inhibitor analog disclosed herein.

Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad. Sci. USA 89:9367), and peptide libraries containing peptides of a designed length representing all possible sequences of amino acids corresponding to an isolated peptide of the disclosure. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The disclosure further provides nucleic acids encoding the ubiquitin enzyme inhibitors disclosed herein.

Accordingly, the present disclosure provides a nucleic acid molecule encoding a ubiquitin enzyme inhibitor comprising mutations in region 3 (amino acids 62-72) of the amino acid sequence of ubiquitin as shown in SEQ ID NO: 1 and optionally, further comprising mutations in region 1 (amino acids 2-14) of the amino acid sequence of ubiquitin as shown in SEQ ID NO: 1. The present disclosure also provides a nucleic acid encoding a ubiquitin enzyme inhibitor comprising an amino acid mutation in at least one of region 1 (amino acids 2-14), region 2 (amino acids 42-49), or region 3 (amino acids 62-78) in the amino acid sequence of a ubiquitin variant (Ubv) set forth in SEQ ID NO:21.

In another embodiment, there is provided a nucleic acid molecule encoding a ubiquitin enzyme inhibitor comprising mutations in at least one of positions 2, 4, 6, 8, 9, 10, 11, 12, 14, 35, 37, 39, 40, 42, 44, 46, 47, 48, 49, 62, 63, 64, 66, 68, 70, 71 or 72 of the amino acid sequence of ubiquitin as shown in SEQ ID NO:1, optionally in at least one of positions 2, 4, 6, 8, 9, 10, 11, 12, 14, 62, 63, 64, 66, 68, 70, 71 or 72 of the amino acid sequence of ubiquitin as shown in SEQ ID NO:1 or in at least one of positions 62, 63, 64, 66, 68, 70, 71 or 72 of the amino acid sequence of ubiquitin as shown in SEQ ID NO:1. In another embodiment, the ubiquitin enzyme inhibitor comprises mutations in at least 2, 4, 6 or 8 of the positions.

In one embodiment, the disclosure provides a nucleic acid molecule encoding a USP inhibitor comprising a mutation at position 68, optionally Tyr or Phe for His, of the amino acid sequence of ubiquitin as shown in SEQ ID NO: 1. In another embodiment, the disclosure provides a nucleic acid molecule encoding a USP inhibitor comprising a Val to Leu mutation at position 70 of the amino acid sequence of ubiquitin as shown in SEQ ID NO: 1.

In a further embodiment, the disclosure provides a nucleic acid molecule comprising the nucleic acid sequence as shown in SEQ ID NO: 13 or encoding a USP8 inhibitor comprising the sequence as shown in SEQ ID NO: 2 (Ub variant 8.2) or a nucleic acid molecule comprising the nucleic acid sequence as shown in SEQ ID NO: 14 or encoding a USP8 inhibitor comprising the sequence as shown in SEQ ID NO: 3 (Ub variant 8.3). In another embodiment, there is provided a nucleic acid molecule comprising a nucleic acid sequence as shown in SEQ ID NO:15 or encoding a USP21 inhibitor comprising the sequence shown in SEQ ID NO:4 (Ub variant 21.1), a nucleic acid molecule comprising a nucleic acid sequence as shown in SEQ ID NO:16 or encoding a USP21 inhibitor comprising the sequence as shown in SEQ ID NO:5 (Ub variant 21.2), a nucleic acid molecule comprising a nucleic acid sequence as shown in SEQ ID NO:17 or encoding a USP21 inhibitor comprising the sequence as shown in SEQ ID NO:6 (Ub variant 21.3), a nucleic acid molecule comprising a nucleic acid sequence as shown in SEQ ID NO:18 or encoding a USP21 inhibitor comprising the sequence as shown in SEQ ID NO:7 (Ub variant 21.4) or a nucleic acid molecule comprising a nucleic acid sequence as shown in SEQ ID NO:19 or encoding a USP21 inhibitor comprising the sequence as shown in SEQ ID NO:8 (Ub variant 21.5).

In another embodiment, the disclosure provides a nucleic acid encoding a polypeptide comprising at least one amino acid mutation at position 2, 4, 6, 8, 9, 10, 11, 12, 14, 42, 44, 46, 47, 48, 49, 62, 63, 64, 68, 70, 71, 72, 73, 74, 75, 76, 77, or 78 of the amino acid sequence of a ubiquitin variant (Ubv) set forth in SEQ ID NO:21.

In addition, the present disclosure provides a nucleic acid which encodes any of the polypeptides of SEQ ID NOS: 2-8 and 22-173.

In another embodiment, the disclosure provides a nucleic acid encoding any of the ubiquitin variants identified by the methods described herein. A person skilled in the art will appreciate that the enzyme inhibitors, or more particularly, ubiquitin variants, of the disclosure may be prepared in any of several ways, optionally, by recombinant methods.

Accordingly, nucleic acid molecules encoding the enzyme inhibitors, or more particularly, ubiquitin variants, may be incorporated in a known manner into an appropriate expression vector which ensures good expression of the proteins. Possible expression vectors include, but are not limited to, cosmids, plasmids, or modified viruses (e.g. replication defective retroviruses, adenoviruses and adeno-associated viruses), so long as the vector is compatible with the host cell used. The expression vectors may contain a nucleic acid molecule of the disclosure and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The disclosure therefore contemplates a recombinant expression vector comprising a nucleic acid molecule encoding an enzyme inhibitor, or more particularly, ubiquitin variant, as disclosed herein, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a selectable marker gene which facilitates the selection of host cells transformed or transfected with a recombinant molecule of the disclosure. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMaI (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell.

Suitable host cells include a wide variety of eukaryotic host cells and prokaryotic cells. For example, the enzyme inhibitors, or ubiquitin variants, may be expressed in yeast cells or mammalian cells. Other suitable host cells can be found in Goeddel, Gene Expression Technology: Methods in Enzymology 185, Academic Press, San Diego, Calif. (1991). In addition, the enzyme inhibitors, or ubiquitin variants, may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Accordingly, the disclosure provides a host cell comprising the nucleic acid sequences or recombinant expression vectors disclosed herein.

The nucleic acid molecules disclosed herein may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The enzyme inhibitors, or more particularly, ubiquitin variants, may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

The disclosure also provides the various ubiquitin variants for use in screening small molecule libraries for inhibitors of the ubiquitin pathway, including inhibitors of USPs, OTUs, E3 ligases and E2-conjugating enzymes.

The disclosure also provides the various ubiquitin variants described herein for use in the treatment of a range of diseases, including cancer. As used herein, the term "cancer" refers to any type of cancer, including, but not limited to, ovarian cancer, leukemia, lung cancer, colon cancer, CNS cancer, melanoma, renal cancer, prostate cancer, pancreatic cancer, breast cancer, and the like.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1—Design, Synthesis and Testing of Ubiquitin 8 and 21 Variants

Results

Human Ub was displayed in a monovalent format on the surface of M13 bacteriophage as a fusion to the C-terminal domain of the p3 minor coat protein, using a phagemid system used previously for the display of antibodies and other proteins [Sidhu, Lowman et al. 2000; Sidhu, Li et al. 2004; Li, Xi et al. 2009]. By inspection of structures of Ub in complex with several USPs, 27 Ub residues were identified that make contact with the USP surface, and this residue set was defined as the USP-binding site. These 27 residues could be conveniently divided into three groups, with each group containing residues that are close together in the primary sequence, as follows: region 1 (residues Q2, F4, K6, L8, T9, G10, T11, T12 and T14), region 2 (residues G35, P37, D39, Q40, R42, I44, A46, G47, K48 and Q49) and region 3 (residues Q62, K63, E64, T66, H68, V70, L71 and R72) (FIGS. 1A-1B). To construct a library that simultaneously targets all 27 residues for randomization, a methodology that has been applied previously for the construction of high quality antibody libraries was used in which more than 30 residues in four distinct regions of primary sequence were successfully randomized [Fellouse and Sidhu 2007]. Three mutagenic oligonucleotides (each corresponding to one of the three regions) were synthesized and incorporated into the Ub-encoding gene in the phage display vector. A "soft" randomization strategy was utilized in which the mutagenic oligonucleotides were designed to encode approximately 75% of the wild-type (wt) amino acid and 25% of a mixture of the other amino acids at each targeted position [Fellouse and Sidhu 2007]. In addition, the strategy allowed for the recovery of the full wt sequence in each region, in the event that the mutagenic oligonucleotide was not incorporated (~30% of the population). In this way, the library was biased in favour of the wt sequence but allowed for significant diversity across the entire USP-binding surface, and it was reasoned that this would enable the selection of variants with mutations that improve affinity for a particular USP without drastically altering the binding site.

Figure 2B:
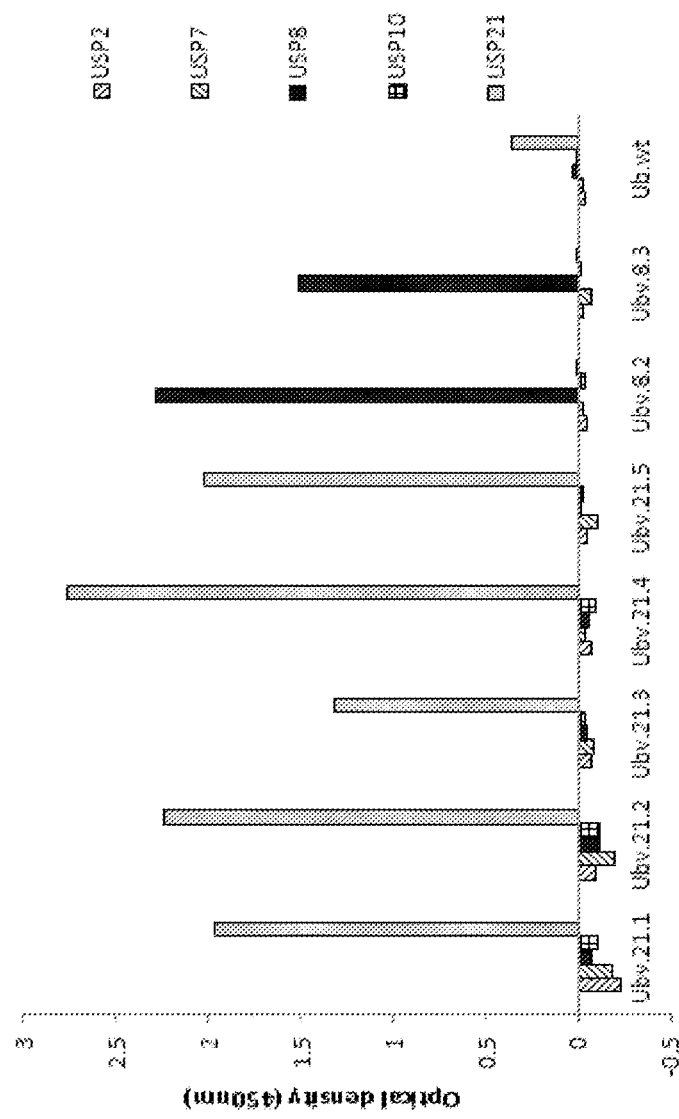

A phage pool representing the Ub library was cycled through five rounds of selection for binding to immobilized USP8 or USP21. After the fifth round, 24 clones from each selection were tested for binding activity by phage enzyme-linked immunosorbent assay (ELISA) [Tonikian, Zhang et al. 2007]. Clones that bound to the relevant USP, but not to a negative control protein, were subjected to DNA sequencing, and this analysis revealed two or five unique Ub variants that bound to USP8 or USP21, respectively (FIG. 2A). The binding profiles of these variants, and that of wt Ub (Ub.wt (SEQ ID NO: 1)), were analyzed in further detail by phage ELISA against a panel of five USPs (USP8, USP21, USP2, USP7 and USP10). As expected, each of the seven Ub variants recognized its cognate USP, and importantly, none of the clones exhibited detectable binding to any of the four non-cognate USPs (FIG. 2B). Ub.wt (SEQ ID NO: 1) bound weakly to USP21 but did not exhibit detectable binding to the other four USPs, consistent with low affinity binding that is below the detection limit of the monovalent phage display format.

Sequence analysis revealed both common and unique features amongst the clones selected for binding to the two USPs. In all cases, region 2 was completely conserved as the wt, suggesting that mutations in this region do not generally enhance affinity. Four of the five USP21-binding clones contained mutations only in region 3, and one clone contained mutations in regions 1 and 3. The two USP8-binding clones contain mutations in both regions 1 and 3. Interestingly, all seven clones share a common Val to Leu mutation at position 70 and they all contain a mutation at position 68, although the nature of the mutation differs slightly amongst clones selected against the different targets (Tyr or Phe substitute for His in clones that bind to USP8 or USP21, respectively). Aside from these common features, the binders for USP8 and USP21 differ in sequence at other positions, and these differences likely confer specificity. The Ub variants were cloned into a bacterial expression vector and were purified from the soluble cytoplasmic fraction as His-tag fusions. All variants were purified in good yield (~10 mg per litre of culture) and were stable for months at 4° C. To test whether the Ub variants act as inhibitors of USP proteolytic activity, in vitro assays were used with the substrate Ub-AMC, which is prepared by C-terminal derivatisation of Ub with 7-amino-4-methylcoumarin (AMC). Active USPs cleave the Ub-AMC substrate and release fluorescent AMC. This is a well-established assay for probing USP activity and is also used to determine the affinity of Ub for USPs [Case and Stein 2006; Renatus, Parrado et al. 2006].

Figure 3A:
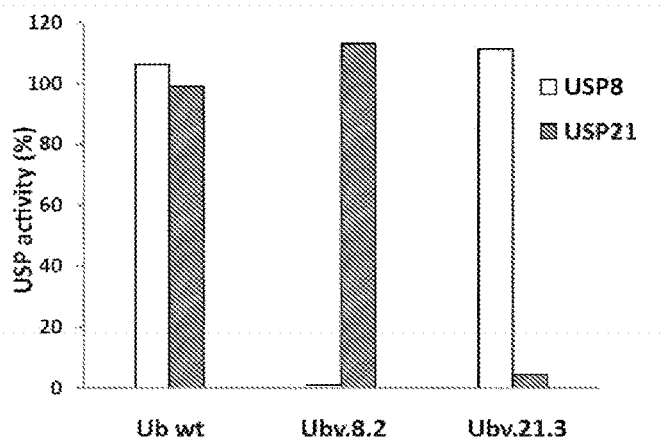
FIGS. 3A-3B shows phage-derived Ub variants are potent and specific inhibitors of USPs.
Figure 3B:
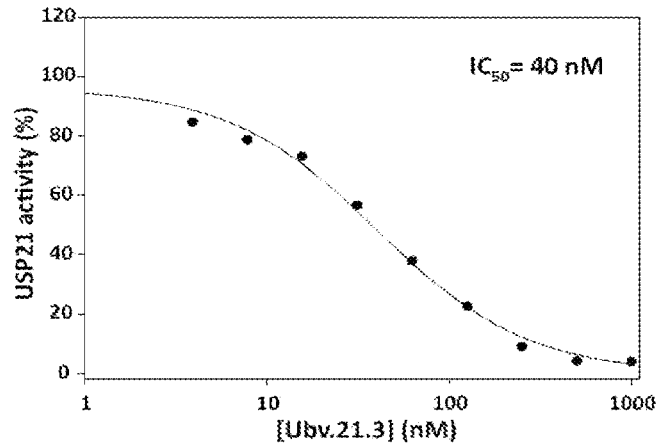
Figure 3C:
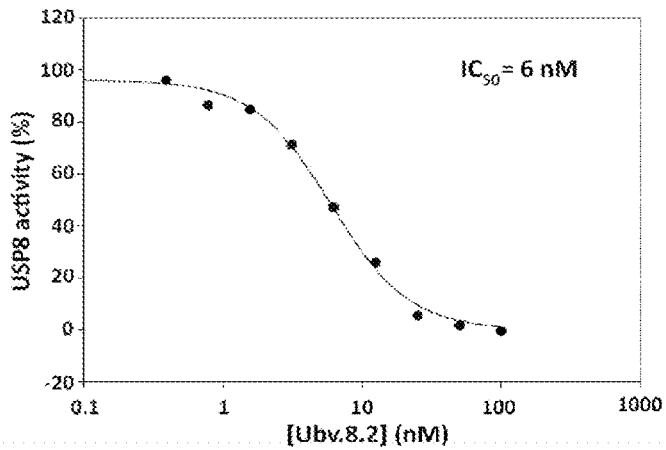

These assays showed that the activity of USP8 was inhibited by Ubv.8.2 (SEQ ID NO: 2) but not by either Ub.wt (SEQ ID NO: 1) or Ubv.21.3 (SEQ ID NO: 6). Conversely, the activity of USP21 was inhibited by Ubv.21.3 (SEQ ID NO: 6) but not by either Ub.wt (SEQ ID NO: 1) or Ubv.8.2 (SEQ ID NO: 2) (FIG. 3A). Full dose-response curves revealed that Ubv.8.2 (SEQ ID NO: 2) is an extremely potent inhibitor of USP8 activity ($IC_{50}$=6 nM) and Ubv.21.3 (SEQ ID NO: 6) is a potent inhibitor of USP21 activity ($IC_{50}$=40 nM) (FIG. 3B).

Figure 4A:
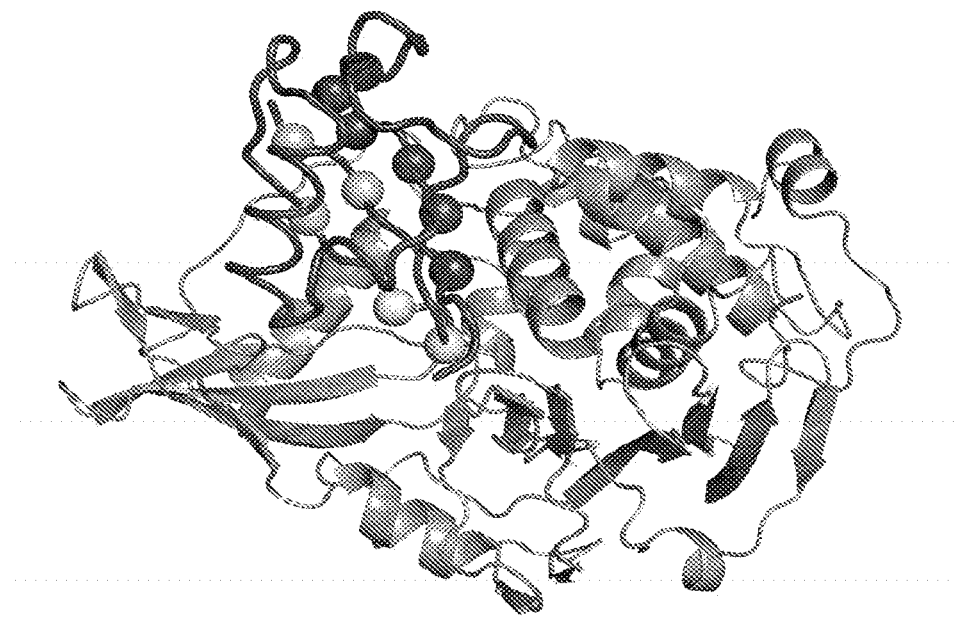
FIGS. 4A-4B shows USPs in complex with corresponding inhibitors. Ub-variants are shown in dark gray tubes. Changes contributing to an enhanced affinity from region 1 are shown as light gray spheres and from region 3 as dark gray spheres.
Figure 4B:
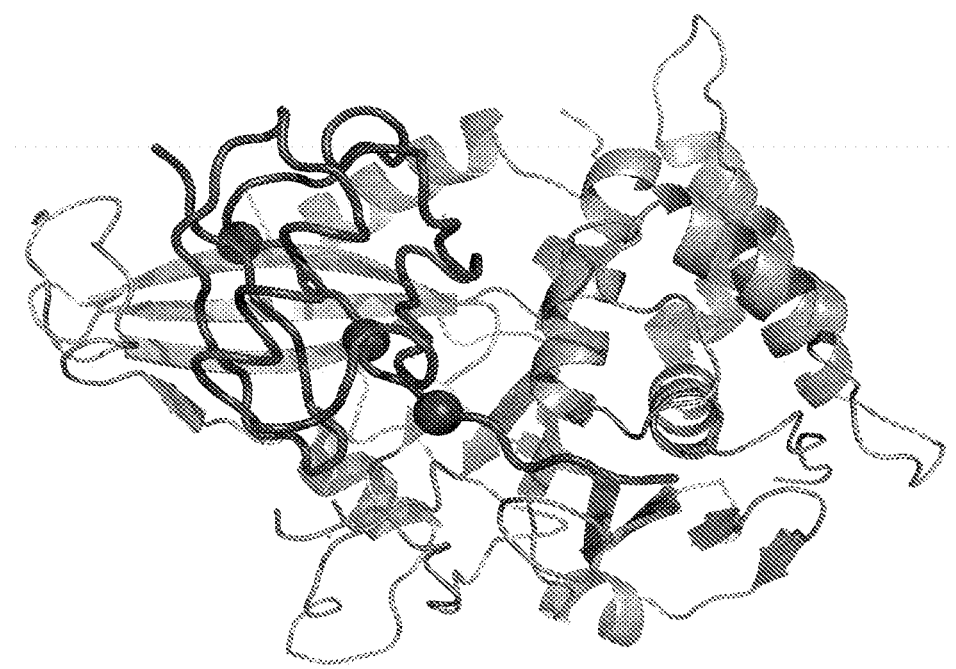

The structures of USP21 and USP8 were determined in complex with the corresponding inhibitor to confirm the details of the inhibition (FIGS. 4A-4B). Overall, the USP and the Ub fold were found to be preserved and to be similar to other USP Ub complex structures. For USP21, the resulting structure was compared with the USP21-Ub complex structure (pdb entry: 3I3T). Interestingly, the C-terminus of the Ub-variant in the USP21-Ubv.21.4 (SEQ ID NO: 7) crystal structure appears to be cleaved although the Ubv.21.4 (SEQ ID NO: 7) was purified with additional C-terminal residues (FIG. 4A). This shows that the protein is captured in an active conformation. Additionally, to stabilize the crystallized complex of USP21-Ub, the Ub is covalently attached to the active site cysteine of USP21. In the USP21-Ubv.21.4 (SEQ ID NO: 7) structure, this is not necessary since the variant binds with a high affinity to the binding site to form a stable complex at room temperature. In general, it was observed that former repulsive interactions necessary for correct product release have been replaced with attractive interactions. For example, the mutation E64W in the ligand replaces the repulsive interaction with D438 on USP21. At the same time, the mutation H68F replaces a water-mediated hydrogen bond with a hydrophobic interaction. Unexpectedly, this mutation is conserved amongst the selected binders however does not necessarily produce the same environment since it plays a different role in the USP8:Ubv.8.2 (SEQ ID NO: 2) structure. Finally, the more conservative mutation V70L improves hydrophobic contacts between the inhibitory Ubv.21.4 (SEQ ID NO: 7) and USP21 compared to Ub.wt (SEQ ID NO: 1).

In the USP8:Ubv.8.2 (SEQ ID NO: 2) structure the C-terminus does not align with the active site of the protein (FIG. 4B). Although not visible in the crystal structure, the extended C-terminus is still present as shown by mass-spec of the crystallized sample. In contrast to Ubv.21.4 (SEQ ID NO: 7), Ubv.8.2 (SEQ ID NO: 2) contains 12 mutations across region 1 and region 3 of the interaction interface of Ub. The catalytically non-active binding mode is explained by a slight twist of the interactions of the C-terminal β-strand, where instead of interacting with the lower parts of the zinc-finger region it interacts with the α-helix of the palm-domain of the USP flanking the binding pocket. This rotation is mainly caused by two hydrogen bonds formed between mutations in region 1 (Ubv.8.2 (SEQ ID NO: 2):Q2R and USP8:E895 and Ubv.8.2 (SEQ ID NO: 2):K11R and USP8:E947 respectively) and is further stabilized by an additional hydrogen bond formed between Ubv.8.2 (SEQ ID NO: 2):H68Y and USP8:D878.

Materials and Methods

Construction of the Ub-library

The Ub library was constructed based on the phagemid pLB0131.F. This plasmid encodes under the control of an IPTG inducible lac-promoter for an N-terminal fusion protein of the DsbA signal sequence, the Flag-tag (DYKDDDK (SEQ ID NO:9), Ub and a truncated version of the minor coat protein p3 of filamentous phage M13. Single stranded DNA template of this plasmid was prepared using previously described methods [Tonikian, Zhang et al. 2007]. The oligonucleotides targeting region 1 (pdl1), region 2 (pdl2) and region 3 (pdl3) were designed as follows: pdl1 (SEQ ID NO:10): GAC GAT GAC AAA ATG (N2)(N1)(N3) ATT (N4)(N4)(N2) GTG (N1)(N1)(N1) ACC (N2)(N4)(N4) (N1) (N2)(N3) (N3)(N3)(N3) (N1)(N1)(N3) (N1)(N2)(N2) ATC (N1)(N2)(N2) CTC GAG GTT GAA CCC, pdl2 (SEQ ID NO:11): ATC CAG GAT AAG GAA (N3)(N3)(N1) ATT (N2)(N2)(N4) CCT (N3)(N1)(N4) (N2)(N1)(N3) CAG (N1) (N3)(N1) CTG (N1)(N4)(N2) TTT (N3)(N2)(N4) (N3)(N3) (N2) (N1)(N1)(N3) (N2)(N1)(N3) CTG GAA GAT GGA CGT, pdl3 (SEQ ID NO:12): TCT GAC TAC AAT ATT (N2)(N1)(N1) (N1)(N1)(N3) (N3)(N1)(N3) TCT (N1)(N2) (N4) CTT (N2)(N1)(N4) CTT (N3)(N4)(N3) (N4)(N4)(N3) (N1)(N3)(N1) CTT CGT GGT GGT GGC. For each oligonucleotide the place holder N1 describes a mixture of nucleotides A 73% C 9% G 9% and T 9%; N2 describes a mixture of A 9%, C 73%, G 9% and T 9%; N3 describes a mixture of A 9% C 9%, G 73% and T 9%; N4 describes a mixture of A 9%, C 9%, G 9% and T 73%. Different mutational loads are conceivable dependent on the purpose of the application. All three oligonucleotides were used simultaneously in the mutagenesis using previously established methods [Tonikian, Zhang et al. 2007]. In total a library diversity of $7.5 \cdot 10^{10}$ unique Ub-variants was achieved. Phage pools representing the naïve peptide library were produced from E. coli SS320 cultures grown overnight at 37° C. in superbroth media supplemented with 25 µg/ml kanamycin, 100 µg/ml carbenicilin, 0.4 mM IPTG. Phage were harvested by precipitation with 20% PEG-8000/2.5M NaCl and resuspended at a final concentration of $10^{13}$ phage/mL in assay buffer (PBS, 0.5% BSA and 0.5% Tween 20).

Selection of Inhibitors

The resulting library was independently selected against the catalytic domains of USP21 (Uniprot accession number Q9UK80: residues 209-564) and USP8 (Uniprot accession number P40818: residues 764 to 1118). Both USPs were biotinylated using commercially available N-hydroxysuccinimidyl d-biotin-15-amido-4,7,10,13-tetraoxapentadecylate (NHS-PEO$_4$-Biotin) following the manufacturer's instructions (Thermo Fisher Scientific, Rockford, Il 61105 USA). 100 µl Neutravidin (50 µg/ml in PBS) (Thermo Fisher Scientific, Rockford, Il 61105, USA) was coated overnight at 4° C. on a Maxisorp micro titer plate (Nalge Nunc International, Rochester, N.Y., USA) (100 µL per well). The wells were blocked for 2 hours with blocking buffer (PBS, 0.2% BSA, 0.5% Tween 20). The biotinylated target proteins USP8 and USP21 were diluted into PBS to a final concentration of 50 µg/ml and 100 µL were added to the micro titer plate. 100 µL of ubiquitin-displaying phage were added to each well and incubated for 2 h at 4° C. Non-binding phage were removed by washing the micro-titer plate 8 times. Bound phage were eluted for 15 min with 100 µL 0.1 N HCl and immediately neutralized by addition of 1 M Tris. E. coli Xl1 blue was grown to an OD$_{600}$ of 0.6 and an aliquot of this culture was infected with the eluted phage in a ratio of 1:10. After incubation for 30 min at 37° C. while shaking at 200 rotations per minute (rpm) helper phage M13KO7 was added to a multiplicity of infection (MOI) of 10 and incubated for 1 h at 37° C. while shaking at 200 rpm. This culture was transferred to 30 ml of freshly prepared 2YT containing 25 µg/ml kanamycin, 100 µg/ml carbenicilin, 0.4 mM IPTG and incubated over night at 37° C. while shaking at 200 rpm. From this culture of XL1 blue the phage for the second round of selection were prepared by precipitation with 20% PEG-8000/2.5 M NaCl. Phage were resuspended in 1 ml of assay buffer and used in a 2 second round of selection. All rounds on wards were done at room temperature and washing steps after phage incubation were increased from 10 in the $2^{nd}$ round to 16 in the $5^{th}$ round of selection. After the $5^{th}$ round, individual ub variants were identified by single clone ELISA using established techniques [Pearce, Potts et al. 1997]. By sequencing of the encoding DNA 5 Ub-variants with binding activity to USP21 and 2 Ub-variants with binding activity to USP8 were identified (FIG. 2A).

Specificity Test

The specificity of the selected binders was tested against a set of unrelated USPs in phage ELISA format (Pearce, 1997#533). As test set the biotinylated catalytic domains of USP2 (Uniprot entry Q75604: residues 262-605), USP7 (Uniprot entry Q93009: residues 207-533) and USP10 (Uniprot entry Q14694: residues 385-798) were used. USP8 and USP21 were included as positive control for the corresponding Ub-variants. From individual colonies encoding the variants Ubv.21.1 (SEQ ID NO: 4), Ubv.21.2 (SEQ ID NO: 5), Ubv.21.3 (SEQ ID NO: 6), Ubv.21.4 (SEQ ID NO: 7), Ubv.21.5 (SEQ ID NO: 8), Ubv.8.1, Ubv.8.2 (SEQ ID NO: 2) and Ub.wt (SEQ ID NO: 1) 450 µl of 2YT containing 25 µg/ml kanamycin, 100 µg/ml carbenicilin, 0.4 mM IPTG and $10^{10}$ cfu/ml helper phage M13KO7 were inoculated and incubated over night at 37° C. while shaking at 200 rpm. Cultures were centrifuged at 10000 g for 10 min at 4° C. and the supernatant was diluted 1:10 in PBS and directly added to the immobilized USP. The USPs were immobilized on a micro-titer plate as described above. After incubation of the diluted phage containing culture supernatant for 1 h, the ELISA plate was washed 3 times with PBST 0.1 and 100 µl 1:5000 dilution of commercially available anti-M13 antibody horseradish peroxidase (Amersham-Pharmacia, Piscataway, N.J.) was added and incubated for 1 h. After a second wash, the ELISA was developed with 100 µl TMB peroxidase substrate (KPL, Gaithersburg, Md., USA). The reaction was stopped after 5 min by addition of 100 µl 1 M H$_3$PO$_4$ and the signal was recorded at 450 nm in an ELISA reader (FIG. 2B).

Characterization of USP21 Inhibition

The activity of USP21 at a concentration of 25 nM in HEPES-buffer (50 mM HEPES, pH 7.5, 0.01% Tween 20 and 10 mM DTT) was measured with Ub-AMC substrate at 1.0 µM in HEPES-buffer at RT. The release of 7-amino-4-methycoumarine was measured at 460 nm in fluorescence spectrometer at an excitation wavelength of 380 nm. The 1050 value was determined as the concentration of Ub variant that reduces USP activity by 50% as normalized to the activity in the absence of Ub variants. The 1050 was determined by incubating the enzyme USP21 with the Ub variants with binding activity to USP21 at concentrations 1 µM, 0.5 µM, 125 nM, 100 nM, 75 nM, 50 nM, 25 nM, 10 nM and 6 nM. The variants Ubv.21.3 (SEQ ID NO: 61 and Ubv.21.4 (SEQ ID NO: 7) were found to inhibit the USP21 with an 1050 of 40 nM and 70 nM, respectively.

Usp21 solution (500 µl, 2.2 mg/ml in 20 mM Tris-HCl, pH 7.0, 0.5 M NaCl, 5% glycerol and 2 mM dithiothreitol) was mixed with Ubv.21.4 (SEQ ID NO: 7) solution (100 µl, 4.9 mg/ml), which resulted in Usp21:Ubv.21.4 (SEQ ID NO: 7) molar ratio of 1:1.6. The mixture was incubated for 1 h at ambient temperature (294 K) followed by incubation for 16 h at 281 K and concentrated by ultrafiltration to a final volume of 150 µl, which resulted in Usp21 concentration of 9 mg/ml. Crystals of the Usp21-inhibitor complex were grown at 291 K using the hanging drop method by mixing equal volumes of the above complex solution and Crystallization Buffer (11% polyethyleneglycol 4000, 0.1 M sodium citrate, pH 5.3, 0.1 M ammonium acetate and 0.5 mM TCEP). The crystals were cryoprotected by immersion in the Crystallization Buffer supplemented with 25% (v/v) glycerol and placed in liquid nitrogen.

Diffraction data from a crystal of the Usp21 catalytic domain in complex with Ubv.21.4 (SEQ ID NO: 7) inhibitor was collected on a Rigaku FR-E Superbright generator equipped with an R-AXIS IV++ detector. The data set was integrated and scaled using the HKL2000 program suite. The structure was solved by molecular replacement techniques using the program PHASER and search model PDB entry 3I3T. Iterative model building using the graphics program Coot and refinement package REFMAC5 led to a model with an R factor of 21.77 (Rfree 27.32%) for data between 20-2.7 Å.

Characterization of USP8 Inhibition

The activity of USP8 at a concentration of 1 nM in HEPES-buffer (50 mM HEPES, pH 7.5, 0.01% Tween 20 and 10 mM DTT) was measured with Ub-AMC substrate at 1.0 µM in HEPES-buffer at RT. The release of 7-amino-4-methycoumarine was measured at 460 nm in fluorescence spectrometer at an excitation wavelength of 380 nm. The 1050 value was determined as the concentration of Ub variant that reduced USP activity by 50% and is normalized to the activity in the absence of Ub variants. The 1050 was determined by incubating the enzyme USP8 with the Ub variants with binding activity to USP8 at concentrations 100 nM, 75 nM, 50 nM, 25 nM, 10 nM, 5 nM 2.5 nM, 1 nM, 0.8 nM and 0.5 nM. The variants Ubv.8.3 (SEQ ID NO: 3) was found to inhibit USP8 with an 1050 of 6 nM.

Usp8 solution (50 µl, 7.6 mg/ml in 20 mM Tris-HCl, pH 7.0, 0.5 M NaCl, 5% glycerol and 2 mM dithiothreitol) was mixed with Ubv.8.2 (SEQ ID NO: 2) (30 µl, 3.5 mg/ml), which resulted in Usp8: inhibitor molar ratio of 1:1. Before setting crystallization plate, the mixture was incubated for 1 h at ambient temperature (294 K) followed by incubation for 16 h at 281 K. Crystals of the Usp8-inhibitor complex were grown at 291 K using the hanging drop method by mixing equal volumes of the above complex solution and Crystallization Buffer (24% polyethyleneglycol 3350, 0.1 M bis-Tris, pH 6.0, 0.2 M ammonium acetate and 0.5 mM dithiothreitol). The crystals were cryoprotected by immersion in the Crystallization Buffer mixed (1:1, v/v) with cryoprotecting mixture that consisted of 20% (w/v) sucrose, 4% (w/v) glucose, 18% (v/v) glycerol and 18% (v/v) ethylene glycol in water and placed in liquid nitrogen.

Diffraction data from a crystal of the Usp8 catalytic domain in complex with Ubv.8.2 (SEQ ID NO: 2) inhibitor was collected on a MAR-300 detector at the Canadian Light Source beamline CMCF 08ID-1. The data set was integrated and scaled using the HKL2000 program suite. The structure was solved by molecular replacement techniques using the program PHASER and search model PDB entry 2GFO and 3MTN. Iterative model building using the graphics program Coot and refinement package REFMAC5 led to a model with an R factor of 17.8 (Rfree 24.2%) for data between 35-2.6 Å. Initial parameters for TLS refinement were obtained from the TLSMD web server.

Example 2—New Ubiquitin Library Design

Ubiquitin variants, previously selected against USP2, USP5, USP7, USP10 and USP46, had heavily altered region 2 sequences which led to misfolded nonspecifically binding clones. Accordingly, the diversity in region 2 was restricted to avoid misfolding and, therefore, the currently designed ubiquitin variant proteins comprises only 6 amino acid residues compared to the original 10 residues in region 2.

Additionally, the randomized region beyond the C-terminus of ubiquitin was extended to target directly the active site of USPs. The USP21:Ubv21.4 inhibitor structure (pdb code: 3MTN) showed that the C-terminus (residues 73 through residues 76) of ubiquitin variant 21.4 is located in the active site of the USP protein. Therefore, a ubiquitin variant was extended by two additional residues to derive an inhibitory variant which spans the active site of the USPs, which could result in optimized contacts in the active site and lead to a more efficient inhibition of the USPs. Additionally, ubiquitin variants with modifications at the C-terminus could reveal critical intramolecular contacts which could facilitate the development of small molecule (<1000 Da) inhibitors of this enzyme class.

Variant design is set out as follows:
Region 1: Q2, F4, K6, L8, T9, G10, K11, T12, T14
Region 2: R42, I44, A46, G47, K48, Q49
Region 3: Q62, K63, E64, H68, V70, L71, R72, L73, R74, G75, G76, G76a (or G77), G76b (or G78)

Example 3—New Target Proteins

A newly designed phage-displayed library, as set out in Example 2 above, was used in selection experiments against USP2a, USP5, USP10 and USP48. At the same time, binders against the E3-ligases Nedd4, ITCH and linear ubiquitin binding motifs (UIM) were selected. USP8 and USP21 were included as positive controls for the selection.

Binders to USP2a

USP2a acts in cooperation with USP7/HAUSP as a positive regulator of HDM2, the major ubiquitin E3 ligase which directs p53 for proteasomal degradation (Priolo, C. 2006). Overexpression of USP2a in non-transformed cells results in an oncogenic phenotype and was shown to prevent apoptosis through chemotherapeutic drugs. Additionally, RNAi-mediated silencing of USP2a leads to an increased apoptosis of several prostate cancer cell lines, which makes USP2a a therapeutically attractive target in prostate cancer.

Figure 5B:
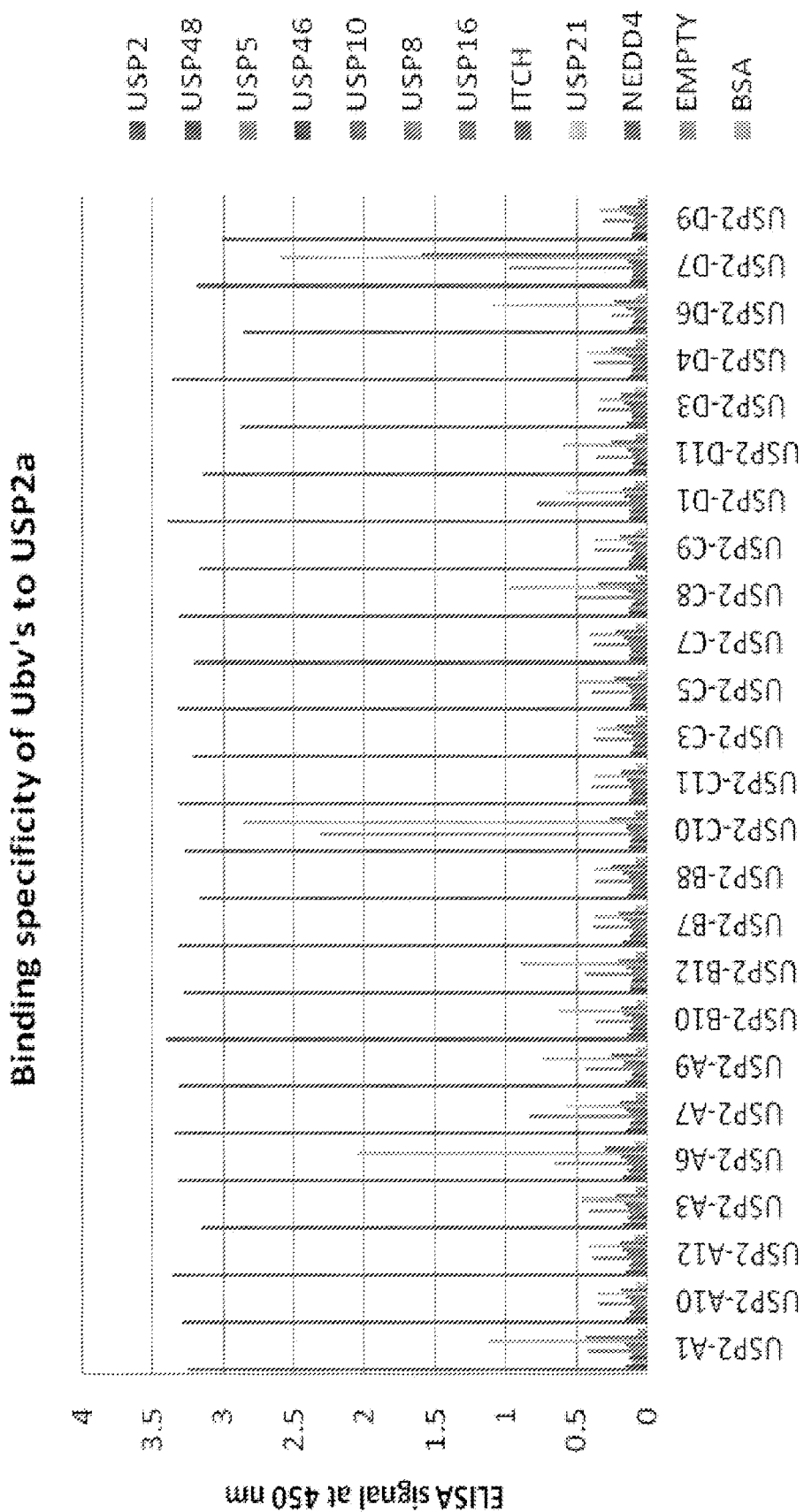

The catalytically active domain of USP2a (residues 251-605) was expressed, biotinylated and immobilized for selection on a neutravidin-coated surface. After 5 consecutive rounds of phage display, individual clones were analyzed for binding activity (FIG. 5B). In total, 26 variants (SEQ ID NOS: 26-47) with specificity for USP2a (FIG. 5A) were identified. Using a competitive ELISA, 6 lead candidates with an affinity of 25 nM or better were identified.

Binders to USP5

USP5/IsoT processes unanchored poly-Ub chains and plays an important role in Ub recycling. Knockdown of USP5 expression by shRNA leads to increased free poly-Ub and increased transcription of the p53 gene (Dayal, S. et al.

Figure 6B:
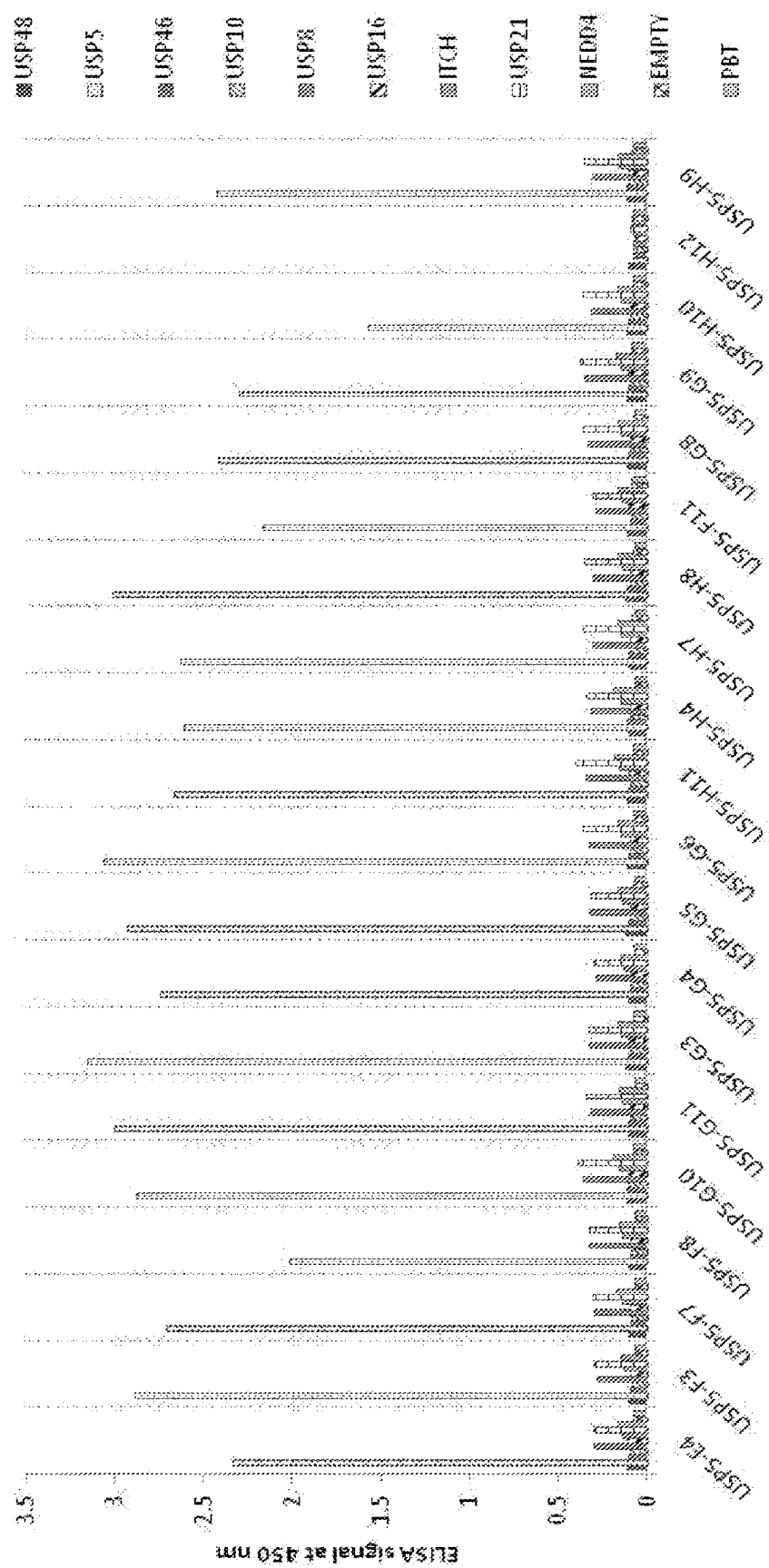

2009). Residues 1-835 of USP5 were expressed in the same format as USP2a, as described herein above. After 5 rounds of selection, 21 unique USP5-binding Ubvs (SEQ ID NOS: 48-68) were identified (FIG. 6A). All 21 selected Ubvs have very good specificity for USP5 (FIG. 6B).

Binders to USP10

Figures 7A, 7B:
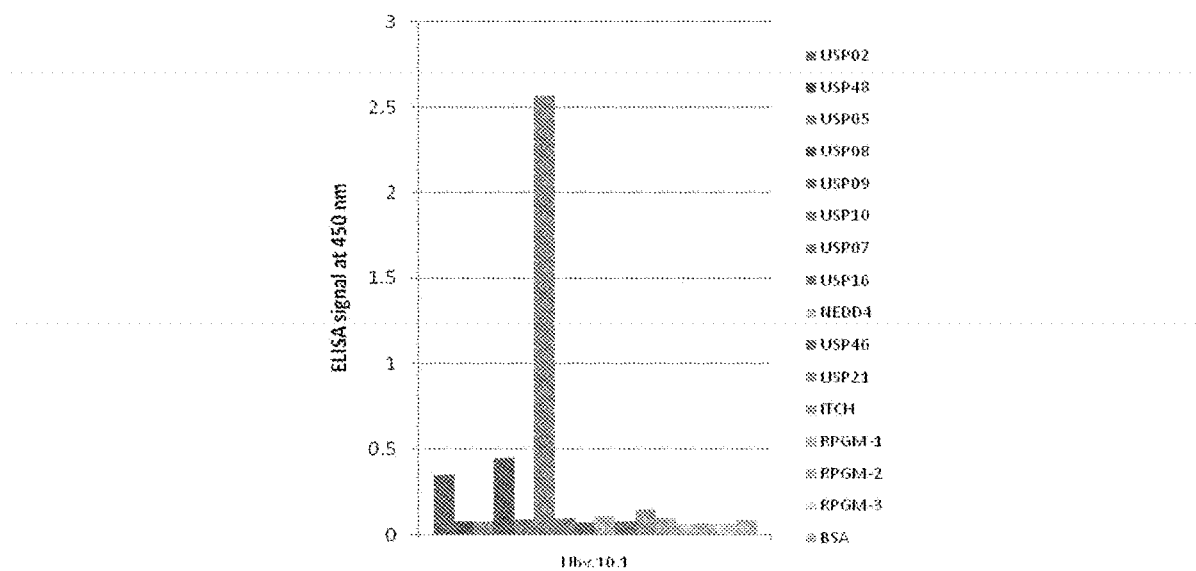
FIGS. 7A-7B shows the identification of one Ub variant (Ubv.10.1 (SEQ ID NO: 69)) as a potent and specific inhibitor of USP10.

USP10 is a cytoplasmic protease which deubiquitinates ubiquitin-labeled p53 and contributes to its stabilization. During DNA damage response, USP10 is stabilized and is involved in nuclear activation of p53 (Yuan, J. 2010). Residues 371-798 of USP10, which comprise the catalytic domain of the enzyme, were expressed. Surprisingly, only one unique ubiquitin variant, Ubv.10.1 (SEQ ID NO: 69), was identified after 5 rounds of selection (FIG. 7A). Ubv.10.1 (SEQ ID NO: 69) has 17 mutations distributed evenly throughout the reading frame of Ub (FIG. 7A). Ubv.10.1 (SEQ ID NO: 69), showed high specificity for USP10 and no binding activity to other USPs (FIG. 7B).

Binders to USP48

Figure 8B:
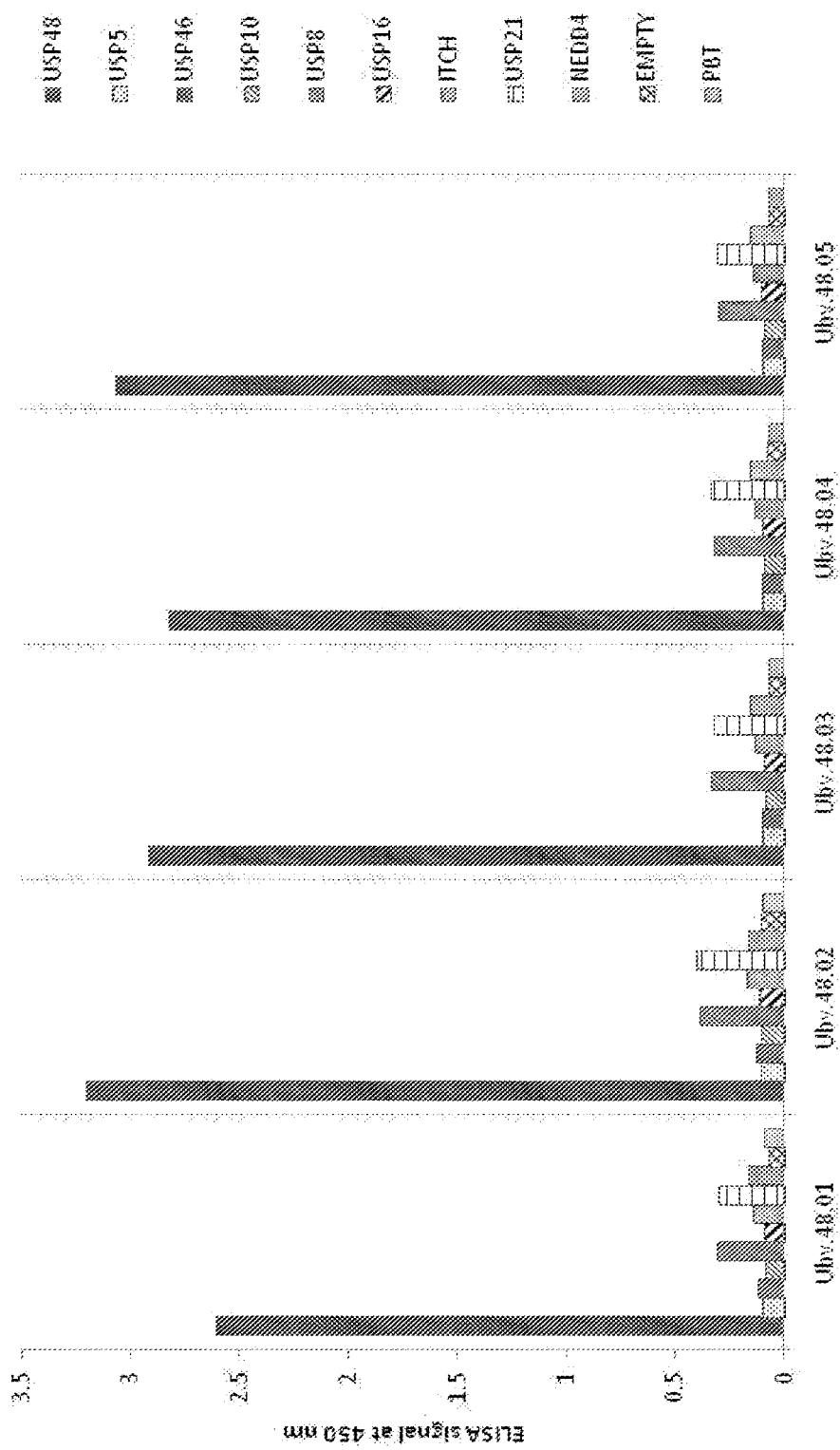

Using genome-wide RNA interference screens, it was found that USP48 is essential for the viability of pancreatic cancer cells that are dependent on the mutant KRAS Small hairpin RNA (shRNA)-mediated knockdown of USP48 shows that certain pancreatic cancer cell lines require USP48 to survive. Residues 38-478 of USP48 were expressed with an N-terminal HIS-tag and a C-terminal in vivo biotinylation tag (AVI-tag). After 5 rounds of selection, 5 unique ubiquitin variants (SEQ ID NOS: 70-74) that showed high binding specificity for USP48 were identified (FIGS. 8A and 8B).

NEDD4 Binders

Figure 9B:
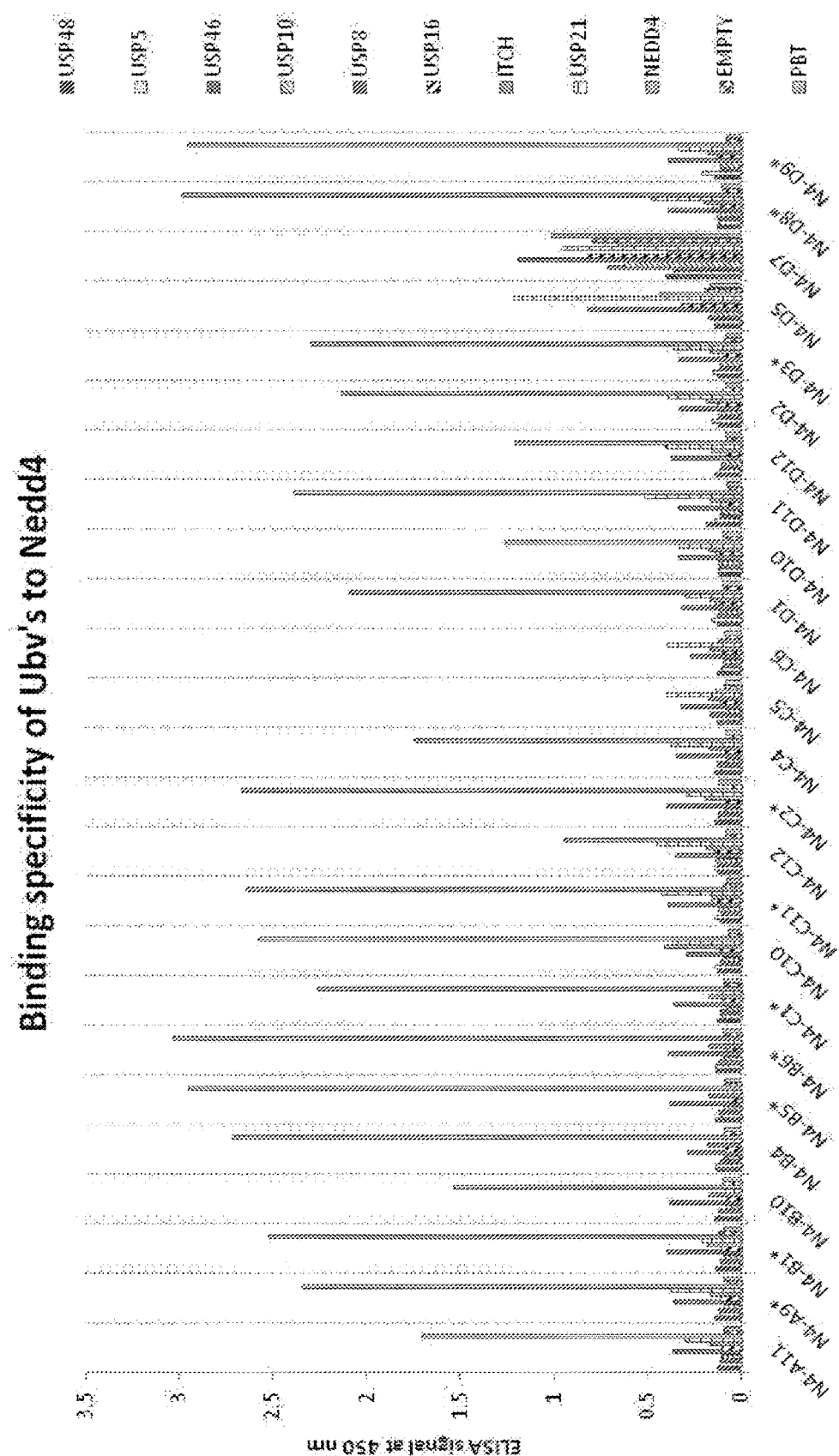

Neural precursor cell expressed developmentally downregulated protein 4 (Nedd4) is an E3 ligase which accepts ubiquitin from an E2 Ub-conjugating enzyme and transfers it to other proteins. Nedd4 functions as a positive regulator of dendrite development and ubiquitinates Rap2a, a member of the Ras oncogene family (Kawabe et al., 2010). Nedd4 ubiquitinates multiple receptor tyrosine kinases, such as EGF receptors, FGF receptor, and IGF1 receptor and functions in their endocytosis and degradation. Additionally, Nedd4 has been identified as a regulator of the tumor suppressor PTEN and is found to be upregulated in bladder and prostate carcinomas. Nedd4 is composed of several WW domains and a catalytically active HECT domain. The WW domain is a highly conserved protein interaction module comprising 35-40 amino acids. The HECT domain (Homologous to the E6-AP Carboxyl Terminus) is an approximately 40 kDa (350-amino acid) catalytic domain found at the carboxyl terminus of HECT-class E3 ubiquitin protein ligases. Nedd4 was included to test additional proteins involved in ubiquitination. Highly specific binders to the HECT-domain of Nedd4 (residues 510-900) were selected. In total, 24 unique ubiquitin variants which bind Nedd4 (SEQ ID NOS: 75-98), and which had mutations in all regions of ub, were identified (FIGS. 9A and 9B). Analysis showed that the mutations G10R, I44F, Q49K, H68Y, L71K and G76M are conserved. These mutations could make beneficial contacts to residues in Nedd4. For example, G10R is implicated for its role in forming a new salt bridge to D614 in Nedd4 and, thereby, increasing affinity.

ITCH Binders

Figure 10B:
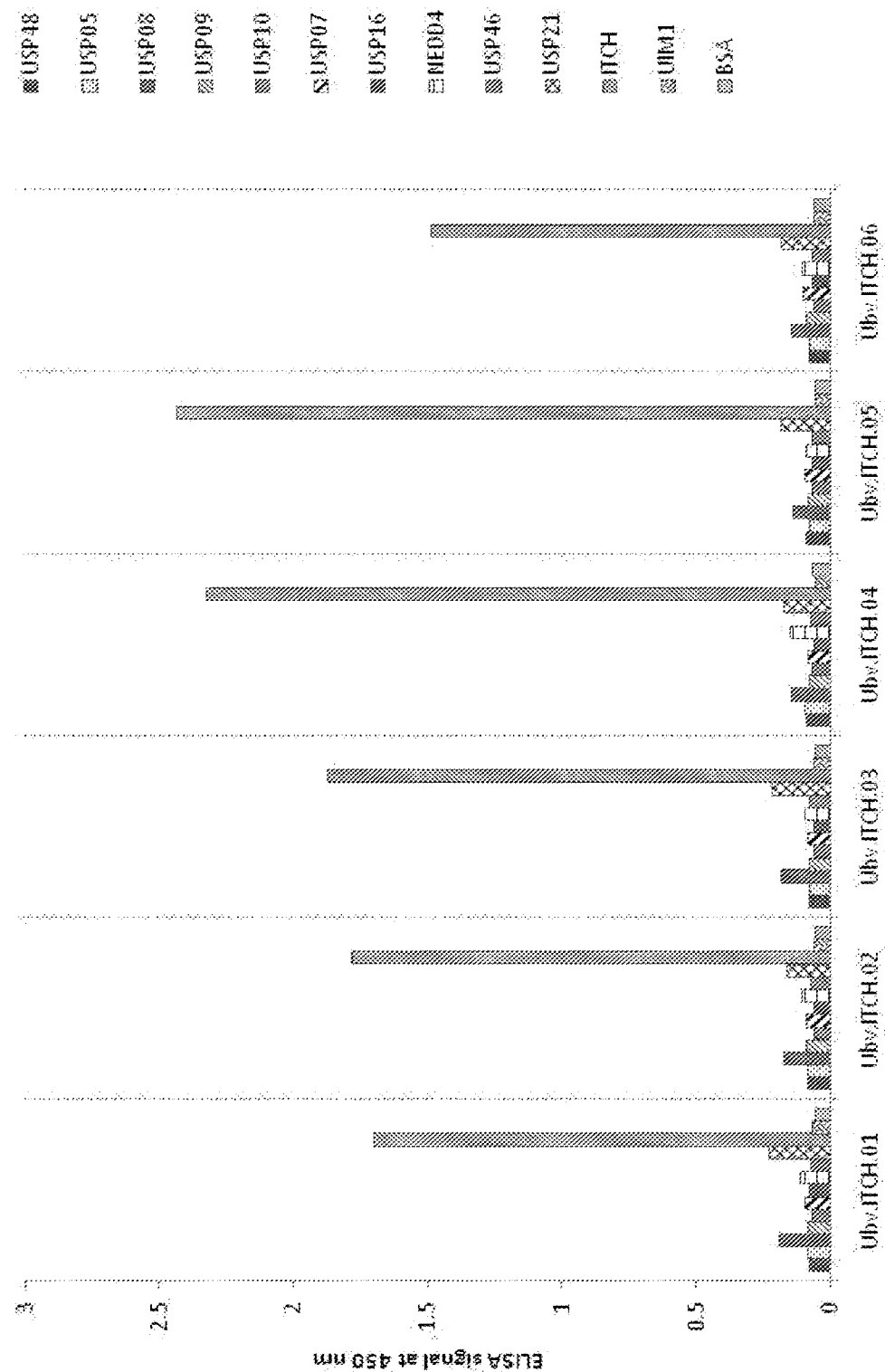

The ubiquitin ligase, ITCH, acts as an E3 ubiquitin protein ligase. ITCH accepts ubiquitin from an E2 ubiquitin-conjugating enzyme in the form of a thioester and then directly transfers the ubiquitin to targeted substrates. ITCH catalyzes 'Lys-29'-, 'Lys-48'- and 'Lys-63'-linked ubiquitin conjugation. ITCH belongs to the family of HECT-domain E3 ligases and is closely related to Nedd4. Residues 483-862 of ITCH, which comprise the HECT domain, were expressed. After 5 rounds of selection, 6 unique binders to ITCH (SEQ ID NOS: 99-104) (FIGS. 10A and 10B) were identified. The selected binders had an average of 16 mutations distributed over the Ub scaffold.

UIM Binders

Ubiquitin interaction motifs (UIM) are linear sequence motifs which are part of other proteins. UIMs have been shown to bind ubiquitin and to serve as a specific targeting signal important for monoubiquitination. UIMs are often found in a variety of proteins involved in ubiquitination and ubiquitin metabolism, or interact with ubiquitin-like modifiers. For example, UIMs play a major role in endosomal sorting and recognize either poly-ubiquitinated or mono-ubiquitinated substrates.

Selection for UIM binders was made against a linear peptide corresponding to UIM1 (RPGM-1) of vacuole-protein-sorting 27 protein (VPS27p) of yeast. UIM1 is part of a yeast protein, VPS27, and is responsible for the recognition of ubiquitin in ubiquitinated proteins. UIM1 is part of the endosomal sorting complex ESCRT0 which is responsible for the trafficking and degradation of ubiquitinated receptors, such as EGFR. An engineered variant, therefore, can compete with Ub.wt (SEQ ID NO: 1) binding and interfere with endosomal sorting.

Two peptides, UIM1a (RPGM-2) and IUM1b (RPGM-3), comprising point mutations of the UIM1 abolishing UB binding were identified.

```
UIM1:
                                        (SEQ ID NO: 170)
GGGGAADEEELIRKAIELSLKESRNSGGY

UIM1a:
                                        (SEQ ID NO: 171)
GGGGAADEEELIRKAIELALKESRNSGGY

UIM1b:
                                        (SEQ ID NO: 172)
GGGGAADEEELIRKLIELSLKESRNSGGY
```

Figure 11B:
Figure 11C:
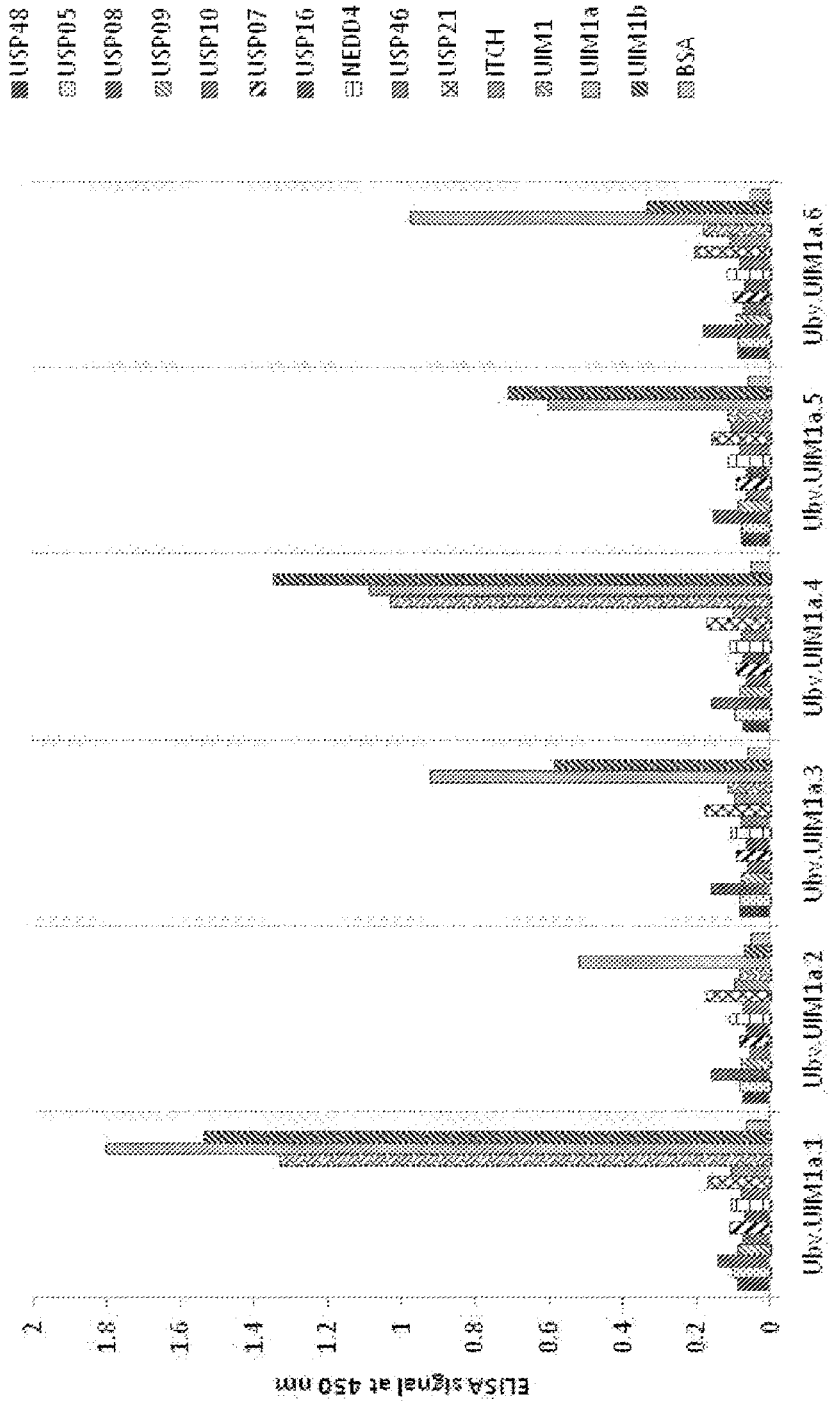
Figure 11D:
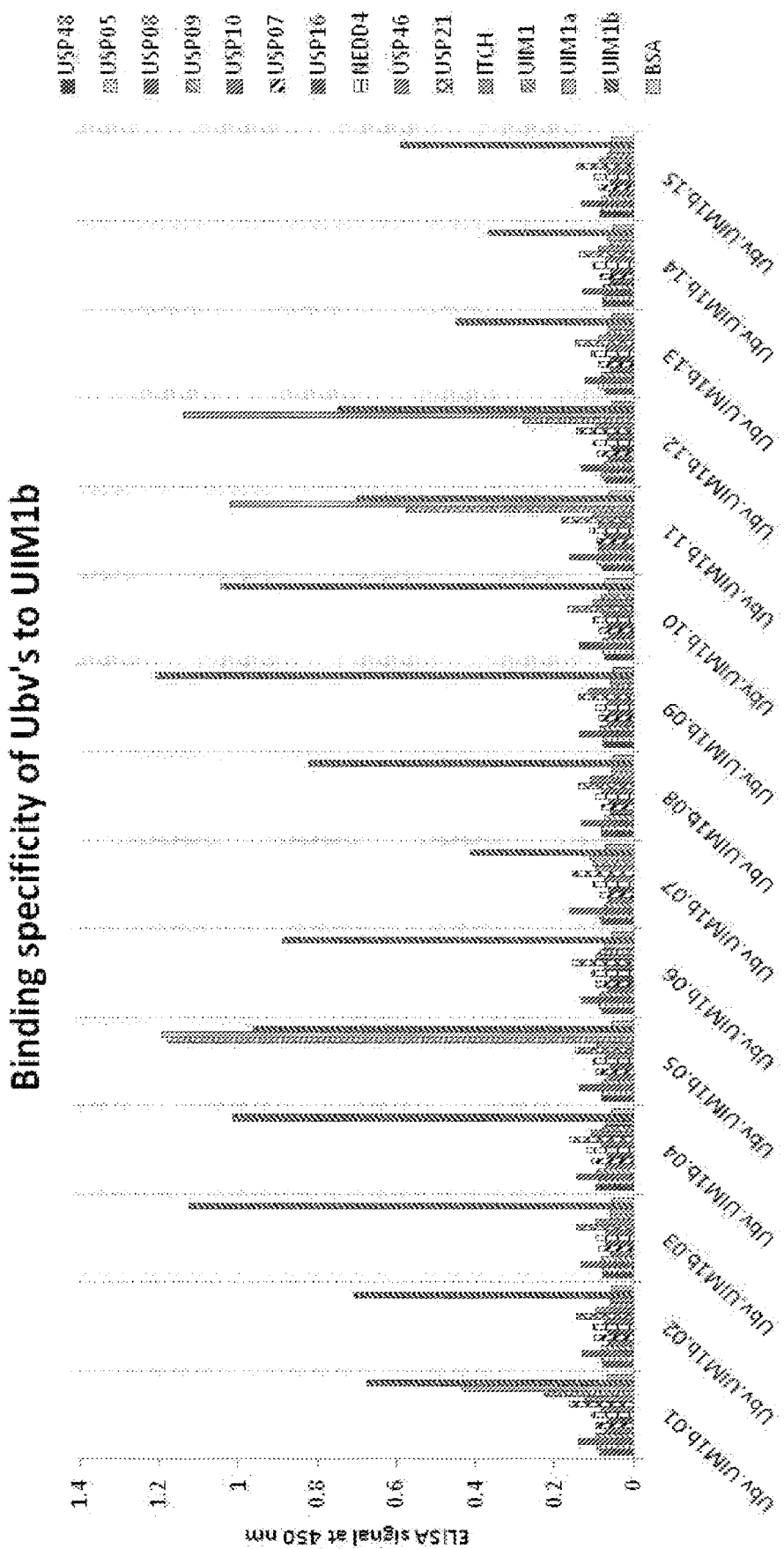
Figure 12B:
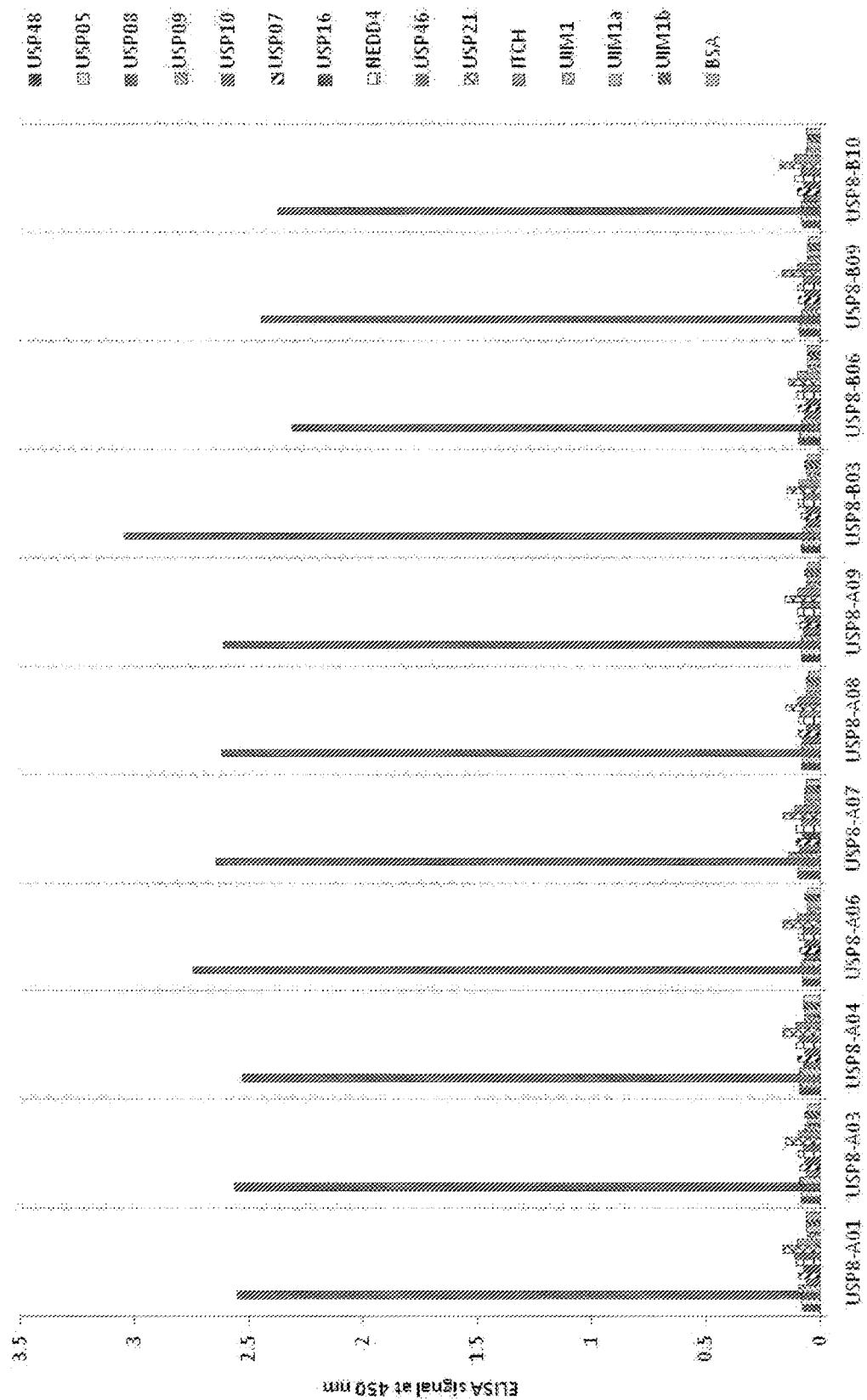
Figure 13B:
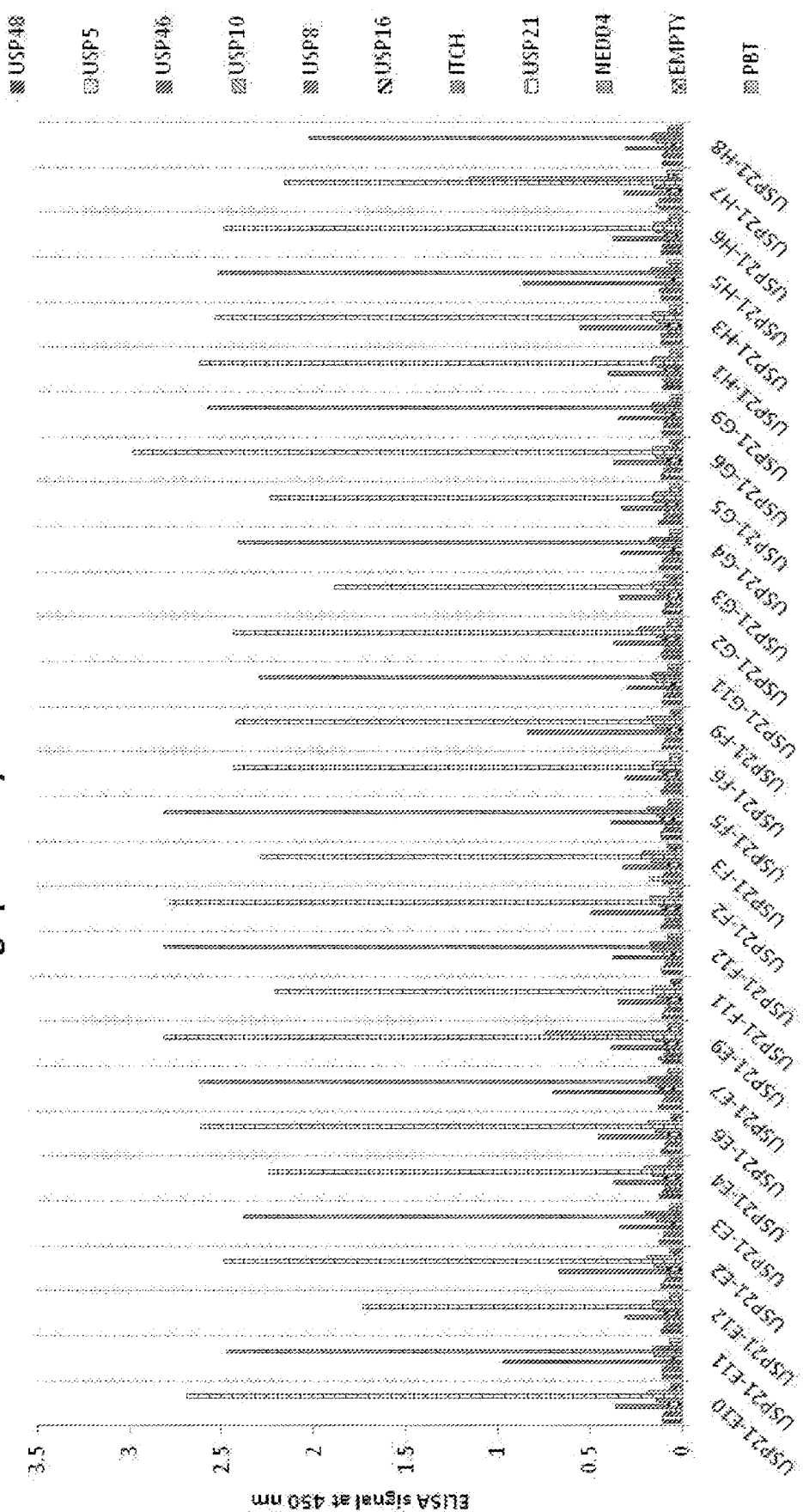

Similar to Nedd4, these peptide motifs were used in selections to expand on other intracellular ub binding moieties. High-affinity binders against these motifs could be used to interfere with endosomal sorting mechanisms and are considered valuable research tools. Four unique binders recognizing UIM1; 6 unique binders in the UIM1a selection; and 15 unique binders in the UIM1b selection were identified (SEQ ID NOS: 105-129) (FIG. 11A). All Ubvs showed no binding to other ubiquitin binding moieties, such as USPs or E3 ligases. However, the selected variants had varying degrees of specificity amongst themselves. For example, several variants recognizing all three UIM1 peptides (UIM1, UIM1a, and UIM1b), two UIM1 peptides, or one UIM1 peptide, respectively, were identified (FIGS. 11B-11D).

Binders for USP8 and USP21

Additional experiments for USP8 and USP21 binders were carried out with the 78-amino acid Ub.wt variant of SEQ ID NO: 21. As positive controls, all selection experiments for USP8 and USP21 were included. Inhibitors for both enzymes, USP8 and USP21, were previously developed as described herein above in Example 1. In these new experiments, several more unique binders against USP8 (11 ubv, SEQ ID NOS: 130-140) and USP21 (29 ubv, SEQ ID NOS: 141-169) were identified. These 40 new Ubvs showed high specificity (FIGS. 12A-12B and 13A-13B), comparable to specificity of USP8 and USP21 binders previously identified.

Example 4—Measurement of Ubv.21.4 (SEQ ID NO: 7) and Ubv.8.2 (SEQ ID NO: 2) IC50

Figure 14A:
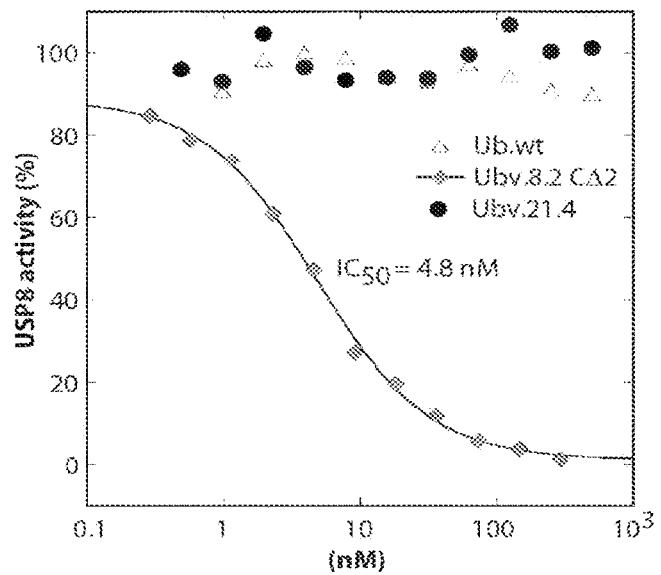
FIGS. 14A-14B shows dose response curves for the inhibition of USP8 and USP21 by Ubv.8.2 (SEQ ID NO: 2) (FIG. 14A) and Ubv.21.4 (SEQ ID NO: 7) (FIG. 14B), respectively.
Figure 14B:
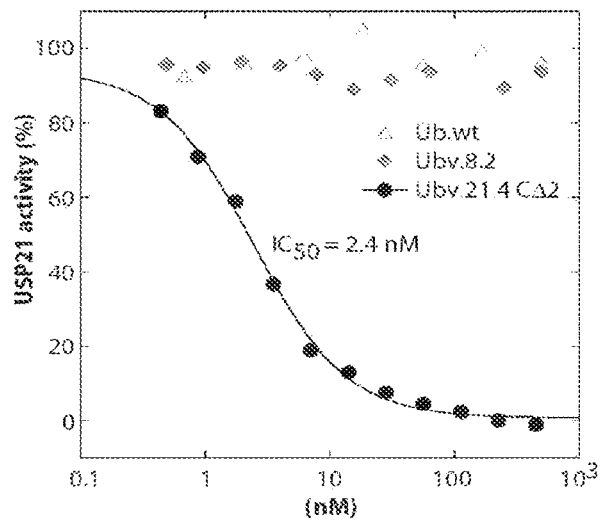

Inhibition experiments with Ubv.8.2 (SEQ ID NO: 2) and Ubv.21.4 (SEQ ID NO: 7) were repeated with some modifications. Previous measurements showed a slight salt effect on proteolytic activity, which led to an underestimation of the affinity of Ubv.21.4 (SEQ ID NO: 7). Therefore, C-terminally truncated versions of two variants, Ubv.8.2 (SEQ ID NO: 2) and Ubv.21.4 (SEQ ID NO: 7), were measured, thereby avoiding activation and conjugation to other intracellular proteins. FIGS. 14A and 14B show the new dose-response curves.

Example 5—Intracellular Inhibition of USP21 by Co-Expression of Ubv.21.4

Figure 15A:
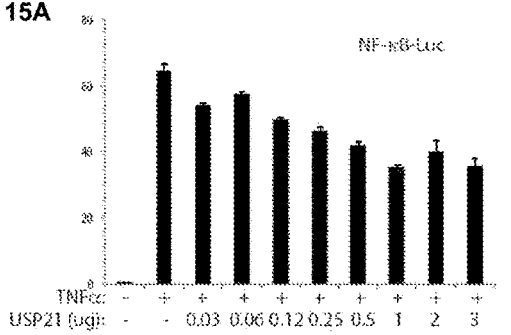
FIGS. 15A-15F shows Ubv.21.4 (SEQ ID NO: 7) CΔ2 mutant specifically inhibits USP21 activity through intracellular interaction with USP21.
Figure 15B:
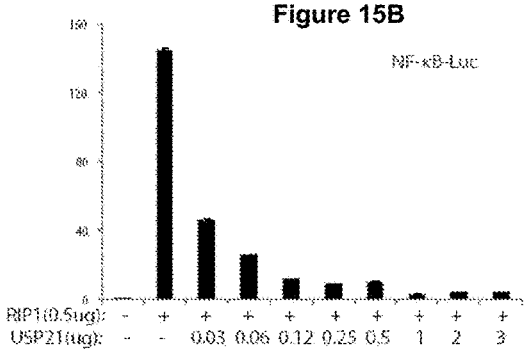

Previous experiments already have established the inhibitory potential of Ubv.8.2 (SEQ ID NO: 2) and Ubv.21.4 (SEQ ID NO: 7) on USP8 and USP21, respectively, in vitro. Both binders inhibit their cognate USP with a single digit nanomolar IC50. Thus, experiments were carried out to determine whether Ubv.21.4 (SEQ ID NO: 7) inhibits USP21 activity in vivo. USP21 inhibits TNFα and RIP1-induced NFκB activation in a dose-dependent manner (FIGS. 15A and 15B) (Xu, G. F. et al. 2010).

Figure 15C:
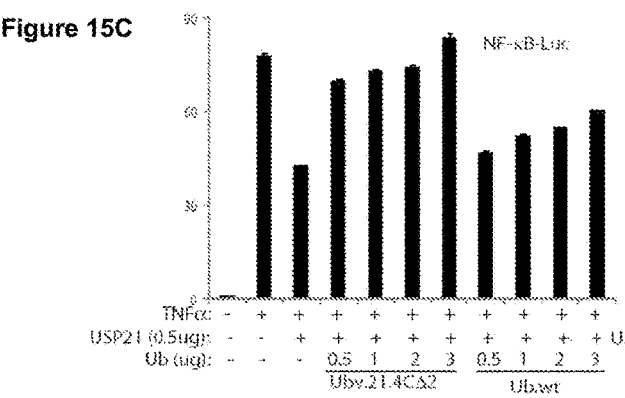
Figure 15D:
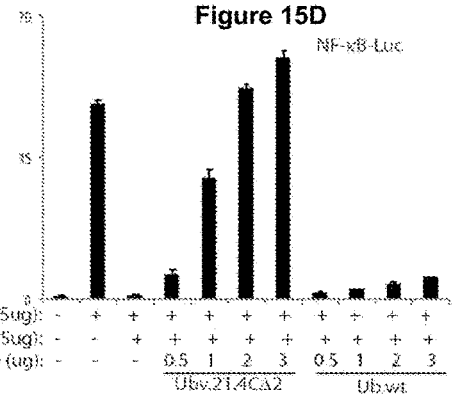
Figure 15E:
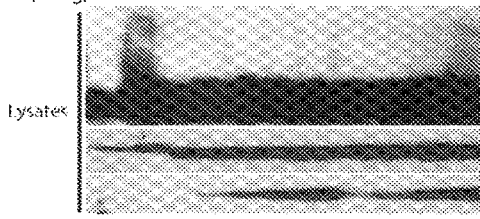
Figure 15F:
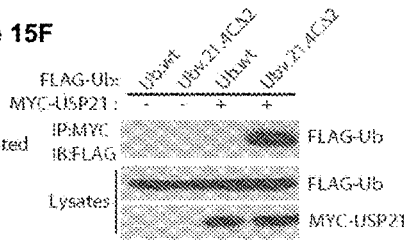

When increasing amounts of either Ub.wt (SEQ ID NO: 1) or Ubv.21.4 (SEQ ID NO: 7) were co-expressed with USP21, Ubv.21.4 (SEQ ID NO: 7), but not Ub.wt (SEQ ID NO: 1), suppressed the inhibitory effect of USP21 on TNFα- and RIP1-induced NF-κB activation (FIGS. 15C and 15D). Consequently, Ubv.21.4 (SEQ ID NO: 7), but not Ub.wt (SEQ ID NO: 11, rescued the inhibitory effect of USP21 on RIP1 polyubiquitination (FIG. 15E). Consistent with these results, USP21 co-immunoprecipitated with Ubv.21.4 (SEQ ID NO: 7), but did not co-immunoprecipitate with Ub-wt, in 293T cells co-transfected with plasmids to express these proteins (FIG. 15F). Taken together, these data show that Ubv.21.4 (SEQ ID NO: 7) specifically blocks USP21 activity through physical binding with USP21 in the cells.

Experiments showing that Ubv.8.2 (SEQ ID NO: 2) inhibits USP8 intracellularly are ongoing. It has been established, however, by mass spectroscopy that both Ubv.8.2 (SEQ ID NO: 2) and Ubv.21.4 (SEQ ID NO: 7) bind to their cognate USP in cells.

Example 6—Ubiquitin Inhibitors Cause Apoptosis in Cancer Cells and/or Cause Tumor Regression Lentiviruses can stably infect most cell types, including primary and non-dividing cells, and lentiviral-based libraries can be used for genetic selection screens (Moffat et al, 2006). Adapting Ub variants into lentiviruses accelerates discovery of inhibitors that induce a particular phenotype, such as apoptosis and cell growth arrest, in relevant cell types. Additionally, lentivirus allows direct in vivo experiments in mouse models of disease. Thus, lentiviral-based constructs for stable and inducible expression of GFP-Ubv.8.2 (SEQ ID NO: 2) and GFP-Ubv.8.3 (SEQ ID NO: 3) are constructed. These ubiquitin variants are used with USP8 inhibitors to explore effects on EGFR signaling. The GFP-Ubv.8.2 (SEQ ID NO: 2) and GFP-Ubv.8.3 (SEQ ID NO: 3) constructs are used to generate EGFR-dependent cell lines harbouring these Ub variants under the control of a constitutive or doxycycline-inducible promoter. These experiments will be used to optimize lentiviral delivery of ubiquitin variants. Multiple cancer cell lines are screened in a high throughput manner to explore the phenotypic effects that the ubiquitin inhibitors have on these cells.

Example 7—Ubiquitin Inhibitors for Screening Small Molecule Libraries

The ubiquitin variants are also used to screen small molecule compound libraries for the inhibition of USPs, OTUs, E3 ligases and E2-conjugating enzymes. In such a screen, a high affinity ubiquitin variant is labeled with a fluorescent dye allowing the measurement of fluorescence polarization (FP) of an enzyme ubiquitin variant complex and the free ubiquitin variant (Hafner et al., 2008). FP directly correlates with the hydrodynamic radius and diffusion of labeled proteins in solution, i.e., a labeled ubiquitin variant dissociated from an enzyme complex has lower FP values compared to the complex bound form. Therefore, a fluorescence-labeled high affinity ubiquitin variant could be displaced from the active site of an enzyme by a small molecule which results in a decrease of FP compared to the intact complex. Additionally, the affinity of a small molecule binding to the active site directly correlates with the affinity of the displaced engineered ubiquitin variant. These screens are performed in a high-throughput fashion and could potentially result in a series of small molecules specifically inhibiting enzymes of the ubiquitination pathways in vitro and in vivo.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Avvakumov, G. V., J. R. Walker, et al. (2006). "Amino-terminal dimerization, NRDP1-rhodanese interaction, and inhibited catalytic domain conformation of the ubiquitin-specific protease 8 (USP8)." *Journal of Biological Chemistry* 281(49): 38061-38070.

Bernassola, F., M. Karin, et al. (2008). "The HECT family of E3 ubiquitin ligases: multiple players in cancer development." *Cancer Cell* 14(1): 10-21.

Case, A. and R. L. Stein (2006). "Mechanistic studies of ubiquitin C-terminal hydrolase L1." *Biochemistry* 45(7): 2443-2452.

Chen, Z. J. J. (2005). "Ubiquitin signalling in the NF-kappa B pathway." *Nature Cell Biology* 7(8): 758-U19.

Colland, F., E. Formstecher, et al. (2009). "Small-molecule inhibitor of USP7/HAUSP ubiquitin protease stabilizes and activates p53 in cells." *Molecular Cancer Therapeutics* 8(8): 2286-2295.

Cummins, J. M. and B. Vogelstein (2004). "HAUSP is required for p53 destabilization." *Cell Cycle* 3(6): 689-692.

Dayal, S., A. Sparks, et al. (2009). "Suppression of the deubiquitinating enzyme USP5 causes the accumulation of unanchored polyubiquitin and the activation of p53." *J Biol Chem* 284(8): 5030-41.

Fang, S. and A. M. Weissman (2004). "A field guide to ubiquitylation." *Cell Mol Life Sci* 61(13): 1546-61.

Fedorov, O., B. Marsden, et al. (2007). "A systematic interaction map of validated kinase inhibitors with Ser/Thr kinases." *Proceedings of the National Academy of Sciences of the United States of America* 104(51): 20523-20528.

Fellouse, F. A. and S. S. Sidhu (2007). Making antibodies in bacteria. *Making and using antibodies*. G. C. Howard and M. R. Kaser. Boca Raton, Fla., CRC Press 157-180.

Glickman, M. H. and A. Ciechanover (2002). "The ubiquitin-proteasome proteolytic pathway: Destruction for the sake of construction." *Physiological Reviews* 82(2): 373-428.

Goldenberg, S. J., J. L. McDermott, et al. (2008). "Strategies for the identification of novel inhibitors of deubiquitinating enzymes." *Biochemical Society Transactions* 36: 828-832.

Gray, D. A., J. Inazawa, et al. (1995). "Elevated Expression of Unph, a Protooncogene at 3P21.3, in Human Lung-Tumors." *Oncogene* 10(11): 2179-2183.

Grunda, J. M., L. B. Nabors, et al. (2006). "Increased expression of thymidylate synthetase (TS), ubiquitin specific protease 10 (USP10) and survivin is associated with poor survival in glioblastoma multiforme (GBM)." *Journal of Neuro-Oncology* 80(3): 261-274.

Hafner, M., E. Vianini, et al. (2008). "Displacement of protein-bound aptamers with small molecules screened by fluorescence polarization." *Nat Protoc* 3(4): 579-87.

Hershko, A. and A. Ciechanover (1998). "The ubiquitin system." *Annual Review of Biochemistry* 67: 425-479.

Hu, M., P. W. Li, et al. (2002). "Crystal structure of a UBP-family deubiquitinating enzyme in isolation and in complex with ubiquitin aldehyde." *Cell* 111(7): 1041-1054.

Hu, M., P. W. Li, et al. (2005). "Structure and mechanisms of the proteasome-associated deubiquitinating enzyme USP14." *Embo Journal* 24(21): 3747-3756.

Kawabe, H., A. Neeb, et al. (2010). "Regulation of Rap2A by the ubiquitin ligase Nedd4-1 controls neurite development." *Neuron* 65(3): 358-72.

Komander, D., M. J. Clague, et al. (2009). "Breaking the chains: structure and function of the deubiquitinases." *Nature Reviews Molecular Cell Biology* 10(8): 550-563.

Li, B., H. K. Xi, et al. (2009). "Improving Therapeutic Efficacy of a Complement Receptor by Structure-based Affinity Maturation." *Journal of Biological Chemistry* 284(51): 35605-35611.

Li, M. Y., C. L. Brooks, et al. (2004). "A dynamic role of HAUSP in the p53-Mdm2 pathway." *Molecular Cell* 13(6): 879-886. Maspero, E., S. Mari, et al. (2011). "Structure of the HECT:ubiquitin complex and its role in ubiquitin chain elongation." *EMBO Rep* 12(4): 342-9.

Mizuno, E., T. Iura, et al. (2005). "Regulation of epidermal growth factor receptor down-regulation by UBPY-mediated deubiquitination at endosomes." *Molecular Biology of the Cell* 16(11): 5163-5174.

Moffat, J., D. A. Grueneberg, et al. (2006). "A lentiviral RNAi library for human and mouse genes applied to an arrayed viral high-content screen." *Cell* 124(6): 1283-98.

Morita, E. and W. I. Sundquist (2004). "Retrovirus budding." *Annu Rev Cell Dev Biol* 20: 395-425.

Nakagawa, T., T. Kajitani, et al. (2008). "Deubiquitylation of histone H2A activates transcriptional initiation via trans-histone cross-talk with H3K4 di- and trimethylation." *Genes & Development* 22(1): 37-49.

Niendorf, S., A. Oksche, et al. (2007). "Essential role of ubiquitin-specific protease 8 for receptor tyrosine kinase stability and endocytic trafficking in vivo." *Molecular and Cellular Biology* 27(13): 5029-5039.

Nijman, S. M. B., T. T. Huang, et al. (2005). "The deubiquitinating enzyme USP1 regulates the Fanconi anemia pathway." *Molecular Cell* 17(3): 331-339.

Nijman, S. M. B., M. P. A. Luna-Vargas, et al. (2005). "A genomic and functional inventory of deubiquitinating enzymes." *Cell* 123(5): 773-786.

Pearce, K. H., B. J. Potts, et al. (1997). "Mutational analysis of thrombopoietin for identification of receptor and neutralizing antibody sites." *Journal of Biological Chemistry* 272(33): 20595-20602.

Priolo, C., D. Tang, et al. (2006). "The isopeptidase USP2a protects human prostate cancer from apoptosis." *Cancer Research* 66(17): 8625-8632.

Ren, X. and J. H. Hurley (2010). "VHS domains of ESCRT-0 cooperate in high-avidity binding to polyubiquitinated cargo." *EMBO J* 29(6): 1045-54.

Renatus, M., S. G. Parrado, et al. (2006). "Structural basis of ubiquitin recognition by the deubiquitinating protease USP2." *Structure* 14(8): 1293-1302.

Reyes-Turcu, F. E., K. H. Ventii, et al. (2009). "Regulation and Cellular Roles of Ubiquitin-Specific Deubiquitinating Enzymes." *Annual Review of Biochemistry* 78: 363-397.

Saggar, S., K. A. Chernoff, et al. (2008). "CYLD mutations in familial skin appendage tumours." *Journal of Medical Genetics* 45(5): 298-302.

Sidhu, S. S., B. Li, et al. (2004). "Phage-displayed antibody libraries of synthetic heavy chain complementarity determining regions." *Journal of Molecular Biology* 338(2): 299-310.

Sidhu, S. S., H. B. Lowman, et al. (2000). Phage display for selection of novel binding peptides. *Applications of Chimeric Genes and Hybrid Proteins*, Pt C. San Diego, Academic Press Inc. 328: 333-363.

Stevenson, L. F., A. Sparks, et al. (2007). "The deubiquitinating enzyme USP2a regulates the p53 pathway by targeting Mdm2." *Embo Journal* 26(4): 976-986.

Tao, M., P. C. Scacheri, et al. (2009). "ITCH K63-ubiquitinates the NOD2 binding protein, RIP2, to influence inflammatory signaling pathways." *Curr Biol* 19(15): 1255-63.

Tonikian, R., Y. N. Zhang, et al. (2007). "Identifying specificity profiles for peptide recognition modules from phage-displayed peptide libraries." *Nature Protocols* 2(6): 1368-1386.

Ventii, K. H. and K. D. Wilkinson (2008). "Protein partners of deubiquitinating enzymes." *Biochemical Journal* 414: 161-175.

Wilkinson, K. D. (1997). "Regulation of ubiquitin-dependent processes by deubiquitinating enzymes." *Faseb Journal* 11(14): 1245-1256.

Wollert, T. and J. H. Hurley (2010). "Molecular mechanism of multivesicular body biogenesis by ESCRT complexes." *Nature* 464(7290): 864-9.

Xu, G. F., X. J. Tan, et al. (2010). "Ubiquitin-specific Peptidase 21 Inhibits Tumor Necrosis Factor alpha-induced Nuclear Factor kappa B Activation via Binding to and Deubiquitinating Receptor-interacting Protein 1." *Journal of Biological Chemistry* 285(2): 969-978. Ye, Y.

H. and M. Rape (2009). "Building ubiquitin chains: E2 enzymes at work." *Nature Reviews Molecular Cell Biology* 10(11): 755-764.

Yim, E. K., G. Peng, et al. (2009). "Rak functions as a tumor suppressor by regulating PTEN protein stability and function." *Cancer Cell* 15(4): 304-14.

Yuan, J., K. T. Luo, et al. (2010). "USP10 Regulates p53 Localization and Stability by Deubiquitinating p53." *Cell* 140(3): 384-U121.

Zhang, D., K. Zaugg, et al. (2006). "A role for the deubiquitinating enzyme USP28 in control of the DNA-damage response." *Cell* 126(3): 529-542.

Zhang, X. Y., M. Varthi, et al. (2008). "The putative cancer stem cell marker USP22 is a subunit of the human SAGA complex required for activated transcription and cell-cycle progression." *Molecular Cell* 29(1): 102-111.

The invention claimed is:

1. A specific inhibitor of a deubiquitinating enzyme, wherein the deubiquitinating enzyme is USP21, and wherein the inhibitor of USP21 is a ubiquitin variant comprising the amino acid sequence set forth in any of SEQ ID NO: 5, 6, or 7.

2. The inhibitor of claim 1, wherein the ubiquitin variant comprises the amino acid sequence set forth in SEQ ID NO: 5.

3. The inhibitor of claim 1, wherein the ubiquitin variant comprises the amino acid sequence set forth in SEQ ID NO: 6.

4. The inhibitor of claim 1, wherein the ubiquitin variant comprises the amino acid sequence set forth in SEQ ID NO: 7.

* * * * *

UNITED STATES PATENT AND TRADEMARK OFFICE
CERTIFICATE OF CORRECTION

PATENT NO. : 10,562,945 B2
APPLICATION NO. : 16/239784
DATED : February 18, 2020
INVENTOR(S) : Sachdev Sidhu et al.

It is certified that error appears in the above-identified patent and that said Letters Patent is hereby corrected as shown below:

On the Title Page

At item (60), Lines 2-3, "2010, provisional application No. 61/372,133, filed on Aug. 10, 2010." should be -- 2010. --.

Signed and Sealed this
Eighteenth Day of August, 2020

Andrei Iancu
*Director of the United States Patent and Trademark Office*